United States Patent
Blom et al.

(10) Patent No.: US 9,090,630 B2
(45) Date of Patent: Jul. 28, 2015

(54) MACROCYCLIC FLT3 KINASE INHIBITORS

(71) Applicant: ONCODESIGN S.A., Dijon Cedex (FR)

(72) Inventors: Petra Marcella Francoise Blom, Destelbergen (BE); Jan Marie Cyriel Jozef Hoflack, Malle (BE)

(73) Assignee: Oncodesign S.A., Dijon Cedex (FR)

( * ) Notice: Subject to any disclaimer, the term of this patent is extended or adjusted under 35 U.S.C. 154(b) by 0 days.

(21) Appl. No.: 14/347,750

(22) PCT Filed: Sep. 28, 2012

(86) PCT No.: PCT/EP2012/069252
§ 371 (c)(1),
(2) Date: Mar. 27, 2014

(87) PCT Pub. No.: WO2013/045653
PCT Pub. Date: Apr. 4, 2013

(65) Prior Publication Data
US 2014/0303159 A1    Oct. 9, 2014

(30) Foreign Application Priority Data
Sep. 30, 2011 (WO) ................. PCT/EP2011/067084

(51) Int. Cl.
*C07D 471/22* (2006.01)
*C07D 487/18* (2006.01)
*C07D 498/18* (2006.01)

(52) U.S. Cl.
CPC ............ *C07D 498/18* (2013.01); *C07D 471/22* (2013.01); *C07D 487/18* (2013.01)

(58) Field of Classification Search
CPC ... C07D 487/18; C07D 498/18; C07D 471/22
USPC ............................ 514/257; 540/456, 469, 472
See application file for complete search history.

(56) References Cited

U.S. PATENT DOCUMENTS

| 6,369,086 | B1 | 4/2002 | Davis et al. |
| 6,369,087 | B1 | 4/2002 | Whittle et al. |
| 6,372,733 | B1 | 4/2002 | Caldwell et al. |
| 6,372,778 | B1 | 4/2002 | Tung et al. |
| 2014/0206683 | A1* | 7/2014 | Hoflack et al. .............. 514/233.2 |

FOREIGN PATENT DOCUMENTS

| WO | 2004039782 A1 | 5/2004 |
| WO | 2006050946 A1 | 5/2006 |
| WO | 2007044420 A1 | 4/2007 |
| WO | 2007048088 A2 | 4/2007 |
| WO | 2008016665 A2 | 2/2008 |
| WO | 2008037477 A1 | 4/2008 |
| WO | 2008058126 A2 | 5/2008 |
| WO | 2008060248 A1 | 5/2008 |
| WO | 2009017795 A1 | 2/2009 |
| WO | 2009097446 A1 | 8/2009 |
| WO | 2009109071 A1 | 9/2009 |
| WO | 2010036380 A1 | 4/2010 |
| WO | 2010119284 A1 | 10/2010 |
| WO | 2011003065 A2 | 1/2011 |
| WO | WO 2013/001310 | * 1/2013 |

OTHER PUBLICATIONS

International Search Report and Written Opinion dated Jan. 25, 2013 pertaining to International No. PCT/EP2012/069252.
Stirewalt et al., "The Role of FLT3 in Haematopoietic Malignancies", Nature Reviews/Cancer, Sep. 2003, vol. 3, pp. 650-666.

* cited by examiner

*Primary Examiner* — Bruck Kifle
(74) *Attorney, Agent, or Firm* — Dinsmore & Shohl LLP

(57) ABSTRACT

The present invention relates to macrocylic compounds and compositions containing said compounds acting as kinase inhibitors, in particular as inhibitors of FLT3 (FMS-Related Tyrosine kinase 3). Moreover, the present invention provides processes for the preparation of the disclosed compounds, as well as methods of using them, for instance as a medicine, in particular for the treatment of cell proliferative disorders, such as cancer.

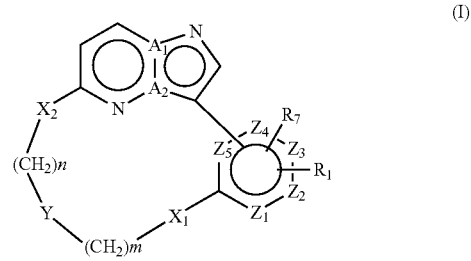

(I)

14 Claims, No Drawings

MACROCYCLIC FLT3 KINASE INHIBITORS

FIELD OF THE INVENTION

The present invention relates to macrocylic compounds and compositions containing said compounds acting as kinase inhibitors, in particular as inhibitors of FLT3 (FMS-Related Tyrosine kinase 3). Moreover, the present invention provides processes for the preparation of the disclosed compounds, as well as methods of using them, for instance as a medicine, in particular for the treatment of cell proliferative disorders, such as cancer.

BACKGROUND OF THE INVENTION

Protein kinases constitute a large family of structurally related enzymes that are responsible for the control of a wide variety of signal transduction processes in the cell. They have been shown to be key regulators in most cellular functions including proliferation, cell metabolism, cell survival, apoptosis, DNA damage repair, cell motility, . . . The protein kinase activity is based on phosphorylation events which act as molecular on/off switches that can modulate or regulate the target protein's biological function. Phosphorylation of target proteins occurs in response to a variety of extracellular signals (hormones, neurotransmitters, growth and differentiation factors, etc.), cell cycle events, environmental or nutritional stresses etc. The appropriate protein kinase functions in signalling pathways to activate or inactivate, for example, a metabolic enzyme, regulatory protein, receptor, cytoskeletal protein, ion channel or pump, or transcription factor. Uncontrolled signalling due to defective control of protein phosphorylation has been implicated in a number of diseases, including, for example, inflammation, allergies, immune diseases, CNS disorders, angiogenesis. Furthermore, it is not surprising that they often become oncogenes, thereby having major implications in multiple cancers, due to their crucial functions in apoptosis, DNA damage repair, proliferation, . . . .

Amongst the families of protein kinases, one particular example is the receptor tyrosine kinase class III family including FLT3. FLT3 (FMS-like tyrosine kinase 3), also referred to as fetal liver kinase-2 (flk-2) or STK-I, is mainly expressed on the surface of hematopoietic stem and progenitor cells, in particular early myeloid and lympoid progenitor cells. It binds to Flt3L to form homodimers which activate signalling involved in proliferation, differentiation and apoptosis of hematopoietic stem and progenitor cells during normal hematopoiesis. Said dimerization results in activation of its tyrosine kinase domain, receptor autophosphorylation and subsequent recruitment of downstream signalling molecules such as the p85 subunit of $PI_3K$ (phosphatidylinositol 3 kinase), PLC-gamma (Phospholipase-C gamma), STAT5a (signal transducer and activator of transcription 5a), and SRC family tyrosine kinases (Gilliland and Griffin, Blood (2002) 100(5), 1532-42; Drexler, Leukemia (1996) 10(4), 588-99 and Ravandi et al., Clin Cancer Res. (2003) 9(2), 535-50). Activation of these downstream signalling molecules by phosphorylation leads to the proliferative and pro-survival effects of FLT3 (Gilliland and Griffin (2002) and Levis and Small, Leukemia (2003) 17(9), 1738-52).

In hematological malignancies, FLT3 is expressed at high levels or FLT3 mutations cause an uncontrolled induction of the FLT3 receptor and downstream molecular pathway. Hematological malignancies include leukemias, lymphomas (non-Hodgkin's lymphoma), Hodgkin's disease (also called Hodgkin's lymphoma), and myeloma- for instance, acute lymphocytic leukemia (ALL), acute myeloid leukemia (AML), acute promyelocytic leukemia (APL), chronic lymphocytic leukemia (CLL), chronic myeloid leukemia (CML), chronic neutrophilic leukemia (CNL), acute undifferentiated leukemia (AUL), anaplastic large-cell lymphoma (ALCL), prolymphocytic leukemia (PML), juvenile myelomonocytic leukemia (JMML), adult T-cell ALL, AML with trilineage myelodysplasia (AML/TMDS), mixed lineage leukemia (MLL), myelodysplastic syndromes (MDSs), myeloproliferative disorders (MPD), multiple myeloma, (MM) and myeloid sarcoma (Kottaridis, P. D., R. E. Gale, et al. (2003). "Flt3 mutations and leukaemia." Br J Haematol 122(4): 523-38). Myeloid sarcoma is also associated with FLT3 mutations (Ansari-Lari, Ali et al. FLT3 mutations in myeloid sarcoma. British Journal of Haematology. 2004 Sep. 126(6):785-91).

Mutations of FLT3 have been detected in about 30% of patients with acute myelogenous leukemia and a small number of patients with acute lymphomatic leukemia or myelodysplastic syndrome. Patients with FLT3 mutations tend to have a poor prognosis, with decreased remission times and disease free survival. There are two known types of activating mutations of FLT3. One is a duplication of 4-40 amino acids in the juxtamembrane region (ITD mutation) of the receptor (25-30% of patients) and the other is a point mutation in the kinase domain (5-7% of patients). These mutations most often involve small tandem duplications of amino acids within the juxtamembrane domain of the receptor and result in tyrosine kinase activity. Expression of a mutant FLT3 receptor in murine marrow cells results in a lethal myeloproliferative syndrome, and preliminary studies (Blood. 2002; 100: 1532-42) suggest that mutant FLT3 cooperates with other leukemia oncogenes to confer a more aggressive phenotype.

Specific inhibitors of FLT3 kinase therefore present an attractive strategy for the treatment of hematopoietic disorders and hematological malignancies. It was as such an object of the present invention to provide compounds and compositions comprising said compounds, acting as inhibitors of receptor tyrosine kinases, in particular as inhibitors of FLT3 (FMS-Related Tyrosine kinase 3).

We have now found that macrocyclic pyrazolopyrimidines can act as kinase inhibitors in particular FLT3 kinase inhibitors.

Several (non-macrocyclic) pyrazolopyrimidines have already been suggested as kinase inhibitors for the treatment of proliferative diseases such as cancer. For example:

WO2007044420: inhibition of CDK—treatment of cancer, . . .

WO2009097446: inhibition of $PI_3$ Kinase—treatment of cancer

WO2010036380: inhibition of $PI_3$ Kinase—treatment of cancer

WO2008037477: inhibition of $PI_3$ Kinase—treatment of proliferative diseases, . . .

WO2006050946: inhibition of c-Abl, c-Src, . . .—treatment of proliferative diseases WO2011003065: inhibition of JAK—treatment of cancer, leukemia, . . .

WO2010119284: inhibition of FGFR kinase—treatment of cancer

However, none of the compounds disclosed in said references have been shown to have FLT3 inhibitory activity. Furthermore, the currently developed FLT3 kinase inhibitors, do not comprise macrocyclic pyrazolopyrimidine moieties (see for example WO2004039782, WO2007048088, WO2008016665, WO2009017795, WO2009109071). The compounds disclosed herein are therefore distinguishable from the prior art compounds in structure, pharmacological activity, potency and kinase selectivity.

SUMMARY OF THE INVENTION

In a first aspect, the present invention provides a compound of Formula I or a stereoisomer, tautomer, racemic, metabolite, pro- or predrug, salt, hydrate, N-oxide form, or solvate thereof,

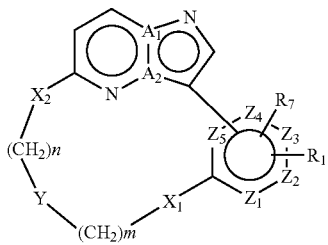

I

Wherein
$A_1$ and $A_2$ are selected from C and N; wherein when $A_1$ is C, then $A_2$ is N; and wherein when $A_2$ is C, then $A_1$ is N;
$R_1$ and $R_7$ are each independently selected from —H, -halo, —OH, —O—$C_{1-6}$alkyl, —S—$C_{1-6}$alkyl, —$NR_9R_{10}$, —(C=O)—$R_4$, —$SO_2$—$R_4$, —CN, —$NR_9$—$SO_2$—$R_4$, —$C_{3-6}$cycloalkyl, and -$Het_6$; wherein each of said $C_{1-6}$alkyl is optionally and independently substituted with from 1 to 3 substituents selected from -halo, —OH, —$NR_{11}R_{12}$, —O—$C_{1-6}$alkyl, and —S—$C_{1-6}$alkyl;
$R_2$ is selected from —H, -halo, —OH, —$C_{1-6}$alkyl, —O—$C_{1-6}$alkyl, —S—$C_{1-6}$alkyl, —(C=O)—$C_{1-6}$alkyl, —(C=O)—$C_{1-6}$alkyl, —(C=O)—$NR_{27}R_{28}$, -$Het_3$, —(C=O)-$Het_3$, —$SO_2$-$C_{1-6}$alkyl, and —$C_{3-6}$cycloalkyl; wherein each of said $C_{1-6}$alkyl is optionally and independently substituted with from 1 to 3 substituents selected from -halo, —OH, —O—$C_{1-6}$alkyl, —S—$C_{1-6}$alkyl, -$Het_3$, —$Ar_2$, and —$NR_{13}R_{14}$;
$R_3$ is selected from —H, -halo, —OH, —$C_{1-6}$alkyl, —O—$C_{1-6}$alkyl, —S—$C_{1-6}$alkyl, —(C=O)—$C_{1-6}$alkyl, —(C=O)—O—$C_{1-6}$alkyl, -$Het_2$, —$C_{3-6}$cycloalkyl —(C=O)-$Het_2$, —(C=O)—$NR_{29}R_{30}$, and —$SO_2$-$C_{1-6}$alkyl; wherein each of said $C_{1-6}$alkyl is optionally and independently substituted with from 1 to 3 substituents selected from -halo, —OH, —O—$C_{1-6}$alkyl, —S—$C_{1-6}$alkyl, —$NR_{15}R_{16}$, -$Het_2$, and —$Ar_3$;
$R_4$ is independently selected from -halo, —OH, —$C_{1-6}$alkyl, —O—$C_{1-6}$alkyl, —S—$C_{1-6}$alkyl, —$NR_{17}R_{18}$, and -$Het_4$;
$R_5$ is selected from —H —$C_{1-6}$alkyl, —$C_{3-6}$cycloalkyl; wherein each of said $C_{1-6}$alkyl is optionally and independently substituted with from 1 to 3 substituents selected from -halo, —OH, —$OC_{1-6}$alkyl, —$SC_{1-6}$alkyl, -$Het_5$, and —$NR_{31}R_{32}$;
$R_6$ is selected from —H, —OH, -halo, —$C_{1-6}$alkyl, —O—$C_{1-6}$alkyl, —S—$C_{1-6}$alkyl, —$NR_{33}R_{34}$, and -$Het_8$;
$R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$, $R_{24}$, $R_{25}$, $R_{26}$, $R_{27}$, $R_{28}$, $R_{29}$, $R_{30}$, $R_{31}$, $R_{32}$, $R_{33}$, $R_{34}$ are each independently selected from —H, —O, —$C_{1-6}$alkyl, and $Het_1$; wherein each of said $C_{1-6}$alkyl is optionally and independently substituted with from 1 to 3 substituents selected from -halo, —OH, —O—$C_{1-6}$alkyl, —S—$C_{1-6}$alkyl, —$NR_{35}R_{36}$, -$Het_7$, and —$Ar_4$;
$R_{35}$ and $R_{36}$ are each independently selected from —H, —O, and $C_{1-6}$alkyl; wherein each of said $C_{1-6}$alkyl is optionally and independently substituted with from 1 to 3 substituents selected from -halo, —OH, —O—$C_{1-6}$alkyl, and —S—$C_{1-6}$alkyl;
$X_1$ is selected from —$C_{1-6}$alkyl-, —O—$C_{1-6}$alkyl-, —S—$C_{1-6}$alkyl-, —(C=O)—, —$NR_3$—(C=O)—, —$C_{1-6}$alkyl-$NR_3$—(C=O)—, —$NR_3$—(C=O)—$NR_{35}$—, —$NR_3$—$C_{1-6}$alkyl-, —$NR_3$—, and —$NR_3$—$SO_2$—; wherein each of said $C_{1-6}$alkyl is optionally and independently substituted with from 1 to 3 substituents selected from -halo, —OH, —$C_{1-6}$alkyl, —O—$C_{1-6}$alkyl, —S—$C_{1-6}$alkyl, and —$NR_{23}R_{24}$;
$X_2$ is selected from —$C_{1-6}$alkyl-, —O—$C_{1-6}$alkyl-, —S—$C_{1-6}$alkyl-, —(C=O)—, —$NR_2$—(C=O)—, —$NR_2$—$C_{1-6}$alkyl-, —$NR_2$—, and —$SO_2$—$NR_2$—; wherein each of said $C_{1-6}$alkyl is optionally and independently substituted with from 1 to 3 substituents selected from -halo, —OH, —$C_{1-6}$alkyl, —O—$C_{1-6}$alkyl, —S—$C_{1-6}$alkyl, and —$NR_{25}R_{26}$;
Y is selected from a direct bond, —$CHR_6$—, —O—, —S—, and —$NR_5$—;
$Ar_2$, $Ar_3$, and $Ar_4$ are each independently a 5- or 6-membered aromatic heterocycle optionally comprising 1 or 2 heteroatoms selected from O, N and S; wherein each of said $Ar_2$, $Ar_3$, and $Ar_4$ is optionally and independently substituted with from 1 to 3 substituents selected from —$NR_{19}R_{20}$, —$C_{1-6}$alkyl, —O—$C_{1-6}$alkyl, and —S—$C_{1-6}$alkyl;
$Het_1$, $Het_2$, $Het_3$, $Het_4$, $Het_5$, $Het_6$, $Het_7$ and $Het_8$ are each independently a 5- or 6-membered monocyclic heterocycle having from 1 to 3 heteroatoms selected from O, N and S, wherein each heterocycle is optionally substituted with from 1 to 3 substituents selected from —$C_{1-6}$alkyl, —$OC_{1-6}$alkyl, —$SC_{1-6}$alkyl, and —$NR_{21}R_{22}$; wherein each of said $C_{1-6}$alkyl is optionally and independently substituted with from 1 to 3 -halo;
$Z_1$, $Z_2$, $Z_3$, $Z_4$ and $Z_5$ are each independently selected from C and N;
m and n are each independently 1, 2, 3, or 4.

In a specific embodiment, the present invention provides a compound as defined herein, wherein
$A_1$ and $A_2$ are selected from C and N; wherein when $A_1$ is C, then $A_2$ is N; and wherein when $A_2$ is C, then $A_1$ is N;
$R_1$ is selected from —H, -halo, —OH, —$C_{1-6}$alkyl, —O—$C_{1-6}$alkyl, —$NR_9R_{10}$, —(C=O)—$R_4$, —CN, —$NR_9$—$SO_2$—$R_4$, and -$Het_6$; wherein each of said $C_{1-6}$alkyl is optionally and independently substituted with from 1 to 3 substituents selected from -halo, —OH, and —$NR_{11}R_{12}$;
$R_7$ is selected from —H, and -halo;
$R_2$ is selected from —H, —$C_{1-6}$alkyl, —(C=O)—$NR_{27}R_{28}$, —(C=O)-$Het_3$, and —$SO_2$—$C_{1-6}$alkyl; wherein each of said $C_{1-6}$alkyl is optionally and independently substituted with from 1 to 3 substituents selected from -halo, —OH, —O—$C_{1-6}$alkyl, -$Het_3$, and —$NR_{13}R_{14}$;
$R_3$ is selected from —H, —$C_{1-6}$alkyl, —(C=O)—$C_{1-6}$alkyl, —(C=O)-$Het_2$, —(C=O)—$NR_{29}R_{30}$, and —$SO_2$—$C_{1-6}$alkyl; wherein each of said $C_{1-6}$alkyl is optionally and independently substituted with from 1 to 3 substituents selected from -halo, —OH, and —O—$C_{1-6}$alkyl;
$R_4$ is independently selected from —OH, —O—$C_{1-6}$alkyl, —$NR_{17}R_{18}$, and -$Het_4$;
$R_5$ is selected from —H, —$C_{1-6}$alkyl, and —$C_{3-6}$cycloalkyl; wherein each of said $C_{1-6}$alkyl is optionally and independently substituted with from 1 to 3 substituents selected from -halo, —OH, —$OC_{1-6}$alkyl, -$Het_5$, and —$NR_{31}R_{32}$;
$R_6$ is selected from —OH, and —$NR_{33}R_{34}$;
$R_9$, $R_{10}$, $R_{11}$, $R_{12}$, $R_{13}$, $R_{14}$, $R_{17}$, $R_{18}$, $R_{27}$, $R_{28}$, $R_{29}$, $R_{30}$, $R_{31}$, $R_{32}$, $R_{33}$, $R_{34}$ are each independently selected from —H, —$C_{1-6}$alkyl, —$NR_{36}R_{36}$ or $Het_1$; wherein each of said $C_{1-6}$alkyl is optionally and independently substituted with from 1 to 3 substituents selected from -halo, —OH, and -Het$_7$;

$R_{35}$ and $R_{36}$ are each independently selected from —H, —O, and $C_{1-6}$alkyl; wherein each of said $C_{1-6}$alkyl is optionally and independently substituted with from 1 to 3 substituents selected from -halo, —OH, —O—$C_{1-6}$alkyl, and —S—$C_{1-6}$alkyl;

$X_1$ is selected from —$C_{1-6}$alkyl-, —O—$C_{1-6}$alkyl-, —S—$C_{1-6}$alkyl-, —(C=O)—, —NR$_3$—(C=O)—, —$C_{1-6}$alkyl-NR$_3$—(C=O)—, —NR$_3$—(C=O)—NR$_{35}$—, —NR$_3$—$C_{1-6}$alkyl-, and —NR$_3$—SO$_2$—;

$X_2$ is selected from —$C_{1-6}$alkyl-, —O—$C_{1-6}$alkyl-, —(C=O)—NR$_2$—, and —NR$_2$—$C_{1-6}$alkyl-;

Y is selected from a direct bond, —CHR$_6$—, —O—, —S—, and —NR$_5$—;

Het$_1$, Het$_2$, Het$_3$, Het$_4$, Het$_5$, Het$_6$, and Het$_7$ are each independently a 5- or 6-membered monocyclic heterocycle having from 1 to 3 heteroatoms selected from O, N and S, wherein each heterocycle is being optionally substituted with from 1 to 3 —$C_{1-6}$alkyl; each of said $C_{1-6}$alkyl being optionally and independently substituted with from 1 to 3 -halo $Z_1$, $Z_2$, $Z_3$, $Z_4$ and $Z_5$ are each independently selected from C and N;

m and n are each independently 1, 2, 3, or 4.

In another specific embodiment, the present invention provides a compound as defined herein wherein, $A_1$ and $A_2$ are selected from C and N; wherein when $A_1$ is C, then $A_2$ is N; and wherein when $A_2$ is C, then $A_1$ is N;

$R_1$ is selected from —H, -halo, —OH, —$C_{1-2}$alkyl, —O—$C_{1-2}$alkyl, —NR$_9$R$_{10}$, —(C=O)—R$_4$, —CN, —NR$_9$—SO$_2$—R$_4$, and -Het$_6$; wherein each of said $C_{1-2}$alkyl is optionally and independently substituted with from 1 to 3 substituents selected from -halo, —OH, and —NR$_{11}$R$_{12}$;

$R_7$ is selected from —H, and -halo;

$R_2$ is selected from —H, —$C_{1-3}$alkyl, —(C=O)—NR$_{27}$R$_{28}$, —(C=O)-Het$_3$, and —SO$_2$—$C_{1-3}$alkyl; wherein each of said $C_{1-3}$alkyl is optionally and independently substituted with from 1 to 3 substituents selected from -halo, —OH, —O—CH$_3$, -Het$_3$, and —NR$_{13}$R$_{14}$;

$R_3$ is selected from —H, —$C_{1-2}$alkyl, —(C=O)—$C_{1-2}$alkyl, —(C=O)-Het$_2$, —(C=O)—NR$_{29}$R$_{30}$, and —SO$_2$—$C_{1-2}$alkyl; wherein each of said $C_{1-2}$alkyl is optionally and independently substituted with from 1 to 3 substituents selected from -halo, —OH, and —O—CH$_3$;

$R_4$ is selected from —OH, —O—CH$_3$, —NR$_{17}$R$_{18}$, and -Het$_4$;

$R_5$ is selected from —H —$C_{1-3}$alkyl, and —$C_{3-6}$cycloalkyl; wherein each of said $C_{1-3}$alkyl is optionally and independently substituted with from 1 to 3 substituents selected from -halo, —OH, —OCH$_3$, -Het$_5$, and —NR$_{31}$R$_{32}$;

$R_6$ is selected from —OH, and —NR$_{33}$R$_{34}$;

$R_9$, $R_{10}$, $R_{11}$, $R_{12}$, $R_{13}$, $R_{14}$, $R_{31}$, $R_{32}$, $R_{33}$, and $R_{34}$ are each independently selected from —H and —CH$_3$;

$R_{17}$, $R_{18}$, $R_{27}$, and $R_{28}$ are each independently selected from —H and —$C_{1-2}$alkyl, each of said —$C_{1-2}$alkyl being optionally and independently substituted with from 1 to 3 substituents selected from —OH, -halo —NR$_{35}$R$_{36}$ and -Het$_7$ $R_{29}$ and $R_{30}$, are each independently selected from —H, —OH and —OCH$_3$;

$R_{35}$ and $R_{36}$ are each independently selected from —H, —O, and $C_{1-6}$alkyl; wherein each of said $C_{1-6}$alkyl is optionally and independently substituted with from 1 to 3 substituents selected from -halo, —OH, —O—$C_{1-6}$alkyl, and —S—$C_{1-6}$alkyl;

$X_1$ is selected from —$C_{1-6}$alkyl-, —O—$C_{1-6}$alkyl-, —(C=O)—, —S—$C_{1-6}$alkyl-, —NR$_3$—(C=O)—, —$C_{1-6}$alkyl-NR$_3$—(C=O)—, —NR$_3$—(C=O)—NR$_{35}$—, —NR$_3$—$C_{1-6}$alkyl-, and —NR$_3$—SO$_2$-$C_{1-6}$alkyl-;

$X_2$ is selected from —$C_{1-6}$alkyl-, —O—$C_{1-6}$alkyl-, —(C=O)—NR$_2$—, and —NR$_2$—$C_{1-6}$alkyl-;

Y is selected from a direct bond, —CHR$_6$—, —O—, —S—, and —NR$_5$—;

Het$_1$ is selected from -piperidinyl and -piperazinyl; each of said Het$_1$ being substituted with $C_{1-2}$alkyl; each of said $C_{1-2}$alkyl being optionally and independently substituted with from 1 to 3-halo;

Het$_2$ is -piperidinyl-CH$_3$;

Het$_3$ is selected from -piperazinyl, and -morpholinyl;

Het$_4$, is selected from -piperazinyl, and -morpholinyl; each of said Het$_4$ being optionally and independently substituted with $C_{1-2}$alkyl; each of said $C_{1-2}$alkyl being optionally and independently substituted with from 1 to 3 -halo;

Het$_5$ is -morpholinyl;

Het$_6$, is -piperazinyl;

Het$_7$ is -pyrrolidinyl;

$Z_1$, $Z_2$, $Z_3$, $Z_4$ and $Z_5$ are each independently selected from C and N;

m and n are each independently 1, 2, 3, or 4.

In yet a further embodiment, the present invention provides a compound a defined herein, wherein $A_1$ and $A_2$ are selected from C and N; wherein when $A_1$ is C, than $A_2$ is N; and wherein when $A_2$ is C, than $A_1$ is N;

$R_1$ is selected from —H, -halo, —$C_{1-6}$alkyl, —OC$_{1-6}$alkyl, and —(C=O)—R$_4$; wherein each of said $C_{1-6}$alkyl is optionally and independently substituted with from 1 to 3 -halo;

$R_7$ is —H;

$R_2$ is selected from —H, —$C_{1-6}$alkyl, —(C=O)—O—$C_{1-6}$alkyl, and —(C=O)-Het$_3$; wherein each of said $C_{1-6}$alkyl is optionally and independently substituted with from 1 to 3 substituents selected from —OH, —OC$_{1-6}$alkyl, -Het$_3$, and —NR$_{13}$R$_{14}$;

$R_3$ is selected from —H, —$C_{1-6}$alkyl, and —(C=O)-Het$_2$; wherein each of said $C_{1-6}$alkyl is optionally and independently substituted with from 1 to 3 substituents —OH;

$R_4$ is selected from —OH, —O—$C_{1-6}$alkyl, —NR$_{17}$R$_{18}$, and -Het$_4$;

$R_5$ is selected from —H, —$C_{1-6}$alkyl, and —$C_{3-6}$cycloalkyl; wherein each of said $C_{1-6}$alkyl is optionally and independently substituted with from 1 to 3 substituents selected from —OH, and -Het$_5$;

$R_{13}$, $R_{14}$, $R_{17}$, $R_{18}$, $R_{19}$ and $R_{20}$ are each independently selected from —H, —O, —$C_{1-6}$alkyl, and Het$_1$;

$X_1$ is selected from —$C_{1-6}$alkyl-, —O—$C_{1-6}$alkyl-, —NR$_3$—(C=O)—, —$C_{1-6}$alkyl-NR$_3$—(C=O)—, and —NR$_3$—$C_{1-6}$alkyl-;

$X_2$ is selected from —O—$C_{1-6}$alkyl-, —(C=O)—NR$_2$—, and —NR$_2$—$C_{1-6}$alkyl-;

Y is selected from a direct bond, —O—, —S—, and —NR$_5$—;

Het$_1$, Het$_2$, Het$_3$, Het$_4$ and Het$_5$ are each independently a 5- or 6-membered monocyclic heterocycle having from 1 to 3 heteroatoms selected from O, N and S, wherein each heterocycle is being optionally substituted with from 1 to 3 —$C_{1-6}$alkyl;

$Z_1$, $Z_2$, $Z_3$, $Z_4$ and $Z_5$ are each independently selected from C and N;

m and n are each independently 1, 2, 3, or 4.

In another specific embodiment, the present invention provides a compound as defined herein, wherein $A_1$ and $A_2$ are selected from C and N; wherein when $A_1$ is C, than $A_2$ is N; and wherein when $A_2$ is C, than $A_1$ is N $R_1$ is selected from —H, -halo, —$CF_3$, —$OC_{1-6}$alkyl, and —(C=O)—$R_4$;

$R_7$ is —H;

$R_2$ is selected from —H, —$C_{1-6}$alkyl, —(C=O)—O—$C_{1-6}$alkyl, and —(C=O)-$Het_3$; wherein each of said $C_{1-6}$alkyl is optionally and independently substituted with from 1 to 3 substituents selected from —OH, —$OC_{1-6}$alkyl, -$Het_3$, and —$NR_{13}R_{14}$;

$R_3$ is selected from —H, —$C_{1-6}$alkyl, and —(C=O)-$Het_2$; wherein each of said $C_{1-6}$alkyl is optionally and independently substituted with from 1 to 3 —OH;

$R_4$ is selected from —OH, —$OC_{1-6}$alkyl, —$NR_{17}R_{18}$, and -$Het_4$;

$R_5$ is selected from —H, —$C_{1-6}$alkyl, —$C_{3-6}$cycloalkyl; wherein each of said $C_{1-6}$alkyl is optionally and independently substituted with from 1 to 3 substituents selected from —OH, and -$Het_5$;

$R_{13}$ and $R_{14}$ are each independently selected from —H, and —$C_{1-6}$alkyl;

$R_{17}$ and $R_{18}$ are each independently selected from —H, —$C_{1-6}$alkyl, and -$Het_1$:

$R_{19}$ and $R_{20}$ are each independently selected from —O, and —$C_{1-6}$alkyl;

$X_1$ is selected from —$C_{1-6}$alkyl-, —O—$C_{1-6}$alkyl-, —$NR_3$—(C=O)—, —$C_{1-6}$alkyl-$NR_3$—(C=O)—, and —$NR_3$—$C_{1-6}$alkyl-;

$X_2$ is selected from —O—$C_{1-6}$alkyl-, —(C=O)—$NR_2$—, and —$NR_2$—$C_{1-6}$alkyl-;

Y is selected from a direct bond, —O—, —S—, and —$NR_5$—;

$Het_1$, $Het_2$, $Het_3$, $Het_4$ and $Het_5$ are each independently selected from -morpholinyl, -piperidinyl, -piperazinyl, and pyrrolidinyl, wherein each heterocycle is optionally substituted with from 1 to 3 —$C_{1-6}$alkyl;

$Z_1$, $Z_2$, $Z_3$, $Z_4$ and $Z_5$ are each independently selected from C and N m and n are each independently 1, 2, 3, or 4.

In yet a further embodiment, the present invention provides a compound according to this invention, wherein $A_1$ and $A_2$ are selected from C and N; wherein when $A_1$ is C, than $A_2$ is N; and wherein when $A_2$ is C, than $A_1$ is N $R_1$ is selected from —H, -halo, —$CF_3$, —$OCH_3$, and —(C=O)—$R_4$;

$R_7$ is —H;

$R_2$ is selected from —H, —$C_{2-4}$alkyl, —(C=O)—O—$C_{2-4}$alkyl, and —(C=O)-$Het_3$; wherein each of said $C_{2-4}$alkyl is optionally and independently substituted with from 1 to 3 substituents selected from —OH, —$OCH_3$, -$Het_3$, and —$NR_{13}R_{14}$;

$R_3$ is selected from —H, —$C_{1-2}$alkyl, and —(C=O)-$Het_2$; wherein each of said $C_{1-2}$alkyl is optionally and independently substituted with from 1 to 3 —OH;

$R_4$ is selected from —OH, —$OCH_3$, —$NR_{17}R_{18}$, and -$Het_4$;

$R_5$ is selected from —H, —$C_{1-3}$alkyl, and —$C_{3-6}$cycloalkyl; wherein each $C_{1-3}$alkyl is optionally substituted with from 1 to 3 substituents selected from —OH, and -$Het_5$;

$R_{13}$ and $R_{14}$ are —$CH_3$;

$R_{17}$ and $R_{18}$ are each independently selected from —H, —$CH_3$, and -$Het_1$;

$R_{19}$ and $R_{20}$ are each —O;

$X_1$ is selected from —$C_{1-6}$alkyl-, —O—$C_{2-6}$alkyl-, —$NR_3$—(C=O)—, —$C_{1-6}$alkyl-$NR_3$—(C=O)—, and —$NR_3$—$C_{2-3}$alkyl-;

$X_2$ is selected from —O—$C_2$alkyl-, —(C=O)—$NR_2$—, and —$NR_2$—$C_{1-3}$alkyl-;

Y is selected from a direct bond, —O—, —S—, and —$NR_5$—;

$Het_1$, $Het_2$, $Het_3$, $Het_4$ and $Het_5$ are each independently selected from -morpholinyl, -piperidinyl, -piperazinyl, and pyrrolidinyl, wherein each heterocycle is optionally substituted with from 1 to 3 —$CH_3$;

$Z_1$, $Z_2$, $Z_3$, $Z_4$ and $Z_5$ are each independently selected from C and N m and n are each independently 1, 2, 3, or 4.

In a further specific embodiment, the invention provides a compound as defined herein, wherein $A_1$ and $A_2$ are selected from C and N; wherein when $A_1$ is C, than $A_2$ is N; and wherein when $A_2$ is C, than $A_1$ is N;

$R_1$ is selected from —H, -halo, —$CF_3$, —$OCH_3$, —(C=O)—OH, —(C=O)—$OCH_3$, —(C=O)-$Het_4$, —(C=O)—NH-$Het_4$, —(C=O)—$NH_2$, and —(C=O)—NH—$CH_3$;

$R_7$ is —H;

$R_2$ is selected from —H, —$C_{2-4}$alkyl, —(C=O)—O—$C_2$alkyl, and —(C=O)-$Het_3$; wherein each $C_{2-4}$alkyl is optionally and independently substituted with 1 substituent selected from —OH, —$OCH_3$, -$Het_3$, and —$NR_{13}R_{14}$;

$R_3$ is selected from —H, —$C_{1-2}$alkyl, and —(C=O)-$Het_2$; wherein said $C_{1-2}$alkyl is optionally and independently substituted with 1 —OH;

$R_5$ is selected from —H, —$C_{1-3}$alkyl, and —$C_{3-6}$cycloalkyl; wherein each $C_{1-3}$alkyl is optionally and independently substituted with 1 to 3 substituents selected from —OH, and -$Het_5$;

$R_{13}$ and $R_{14}$ are —$CH_3$;

$X_1$ is selected from —$C_{1-6}$alkyl-, —O—$C_{2-6}$alkyl-, —$NR_3$—(C=O)—, —$C_{1-6}$alkyl-$NR_3$—(C=O)—, and —$NR_3$—$C_2$alkyl-;

$X_2$ is selected from —O—$C_2$alkyl-, —(C=O)—$NR_2$—, and —$NR_2$—$C_{1-3}$alkyl-;

Y is selected from a direct bond, —O—, —S—, and —$NR_5$—;

$Ar_3$ is phenyl substituted with —$NO_2$;

$Het_2$ is -piperidinyl substituted with —$CH_3$;

$Het_3$ is selected from -morpholinyl, and -piperazinyl;

$Het_4$ is selected from -morpholinyl, -piperidinyl, and -piperazinyl; wherein said -piperidinyl and -piperazinyl are substituted with —$CH_3$;

$Het_5$ is selected from -morpholinyl, and -pyrrolidinyl;

$Z_1$, $Z_2$, $Z_3$, $Z_4$ and $Z_5$ are each independently selected from C and N m and n are each independently 1, 2, 3, or 4.

The invention further provides a compound as defined herein, wherein $A_1$ and $A_2$ are selected from C and N; wherein when $A_1$ is C, then $A_2$ is N; and wherein when $A_2$ is C, then $A_1$ is N;

$R_1$ and $R_7$ are each independently selected from —H, -halo, —$C_{1-6}$alkyl, —O—$C_{1-6}$alkyl, and —(C=O)—$R_4$; wherein each of said $C_{1-6}$alkyl is optionally and independently substituted with from 1 to 3 substituents selected from -halo, and —OH;

$R_2$ is selected from —H, —$C_{1-6}$alkyl, —(C=O)—$NR_{27}R_{28}$, and —(C=O)-$Het_3$; wherein each of said $C_{1-6}$alkyl is optionally and independently substituted with from 1 to 3 substituents selected from -halo, —OH, and —$NR_{13}R_{14}$;

$R_3$ is selected from —H, —$C_{1-6}$alkyl, and —(C=O)-$Het_2$; wherein each of said $C_{1-6}$alkyl is optionally and independently substituted with —OH;

$R_4$ is independently selected from —OH, and —$NR_{17}R_{18}$;

$R_5$ is selected from —H —$C_{1-6}$alkyl, and —$C_{3-6}$cycloalkyl; wherein each of said $C_{1-6}$alkyl is optionally and independently substituted with from 1 to 3 substituents selected from -halo, —OH, —$OC_{1-6}$alkyl, -$Het_5$, and —$NR_{31}R_{32}$;

$R_{13}$, $R_{14}$, $R_{17}$, $R_{18}$, $R_{27}$, $R_{28}$, $R_{31}$, $R_{32}$ are each independently selected from —H, and —$C_{1-6}$alkyl; wherein each of said $C_{1-6}$alkyl is optionally and independently substituted with from 1 to 3 substituents selected from -halo, —$NR_{35}R_{36}$, and -$Het_7$;

$R_{35}$ and $R_{36}$ are each —$C_{1-6}$alkyl;

$X_1$ is selected from —O—$C_{1-6}$alkyl-, —(C=O)—, —$NR_3$—(C=O)—, —$C_{1-6}$alkyl-$NR_3$—(C=O)—, and —$NR_3$—;

$X_2$ is selected from —O—$C_{1-6}$alkyl-, and —$NR_2$—;

Y is selected from a direct bond, —O—, and —$NR_5$—;

$Het_3$ is -piperazinyl $Het_2$ is -piperidinyl substituted with —$CH_3$;

$Het_5$ is selected from -morpholinyl and -pyrrolidinyl;

$Het_7$ is -pyrrolidinyl;

$Z_1$, $Z_2$, $Z_3$, $Z_4$ and $Z_5$ are each independently selected from C and N;

m and n are each independently 1, 2, 3, or 4.

In a preferred embodiment, the present invention provides a compound as defined herein, wherein $A_1$ is N; and $A_2$ is C;

$R_1$ and $R_7$ are each independently selected from —H, —$C_{1-6}$alkyl, —O—$C_{1-6}$alkyl, and —(C=O)—$R_4$; wherein each of said $C_{1-6}$alkyl is optionally and independently substituted with from 1 to 3 substituents selected from -halo, and —OH;

$R_2$ is selected from —H, —$C_{1-6}$alkyl, —(C=O)—$NR_{27}R_{28}$; wherein each of said $C_{1-6}$alkyl is optionally and independently substituted with from 1 to 3 substituents selected from —OH;

$R_3$ is selected from —H, —$C_{1-6}$alkyl, and —(C=O)-$Het_2$; wherein each of said $C_{1-6}$alkyl is optionally and independently substituted with —OH;

$R_4$ is independently selected from —OH, and —$NR_{17}R_{18}$;

$R_5$ is selected from —H —$C_{1-6}$alkyl, and —$C_{3-6}$cycloalkyl; wherein each of said $C_{1-6}$alkyl is optionally and independently substituted with from 1 to 3 substituents selected from -halo, —OH, —$OC_{1-6}$alkyl, and -$Het_5$;

$R_{17}$, $R_{18}$, $R_{27}$, and $R_{28}$ are each independently selected from —H, and —$C_{1-6}$alkyl; wherein each of said $C_{1-6}$alkyl is optionally and independently substituted with from 1 to 3 substituents selected from —$NR_{35}R_{36}$, and -$Het_7$;

$R_{35}$ and $R_{36}$ are each —$C_{1-6}$alkyl;

$X_1$ is selected from —O—$C_{1-6}$alkyl-, —$NR_3$—(C=O)—, and —$NR_3$—;

$X_2$ is selected from —O—$C_{1-6}$alkyl-, and —$NR_2$—;

Y is selected from a direct bond, —O—, and —$NR_5$—;

$Het_2$ is -piperidinyl substituted with —$CH_3$;

$Het_5$ is selected from -morpholinyl and -pyrrolidinyl;

$Het_7$ is -pyrrolidinyl;

$Z_1$, $Z_2$, $Z_3$, $Z_4$ and $Z_5$ are each C;

m and n are each independently 1, 2, 3, or 4.

In another preferred embodiment, the present invention provides a compound as defined herein, wherein $A_1$ is N; and $A_2$ is C;

$R_1$ and $R_7$ are each —H;

$R_2$ is selected from —H, —(C=O)—$NR_{27}R_{28}$ and —$C_{1-6}$alkyl; wherein each of said $C_{1-6}$alkyl is optionally and independently substituted with from 1 to 3 —OH;

$R_5$ is selected from —H and —$C_{1-6}$alkyl; wherein each of said $C_{1-6}$alkyl is optionally and independently substituted with from 1 to 3 -$Het_5$;

$R_{27}$, and $R_{28}$ are each independently selected from —H, and —$C_{1-6}$alkyl; wherein each of said $C_{1-6}$alkyl is optionally and independently substituted with from 1 to 3 substituents selected from —$NR_{35}R_{36}$, and -$Het_7$;

$R_{35}$ and $R_{36}$ are each —$C_{1-6}$alkyl;

$X_1$ is selected from —O—$CH_2$—;

$X_2$ is selected from —O—$CH_2$—, and —$NR_2$—;

Y is —$NR_5$—;

$Het_5$ is selected from -morpholinyl and -pyrrolidinyl;

$Het_7$ is -pyrrolidinyl;

$Z_1$, $Z_2$, $Z_3$, $Z_4$ and $Z_5$ are each C;

m is 1; and n is selected from 1, 2 and 3.

In a particular embodiment, the present invention provides a compound selected from the list comprising:

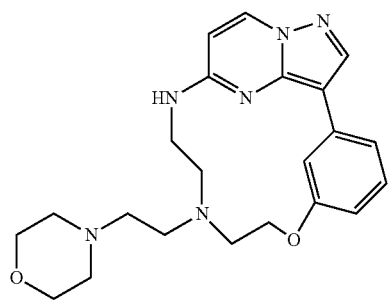

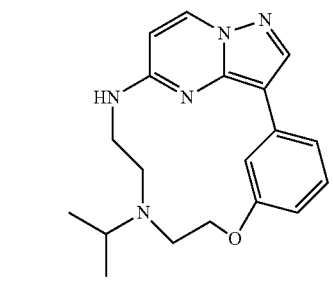

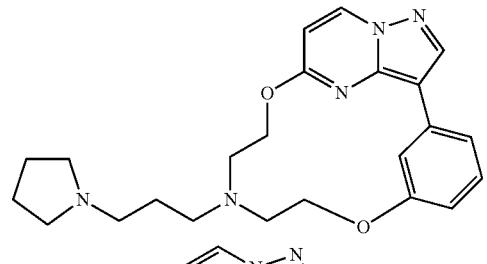

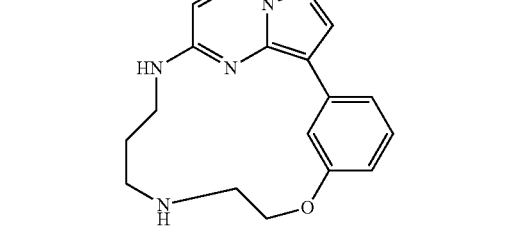

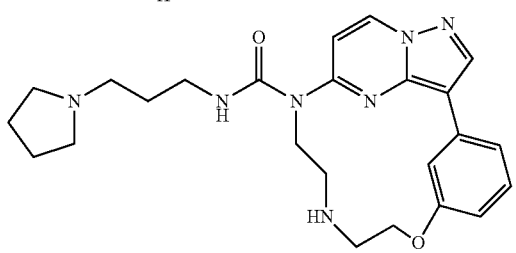

-continued

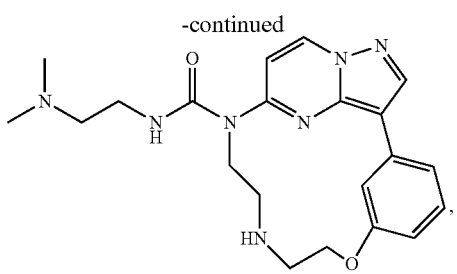

more in particular

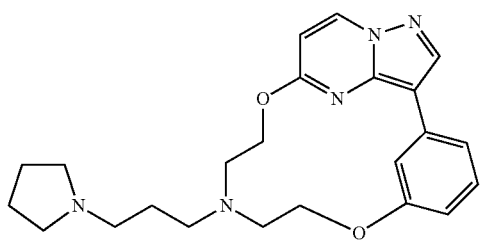 [SMILES: c1cc2cc(c1)-c1cnn3ccc(nc13)OCCN(CCCN1CCCC1)CCO2]

In a preferred embodiment, the present invention provides a compound as defined herein above, wherein the pyrazolopyrimidine moiety is linked to the aryl or heteroaryl moiety at position $Z_4$ and wherein $R_7$ is linked to the aryl or heteroaryl moiety at position $Z_5$ in accordance with Formula I.

In a further aspect, the present invention provides a compound according to this invention for use as a human or veterinary medicine. More in particular, it provides the use of a compound according to this invention for the manufacture of a medicament for the treatment of cell proliferative disorders, such as cancer.

The present invention further provides a pharmaceutical composition comprising a compound according to this invention, suitable for use as a human or veterinary medicine.

In yet a further aspect, the present invention provides the use of a compound or a composition according to this invention, suitable for inhibiting the activity of a kinase; in particular a FLT3 kinase.

It further provides the use of a compound or a composition according to this invention for the prevention and/or or treatment of cell proliferative disorders, such as cancer.

In a further aspect, the present invention provides a method for the prevention and/or treatment of cell proliferative disorders such as cancer; said method comprising administering to a subject in need thereof a compound or a composition according to this invention.

DETAILED DESCRIPTION OF THE INVENTION

The present invention will now be further described. In the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

Unless a context dictates otherwise, asterisks are used herein to indicate the point at which a mono- or bivalent radical depicted is connected to the structure to which it relates and of which the radical forms part.

As already mentioned hereinbefore, in a first aspect the present invention provides compounds of Formula I, or a stereoisomer, tautomer, racemic, metabolite, pro- or predrug, salt, hydrate, N-oxide form, or solvate thereof,

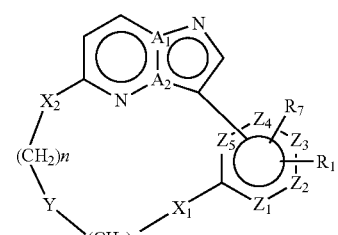

I wherein
$A_1$ and $A_2$ are selected from C and N; wherein when $A_1$ is C, then $A_2$ is N; and wherein when $A_2$ is C, then $A_1$ is N;
$R_1$ and $R_7$ are each independently selected from —H, -halo, —OH, —$C_{1-6}$alkyl, —O—$C_{1-6}$alkyl, —S—$C_{1-6}$alkyl, —$NR_9R_{10}$, —(C=O)—$R_4$, —$SO_2$—$R_4$, —CN, —$NR_9$—$SO_2$—$R_4$, —$C_{3-6}$cycloalkyl, and -$Het_6$; wherein each of said $C_{1-6}$alkyl is optionally and independently substituted with from 1 to 3 substituents selected from -halo, —OH, —$NR_{11}R_{12}$, —O—$C_{1-6}$alkyl, and —S—$C_{1-6}$alkyl;
$R_2$ is selected from —H, -halo, —OH, —$C_{1-6}$alkyl, —O—$C_{1-6}$alkyl, —S—$C_{1-6}$alkyl, —(C=O)—$C_{1-6}$alkyl, —(C=O)—O—$C_{1-6}$alkyl, —(C=O)—$NR_{27}R_{28}$, -$Het_3$, —(C=O)-$Het_3$, —$SO_2$—$C_{1-6}$alkyl, and —$C_{3-6}$cycloalkyl; wherein each of said $C_{1-6}$alkyl is optionally and independently substituted with from 1 to 3 substituents selected from -halo, —OH, —O—$C_{1-6}$alkyl, —S—$C_{1-6}$alkyl, -$Het_3$, —$Ar_2$, and —$N_{13}R_{14}$;
$R_3$ and $R_{35}$ are each independently selected from —H, -halo, —OH, —$C_{1-6}$alkyl, —O—$C_{1-6}$alkyl, —S—$C_{1-6}$alkyl, —(C=O)—$C_{1-6}$alkyl, —(C=O)—O—$C_{1-6}$alkyl, -$Het_2$, —$C_{3-6}$cycloalkyl —(C=O)-$Het_2$, —(C=O)—$NR_{29}R_{30}$, and —$SO_2$—$C_{1-6}$alkyl; wherein each of said $C_{1-6}$alkyl is optionally and independently substituted with from 1 to 3 substituents selected from -halo, —OH, —O—$C_{1-6}$alkyl, —S—$C_{1-6}$alkyl, —$NR_{15}R_{16}$, -$Het_2$, and —$Ar_3$;
$R_4$ is independently selected from -halo, —OH, —$C_{1-6}$alkyl, —O—$C_{1-6}$alkyl, —S—$C_{1-6}$alkyl, —$NR_{17}R_{18}$, and -$Het_4$;
$R_5$ is selected from —H —$C_{1-6}$alkyl, —$C_{3-6}$cycloalkyl; wherein each of said $C_{1-6}$alkyl is optionally and independently substituted with from 1 to 3 substituents selected from -halo, —OH, —$OC_{1-6}$alkyl, —$SC_{1-6}$alkyl, -$Het_5$, and —$NR_{31}R_{32}$;
$R_6$ is selected from —H, —OH, -halo, —$C_{1-6}$alkyl, —O—$C_{1-6}$alkyl, —S—$C_{1-6}$alkyl, —$NR_{33}R_{34}$, and -$Het_8$;
$R_9, R_{10}, R_{11}, R_{12}, R_{13}, R_{14}, R_{15}, R_{16}, R_{17}, R_{18}, R_{19}, R_{20}, R_{21}, R_{22}, R_{23}, R_{24}, R_{25}, R_{26}, R_{27}, R_{28}, R_{29}, R_{30}, R_{31}, R_{32}, R_{33}, R_{34}$ are each independently selected from —H, —O, —$C_{1-6}$alkyl, and $Het_1$; wherein each of said $C_{1-6}$alkyl is optionally and independently substituted with from 1 to 3 substituents selected from -halo, —OH, —O—$C_{1-6}$alkyl, —S—$C_{1-6}$alkyl, —$NR_{35}R_{36}$, -$Het_7$, and —$Ar_4$;
$R_{35}$ and $R_{36}$ are each independently selected from —H, —O, and $C_{1-6}$alkyl; wherein each of said $C_{1-6}$alkyl is optionally and independently substituted with from 1 to 3 substituents selected from -halo, —OH, —O—$C_{1-6}$alkyl, and —S—$C_{1-6}$alkyl;
$X_1$ is selected from —$C_{1-6}$alkyl-, —O—$C_{1-6}$alkyl-, —S—$C_{1-6}$alkyl-, —(C=O)—, —$NR_3$—(C=O)—, —$C_{1-6}$ alkyl-NR$_3$—(C=O)—, —NR$_3$—(C=O)—NR$_{35}$—, —NR$_3$—C$_{1-6}$alkyl-, —NR$_3$—, and —NR$_3$—SO$_2$—; wherein each of said C$_{1-6}$alkyl is optionally and independently substituted with from 1 to 3 substituents selected from -halo, —OH, —C$_{1-6}$alkyl, —O—C$_{1-6}$alkyl, —S—C$_{1-6}$alkyl, and —NR$_{23}$R$_{24}$;

X$_2$ is selected from —C$_{1-6}$alkyl-, —O—C$_{1-6}$alkyl-, —S—C$_{1-6}$alkyl-, —(C=O)—, —NR$_2$—(C=O)—, —NR$_2$—C$_{1-6}$alkyl-, —NR$_2$—, and —SO$_2$—NR$_2$—; wherein each of said C$_{1-6}$alkyl is optionally and independently substituted with from 1 to 3 substituents selected from -halo, —OH, —C$_{1-6}$alkyl, —O—C$_{1-6}$alkyl, —S—C$_{1-6}$alkyl, and —NR$_{25}$R$_{26}$;

Y is selected from a direct bond, —CHR$_6$—, —O—, —S—, and —NR$_5$—;

Ar$_2$, Ar$_3$, and Ar$_4$ are each independently a 5- or 6-membered aromatic heterocycle optionally comprising 1 or 2 heteroatoms selected from O, N and S; wherein each of said Ar$_2$, Ar$_3$, and Ar$_4$ is optionally and independently substituted with from 1 to 3 substituents selected from —NR$_{19}$R$_{20}$, —C$_{1-6}$alkyl, —O—C$_{1-6}$alkyl, and —S—C$_{1-6}$alkyl;

Het$_1$, Het$_2$, Het$_3$, Het$_4$, Het$_5$, Het$_6$, Het$_7$ and Het$_8$ are each independently a 5- or 6-membered monocyclic heterocycle having from 1 to 3 heteroatoms selected from O, N and S, wherein each heterocycle is optionally substituted with from 1 to 3 substituents selected from C$_{1-6}$alkyl, —OC$_{1-6}$alkyl, —SC$_{1-6}$alkyl, and —NR$_{21}$R$_{22}$; wherein each of said C$_{1-6}$alkyl is optionally and independently substituted with from 1 to 3 -halo;

Z$_1$, Z$_2$, Z$_3$, Z$_4$ and Z$_5$ are each independently selected from C and N;

m and n are each independently 1, 2, 3, or 4.

When describing the compounds of the invention, the terms used are to be construed in accordance with the following definitions, unless a context dictates otherwise:

The term "alkyl" by itself or as part of another substituent refers to fully saturated hydrocarbon radicals. Generally, alkyl groups of this invention comprise from 1 to 6 carbon atoms. Alkyl groups may be linear or branched and may be substituted as indicated herein. When a subscript is used herein following a carbon atom, the subscript refers to the number of carbon atoms that the named group may contain. Thus, for example, C$_{1-6}$alkyl means an alkyl of one to six carbon atoms. Examples of alkyl groups are methyl, ethyl, n-propyl, i-propyl, butyl, and its isomers (e.g. n-butyl, i-butyl and t-butyl); pentyl and its isomers, hexyl and its isomers. C$_{1-6}$ alkyl includes all linear, branched, or cyclic alkyl groups with between 1 and 6 carbon atoms, and thus includes methyl, ethyl, n-propyl, i-propyl, butyl and its isomers (e.g. n-butyl, i-butyl and t-butyl); pentyl and its isomers, hexyl and its isomers, cyclopentyl, and cyclohexyl.

The term "optionally substituted alkyl" refers to an alkyl group optionally substituted with one or more substituents (for example 1 to 3 substituents, for example 1, 2 or 3 substituents or 1 to 2 substituents) at any available point of attachment. Non-limiting examples of such substituents include -halo, —OH, primary and secondary amides, —O—C$_{1-6}$alkyl, —S—C$_{1-6}$alkyl, heteroaryl, aryl, and the like.

The term "cycloalkyl" by itself or as part of another substituent is a cyclic alkyl group, that is to say, a monovalent, saturated, or unsaturated hydrocarbyl group having a cyclic structure. Cycloalkyl includes all saturated or partially saturated (containing 1 or 2 double bonds) hydrocarbon groups having a cyclic structure. Cycloalkyl groups may comprise 3 or more carbon atoms in the ring and generally, according to this invention comprise from 3 to 6 atoms. Examples of cycloalkyl groups include but are not limited to cyclopropyl, cyclobutyl, cyclopentyl, cyclohexyl.

Where alkyl groups as defined are divalent, i.e., with two single bonds for attachment to two other groups, they are termed "alkylene" groups. Non-limiting examples of alkylene groups includes methylene, ethylene, methylmethylene, trimethylene, propylene, tetramethylene, ethylethylene, 1,2-dimethylethylene, pentamethylene and hexamethylene.

Generally, alkylene groups of this invention preferably comprise the same number of carbon atoms as their alkyl counterparts. Where an alkylene or cycloalkylene biradical is present, connectivity to the molecular structure of which it forms part may be through a common carbon atom or different carbon atom. To illustrate this applying the asterisk nomenclature of this invention, a C$_3$ alkylene group may be for example *—CH$_2$CH$_2$CH$_2$—*, *—CH(—CH$_2$CH$_3$)—*, or *—CH$_2$CH(—CH$_3$)—*. Likewise a C$_3$ cycloalkylene group may be

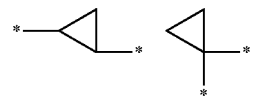

The terms "heterocycle" as used herein by itself or as part of another group refer to non-aromatic, fully saturated or partially unsaturated cyclic groups (for example, 3 to 6 membered monocyclic ring systems) which have at least one heteroatom in at least one carbon atom-containing ring. Each ring of the heterocyclic group containing a heteroatom may have 1, 2, 3 or 4 heteroatoms selected from nitrogen atoms, oxygen atoms and/or sulfur atoms. An optionally substituted heterocyclic refers to a heterocyclic having optionally one or more substituents (for example 1 to 4 substituents, or for example 1, 2, 3 or 4), selected from those defined above for substituted alkyl.

Exemplary heterocyclic groups include piperidinyl, azetidinyl, imidazolinyl, imidazolidinyl, isoxazolinyl, oxazolidinyl, isoxazolidinyl, thiazolidinyl, isothiazolidinyl, piperidyl, succinimidyl, 3H-indolyl, isoindolinyl, chromenyl, isochromanyl, xanthenyl, 2H-pyrrolyl, 1-pyrrolinyl, 2-pyrrolinyl, 3-pyrrolinyl, pyrrolidinyl, 4H-quinolizinyl, 4aH-carbazolyl, 2-oxopiperazinyl, piperazinyl, homopiperazinyl, 2-pyrazolinyl, 3-pyrazolinyl, pyranyl, dihydro-2H-pyranyl, 4H-pyranyl, 3,4-dihydro-2H-pyranyl, phthalazinyl, oxetanyl, thietanyl, 3-dioxolanyl, 1,3-dioxanyl, 2,5-dioximidazolidinyl, 2,2,4-piperidonyl, 2-oxopiperidinyl, 2-oxopyrrolodinyl, 2-oxoazepinyl, indolinyl, tetrahydropyranyl, tetrahydrofuranyl, tetrehydrothienyl, tetrahydroquinolinyl, tetrahydroisoquinolinyl, thiomorpholinyl, thiomorpholinyl sulfoxide, thiomorpholinyl sulfone, 1,3-dioxolanyl, 1,4-oxathianyl, 1,4-dithianyl, 1,3,5-trioxanyl, 6H-1,2,5-thiadiazinyl, 2H-1,5,2-dithiazinyl, 2H-oxocinyl, 1H-pyrrolizinyl, tetrahydro- 1,1-dioxothienyl, N— formylpiperazinyl, and morpholinyl; in particular pyrrolidinyl, imidazolidinyl, pyrazolidinyl, piperidinyl, dioxolanyl, dioxanyl, morpholinyl, thiomorpholinyl, piperazinyl, thiazolidinyl, tetrahydropyranyl, and tetrahydrofuranyl.

The term "aryl" as used herein refers to a polyunsaturated, aromatic hydrocarbyl group having a single ring (i.e. phenyl). Aryl is also intended to include the partially hydrogenated derivatives of the carbocyclic systems enumerated herein. Non-limiting examples of aryl comprise phenyl, biphenylyl, biphenylenyl, 5- or 6-tetralinyl, 1-, 2-, 3-, 4-, 5-, 6-, 7-, or 8-azulenyl, 1- or 2-naphthyl, 1-, 2-, or 3-indenyl, 1-, 2-, or 9-anthryl, 1- 2-, 3-, 4-, or 5-acenaphtylenyl, 3-, 4-, or 5-acenaphtenyl, 1-, 2-, 3-, 4-, or 10-phenanthryl, 1- or 2-pentalenyl, 1, 2-, 3-, or 4-fluorenyl, 4- or 5-indanyl, 5-, 6-, 7-, or 8-tetrahydronaphthyl, 1,2,3,4-tetrahydronaphthyl, 1,4-dihydronaphthyl, dibenzo[a,d]cylcoheptenyl, and 1-, 2-, 3-, 4-, or 5-pyrenyl; in particular phenyl.

The aryl ring can optionally be substituted by one or more substituents. An "optionally substituted aryl" refers to an aryl having optionally one or more substituents (for example 1 to 5 substituents, for example 1, 2, 3 or 4) at any available point of attachment, selected from those defined above for substituted alkyl.

Where a carbon atom in an aryl group is replaced with a heteroatom, the resultant ring is referred to herein as a heteroaryl ring.

The term "heteroaryl" as used herein by itself or as part of another group refers but is not limited to 5 to 6 carbon-atom aromatic rings in which one or more carbon atoms can be replaced by oxygen, nitrogen or sulfur atoms. Non-limiting examples of such heteroaryl, include: pyrrolyl, furanyl, thiophenyl, pyrazolyl, imidazolyl, oxazolyl, isoxazolyl, thiazolyl, isothiazolyl, triazolyl, oxadiazolyl, thiadiazolyl, tetrazolyl, oxatriazolyl, thiatriazolyl, pyridinyl, pyrimidyl, pyrazinyl, pyridazinyl, oxazinyl, dioxinyl, thiazinyl, triazinyl, imidazo[2,1-b][1,3]thiazolyl, thieno[3,2-b]furanyl, thieno[3,2-b]thiophenyl, thieno[2,3-d][1,3]thiazolyl, thieno [2,3-d]imidazolyl, tetrazolo[1,5-a]pyridinyl, indolyl, indolizinyl, isoindolyl, benzofuranyl, isobenzofuranyl, benzothiophenyl, isobenzothiophenyl, indazolyl, benzimidazolyl, 1,3-benzoxazolyl, 1,2-benzisoxazolyl, 2,1-benzisoxazolyl, 1,3-benzothiazolyl, 1,2-benzoisothiazolyl, 2,1-benzoisothiazolyl, benzotriazolyl, 1,2,3-benzoxadiazolyl, 2,1,3-benzoxadiazolyl, 1,2,3-benzothiadiazolyl, 2,1,3-benzothiadiazolyl, thienopyridinyl, purinyl, imidazo[1,2-a] pyridinyl, 6-oxo-pyridazin-1(6H)-yl, 2-oxopyridin-1(2H)-yl, 6-oxo-pyridazin-1(6H)-yl, 2-oxopyridin-1(2H)-yl, 1,3-benzodioxolyl, quinolinyl, isoquinolinyl, cinnolinyl, quinazolinyl, quinoxalinyl, 7-azaindolyl, 6-azaindolyl, 5-azaindolyl, 4-azaindolyl.

An "optionally substituted heteroaryl" refers to a heteroaryl having optionally one or more substituents (for example 1 to 4 substituents, for example 1, 2, 3 or 4), selected from those defined above for substituted alkyl.

The term "halo" or "halogen" as a group or part of a group is generic for fluoro, chloro, bromo, or iodo, as well as any suitable isotope thereof.

Whenever the term "substituted" is used in the present invention, it is meant to indicate that one or more hydrogens on the atom indicated in the expression using "substituted" is replaced with a selection from the indicated group, provided that the indicated atom's normal valency is not exceeded, and that the substitution results in a chemically stable compound, i.e. a compound that is sufficiently robust to survive isolation to a useful degree of purity from a reaction mixture, and formulation into a therapeutic and/or diagnostic agent Where groups may be optionally substituted, such groups may be substituted once or more, and preferably once, twice or thrice. Substituents may be selected from, those defined above for substituted alkyl.

As used herein the terms such as "alkyl, aryl, or cycloalkyl, each being optionally substituted with" or "alkyl, aryl, or cycloalkyl, optionally substituted with" refers to optionally substituted alkyl, optionally substituted aryl and optionally substituted cycloalkyl.

More generally, from the above, it will be clear to the skilled person that the compounds of the invention may exist in the form of different isomers and/or tautomers, including but not limited to geometrical isomers, conformational isomers, E/Z-isomers, stereochemical isomers (i.e. enantiomers and diastereoisomers) and isomers that correspond to the presence of the same substituents on different positions of the rings present in the compounds of the invention. All such possible isomers, tautomers and mixtures thereof are included within the scope of the invention.

In addition, the invention includes isotopically-labelled compounds and salts, which are identical to compounds of formula (I), but for the fact that one or more atoms are replaced by an atom having an atomic mass or mass number different from the atomic mass or mass number most commonly found in nature. Examples of isotopes that can be incorporated into compounds of formula (I) are isotopes of hydrogen, carbon, nitrogen, fluorine, such as $^{3}H$, $^{11}C$, $^{13}N$, $^{14}C$, $^{15}O$ and $^{18}F$. Such isotopically-labelled compounds of formula (I) are useful in drug and/or substrate tissue distribution assays. For example $^{11}C$ and $^{18}F$ isotopes are particularly useful in PET (Positron Emission Tomography). PET is useful in brain imaging. Isotopically labeled compounds of formula (I) can generally be prepared by carrying out the procedures disclosed below, by substituting a readily available non-isotopically labeled reagent with an isotopically labeled reagent.

Whenever used in the present invention the term "compounds of the invention" or a similar term is meant to include the compounds of general Formula I and any subgroup thereof. This term also refers to the compounds as depicted in Table 1, their derivatives, N-oxides, salts, solvates, hydrates, stereoisomeric forms, racemic mixtures, tautomeric forms, optical isomers, analogues, pro-drugs, esters, and metabolites, as well as their quaternized nitrogen analogues. The N-oxide forms of said compounds are meant to comprise compounds wherein one or several nitrogen atoms are oxidized to the so-called N-oxide.

As used in the specification and the appended claims, the singular forms "a", "an", and "the" include plural referents unless the context clearly dictates otherwise. By way of example, "a compound" means one compound or more than one compound.

The terms described above and others used in the specification are well understood to those in the art.

In a particular embodiment, the present invention provides compounds of Formula I, or a stereoisomer, tautomer, racemic, metabolite, pro- or predrug, salt, hydrate, N-oxide form, or solvate thereof,

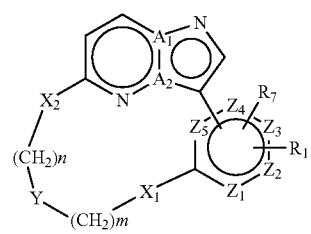

I

Wherein one or more of the following applies
$A_1$ and $A_2$ are selected from C and N; wherein when $A_1$ is C, then $A_2$ is N; and wherein when $A_2$ is C, then $A_1$ is N;
$R_1$ and $R_7$ are each independently selected from —H, -halo, —OH, —$C_{1-6}$alkyl, —O—$C_{1-6}$alkyl, —S—$C_{1-6}$alkyl, —$NR_9R_{10}$, —(C=O)—$R_4$, —$SO_2$—$R_4$, —CN, —$NR_9$—$SO_2$—$R_4$, —$C_{3-6}$cycloalkyl, and -$Het_6$; wherein each of said $C_{1-6}$alkyl is optionally and independently substituted with from 1 to 3 substituents selected from -halo, —OH, —NR$_{11}$R$_{12}$, —O—C$_{1-6}$alkyl, and —S—C$_{1-6}$alkyl;

R$_2$ is selected from —H, -halo, —OH, —C$_{1-6}$alkyl, —O—C$_{1-6}$alkyl, —S—C$_{1-6}$alkyl, —(C=O)—C$_{1-6}$alkyl, —(C=O)—O—C$_{1-6}$alkyl, —(C=O)—NR$_{27}$R$_{28}$, -Het$_3$, —(C=O)-Het$_3$, —SO$_2$-C$_{1-6}$alkyl, and —C$_{3-6}$cycloalkyl; wherein each of said C$_{1-6}$alkyl is optionally and independently substituted with from 1 to 3 substituents selected from -halo, —OH, —O—C$_{1-6}$alkyl, —S—C$_{1-6}$alkyl, -Het$_3$, —Ar$_2$, and —NR$_{13}$R$_{14}$;

R$_3$ is selected from —H, -halo, —OH, —C$_{1-6}$alkyl, —O—C$_{1-6}$alkyl, —S—C$_{1-6}$alkyl, —(C=O)—C$_{1-6}$alkyl, —(C=O)—O—C$_{1-6}$alkyl, -Het$_2$, —C$_{3-6}$cycloalkyl —(C=O)-Het$_2$, —(C=O)—NR$_{29}$R$_{30}$, and —SO$_2$—C$_{1-6}$alkyl; wherein each of said C$_{1-6}$alkyl is optionally and independently substituted with from 1 to 3 substituents selected from -halo, —OH, —O—C$_{1-6}$alkyl, —S—C$_{1-6}$alkyl, —NR$_{15}$R$_{16}$, -Het$_2$, and —Ar$_3$;

R$_4$ is independently selected from -halo, —OH, —C$_{1-6}$alkyl, —O—C$_{1-6}$alkyl, —S—C$_{1-6}$alkyl, —NR$_{17}$R$_{18}$, and -Het$_4$;

R$_5$ is selected from —H —C$_{1-6}$alkyl, —C$_{3-6}$cycloalkyl; wherein each of said C$_{1-6}$alkyl is optionally and independently substituted with from 1 to 3 substituents selected from -halo, —OH, —OC$_{1-6}$alkyl, —SC$_{1-6}$alkyl, -Het$_5$, and —NR$_{31}$R$_{32}$;

R$_6$ is selected from —H, —OH, -halo, —C$_{1-6}$alkyl, —O—C$_{1-6}$alkyl, —S—C$_{1-6}$alkyl, —NR$_{33}$R$_{34}$, and -Het$_8$;

R$_9$, R$_{10}$, R$_{11}$, R$_{12}$, R$_{13}$, R$_{14}$, R$_{15}$, R$_{16}$, R$_{17}$, R$_{18}$, R$_{19}$, R$_{20}$, R$_{21}$, R$_{22}$, R$_{23}$, R$_{24}$, R$_{25}$, R$_{26}$, R$_{27}$, R$_{28}$, R$_{29}$, R$_{30}$, R$_{31}$, R$_{32}$, R$_{33}$, R$_{34}$ are each independently selected from —H, —O, —C$_{1-6}$alkyl, and Het$_1$; wherein each of said C$_{1-6}$alkyl is optionally and independently substituted with from 1 to 3 substituents selected from -halo, —OH, —O—C$_{1-6}$alkyl, —S—C$_{1-6}$alkyl, —NR$_{35}$R$_{36}$, -Het$_7$, and —Ar$_4$;

R$_{35}$ and R$_{36}$ are each independently selected from —H, —O, and C$_{1-6}$alkyl; wherein each of said C$_{1-6}$alkyl is optionally and independently substituted with from 1 to 3 substituents selected from -halo, —OH, —O—C$_{1-6}$alkyl, and —S—C$_{1-6}$alkyl;

X$_1$ is selected from —C$_{1-6}$alkyl-, —O—C$_{1-6}$alkyl-, —S—C$_{1-6}$alkyl-, —(C=O)—, —NR$_3$—(C=O)—, —C$_{1-6}$alkyl-NR$_3$—(C=O)—, —NR$_3$—(C=O)—NR$_{35}$—, —NR$_3$—C$_{1-6}$alkyl-, —NR$_3$—, and —NR$_3$—SO$_2$—; wherein each of said C$_{1-6}$alkyl is optionally and independently substituted with from 1 to 3 substituents selected from -halo, —OH, —C$_{1-6}$alkyl, —O—C$_{1-6}$alkyl, —S—C$_{1-6}$alkyl, and —NR$_{23}$R$_{24}$;

X$_2$ is selected from —C$_{1-6}$alkyl-, —O—C$_{1-6}$alkyl-, —S—C$_{1-6}$alkyl-, —(C=O)—, —NR$_2$—(C=O)—, —NR$_2$—C$_{1-6}$alkyl-, —NR$_2$—, and —SO$_2$—NR$_2$—; wherein each of said C$_{1-6}$alkyl is optionally and independently substituted with from 1 to 3 substituents selected from -halo, —OH, —C$_{1-6}$alkyl, —O—C$_{1-6}$alkyl, —S—C$_{1-6}$alkyl, and —NR$_{25}$R$_{26}$;

Y is selected from a direct bond, —CHR$_6$—, —O—, —S—, and —NR$_5$—;

Ar$_2$, Ar$_3$, and Ar$_4$ are each independently a 5- or 6-membered aromatic heterocycle optionally comprising 1 or 2 heteroatoms selected from O, N and S; wherein each of said Ar$_2$, Ar$_3$, and Ar$_4$ is optionally and independently substituted with from 1 to 3 substituents selected from —NR$_{19}$R$_{20}$, —C$_{1-6}$alkyl, —O—C$_{1-6}$alkyl, and —S—C$_{1-6}$alkyl;

Het$_1$, Het$_2$, Het$_3$, Het$_4$, Het$_5$, Het$_6$, Het$_7$ and Het$_8$ are each independently a 5- or 6-membered monocyclic heterocycle having from 1 to 3 heteroatoms selected from O, N and S; wherein each heterocycle is optionally substituted with from 1 to 3 substituents selected from —C$_{1-6}$alkyl, —OC$_{1-6}$alkyl, —SC$_{1-6}$alkyl, and —NR$_{21}$R$_{22}$; wherein each of said C$_{1-6}$alkyl is optionally and independently substituted with from 1 to 3 -halo;

Z$_1$, Z$_2$, Z$_3$, Z$_4$ and Z$_5$ are each independently selected from C and N;

m and n are each independently 1, 2, 3, or 4.

In particular, X$_1$, and X$_2$ as used herein, represent biradicals, which taken together with the radicals to which they are attached form a macrocyclic pyrazolopyrimidine compound. Said biradicals may be present in either of both directions in the macrocyclic pyrazolopyrimidine, but are preferably present in the direction as described below:

Refering to formula I:

X$_1$ is selected from the list comprising *—C$_{1-6}$alkyl-, *—O—C$_{1-6}$alkyl-, *—S—C$_{1-6}$alkyl-, *—(C=O)—, —NR$_3$—(C=O)—*, *—C$_{1-6}$alkyl-NR$_3$—(C=O)—, *—NR$_3$—(C=O)—NR$_{35}$—, *—NR$_3$—C$_{1-6}$alkyl-, *—NR$_3$—, and *—NR$_3$—SO$_2$—; wherein said biradical is preferably attached to the aryl or heteroaryl moiety via *;

X$_2$ is selected from *—C$_{1-6}$alkyl-, *—O—C$_{1-6}$alkyl-, *—S—C$_{1-6}$alkyl-, *—(C=O)—, *—NR$_2$—(C=O)—, *—NR$_2$—C$_{1-6}$alkyl-, *—NR$_2$—, and —SO$_2$—NR$_2$—*; wherein said biradical is preferably attached to the pyrazolopyrimidine moiety via *;

In a specific embodiment, the present invention provides a compound as defined herein, wherein A$_1$ and A$_2$ are selected from C and N; wherein when A$_1$ is C, then A$_2$ is N; and wherein when A$_2$ is C, then A$_1$ is N;

R$_1$ is selected from —H, -halo, —OH, —C$_{1-6}$alkyl, —O—C$_{1-6}$alkyl, —NR$_9$R$_{10}$, —(C=O)—R$_4$, —CN, —NR$_9$—SO$_2$—R$_4$, and -Het$_6$; wherein each of said C$_{1-6}$alkyl is optionally and independently substituted with from 1 to 3 substituents selected from -halo, —OH, and —NR$_{11}$R$_{12}$;

R$_7$ is selected from —H, and -halo;

R$_2$ is selected from —H, —C$_{1-6}$alkyl, —(C=O)—NR$_{27}$R$_{28}$, —(C=O)-Het$_3$, and —SO$_2$—C$_{1-6}$alkyl; wherein each of said C$_{1-6}$alkyl is optionally and independently substituted with from 1 to 3 substituents selected from -halo, —OH, —O—C$_{1-6}$alkyl, -Het$_3$, and —NR$_{13}$R$_{14}$;

R$_3$ is selected from —H, —C$_{1-6}$alkyl, —(C=O)—C$_{1-6}$alkyl, —(C=O)-Het$_2$, —(C=O)—NR$_{29}$R$_{30}$, and —SO$_2$—C$_{1-6}$alkyl; wherein each of said C$_{1-6}$alkyl is optionally and independently substituted with from 1 to 3 substituents selected from -halo, —OH, and —O—C$_{1-6}$alkyl;

R$_4$ is independently selected from —OH, —O—C$_{1-6}$alkyl, —NR$_{17}$R$_{18}$, and -Het$_4$;

R$_5$ is selected from —H, —C$_{1-6}$alkyl, and —C$_{3-6}$cycloalkyl; wherein each of said C$_{1-6}$alkyl is optionally and independently substituted with from 1 to 3 substituents selected from -halo, —OH, —OC$_{1-6}$alkyl, -Het$_5$, and —NR$_{31}$R$_{32}$;

R$_6$ is selected from —OH, and —NR$_{33}$R$_{34}$;

R$_9$, R$_{10}$, R$_{11}$, R$_{12}$, R$_{13}$, R$_{14}$, R$_{17}$, R$_{18}$, R$_{27}$, R$_{28}$, R$_{29}$, R$_{30}$, R$_{31}$, R$_{32}$, R$_{33}$, R$_{34}$ are each independently selected from —H, —C$_{1-6}$alkyl, —NR$_{35}$R$_{36}$ or Het$_1$; wherein each of said C$_{1-6}$alkyl is optionally and independently substituted with from 1 to 3 substituents selected from -halo, —OH, and -Het$_7$;

R$_{35}$ and R$_{36}$ are each independently selected from —H, —O, and C$_{1-6}$alkyl; wherein each of said C$_{1-6}$alkyl is optionally and independently substituted with from 1 to 3 substituents selected from -halo, —OH, —O—C$_{1-6}$alkyl, and —S—C$_{1-6}$alkyl;

X$_1$ is selected from —C$_{1-6}$alkyl-, —O—C$_{1-6}$alkyl-, —(C=O)—, —S—C$_{1-6}$alkyl-, —NR$_3$—(C=O)—, —C$_{1-6}$alkyl-NR$_3$—(C=O)—, —NR$_3$—(C=O)—NR$_{35}$—, —NR$_3$—C$_{1-6}$alkyl-, and —NR$_3$—SO$_2$—;

$X_2$ is selected from —$C_{1-6}$alkyl-, —O—$C_{1-6}$alkyl-, —(C=O)—$NR_2$—, and —$NR_2$—$C_{1-6}$alkyl-;

Y is selected from a direct bond, —$CHR_6$—, —O—, —S—, and —$NR_5$—;

$Het_1$, $Het_2$, $Het_3$, $Het_4$, $Het_5$, $Het_6$, and $Het_7$ are each independently a 5- or 6-membered monocyclic heterocycle having from 1 to 3 heteroatoms selected from O, N and S, wherein each heterocycle is being optionally substituted with from 1 to 3 —$C_{1-6}$alkyl; each of said $C_{1-6}$alkyl being optionally and independently substituted with from 1 to 3 -halo $Z_1$, $Z_2$, $Z_3$, $Z_4$ and $Z_5$ are each independently selected from C and N;

m and n are each independently 1, 2, 3, or 4.

In another specific embodiment, the present invention provides a compound as defined herein wherein, $A_1$ and $A_2$ are selected from C and N; wherein when $A_1$ is C, then $A_2$ is N; and wherein when $A_2$ is C, then $A_1$ is N;

$R_1$ is selected from —H, -halo, —OH, —$C_{1-2}$alkyl, —O—$C_{1-2}$alkyl, —$NR_9R_{10}$, —(C=O)—$R_4$, —CN, —$NR_9$—$SO_2$—$R_4$, and -$Het_6$; wherein each of said $C_{1-2}$alkyl is optionally and independently substituted with from 1 to 3 substituents selected from -halo, —OH, and —$NR_{11}R_{12}$;

$R_7$ is selected from —H, and -halo;

$R_2$ is selected from —H, —$C_{1-3}$alkyl, —(C=O)—$NR_{27}R_{28}$, —(C=O)-$Het_3$, and —$SO_2$—$C_{1-3}$alkyl; wherein each of said $C_{1-3}$alkyl is optionally and independently substituted with from 1 to 3 substituents selected from -halo, —OH, —O—$CH_3$, -$Het_3$, and —$NR_{13}R_{14}$;

$R_3$ is selected from —H, —$C_{1-2}$alkyl, —(C=O)—$C_{1-2}$alkyl, —(C=O)-$Het_2$, —(C=O)—$NR_{29}R_{30}$, and —$SO_2$—$C_{1-2}$alkyl; wherein each of said $C_{1-2}$alkyl is optionally and independently substituted with from 1 to 3 substituents selected from -halo, —OH, and —O—$CH_3$;

$R_4$ is selected from —OH, —O—$CH_3$, —$NR_{17}R_{18}$, and -$Het_4$;

$R_5$ is selected from —H —$C_{1-3}$alkyl, and —$C_{3-6}$cycloalkyl; wherein each of said $C_{1-3}$alkyl is optionally and independently substituted with from 1 to 3 substituents selected from -halo, —OH, —$OCH_3$, -$Het_5$, and —$NR_{31}R_{32}$;

$R_6$ is selected from —OH, and —$NR_{33}R_{34}$;

$R_9$, $R_{10}$, $R_{11}$, $R_{12}$, $R_{13}$, $R_{14}$, $R_{31}$, $R_{32}$, $R_{33}$, and $R_{34}$ are each independently selected from —H and —$CH_3$;

$R_{17}$, $R_{18}$, $R_{27}$, and $R_{28}$ are each independently selected from —H and —$C_{1-2}$alkyl, each of said —$C_{1-2}$alkyl being optionally and independently substituted with from 1 to 3 substituents selected from —OH, -halo —$NR_{35}R_{36}$ and -$Het_7$ $R_{29}$ and $R_{30}$, are each independently selected from —H, —OH and —$OCH_3$;

$R_{35}$ and $R_{36}$ are each independently selected from —H, —O, and $C_{1-6}$alkyl; wherein each of said $C_{1-6}$alkyl is optionally and independently substituted with from 1 to 3 substituents selected from -halo, —OH, —O—$C_{1-6}$alkyl, and —S—$C_{1-6}$alkyl;

$X_1$ is selected from —$C_{1-6}$alkyl-, —O—$C_{1-6}$alkyl-, —(C=O)—, —S—$C_{1-6}$alkyl-, —$NR_3$—(C=O)—, —$C_{1-6}$alkyl-$NR_3$—(C=O)—, —$NR_3$—(C=O)—$NR_{35}$—, —$NR_3$—$C_{1-6}$alkyl-, and —$NR_3$—$SO_2$-$C_{1-6}$alkyl-;

$X_2$ is selected from —$C_{1-6}$alkyl-, —O—$C_{1-6}$alkyl-, —(C=O)—$NR_2$—, and —$NR_2$—$C_{1-6}$alkyl-;

Y is selected from a direct bond, —$CHR_6$—, —O—, —S—, and —$NR_5$—;

$Het_1$ is selected from -piperidinyl and -piperazinyl; each of said $Het_1$ being substituted with $C_{1-2}$alkyl; each of said $C_{1-2}$alkyl being optionally and independently substituted with from 1 to 3-halo;

$Het_2$ is -piperidinyl-$CH_3$;

$Het_3$ is selected from -piperazinyl, and -morpholinyl;

$Het_4$, is selected from -piperazinyl, and -morpholinyl; each of said $Het_4$ being optionally and independently substituted with $C_{1-2}$alkyl; each of said $C_{1-2}$alkyl being optionally and independently substituted with from 1 to 3 -halo;

$Het_5$ is -morpholinyl;

$Het_6$, is -piperazinyl;

$Het_7$ is -pyrrolidinyl;

$Z_1$, $Z_2$, $Z_3$, $Z_4$ and $Z_5$ are each independently selected from C and N m and n are each independently 1, 2, 3, or 4.

In yet a further embodiment, the present invention provides a compound a defined herein, wherein $A_1$ and $A_2$ are selected from C and N; wherein when $A_1$ is C, than $A_2$ is N; and wherein when $A_2$ is C, than $A_1$ is N;

$R_1$ is selected from —H, -halo, —$C_{1-6}$alkyl, —$OC_{1-6}$alkyl, and —(C=O)—$R_4$; wherein each of said $C_{1-6}$alkyl is optionally and independently substituted with from 1 to 3 -halo;

$R_7$ is —H;

$R_2$ is selected from —H, —$C_{1-6}$alkyl, —(C=O)—O—$C_{1-6}$alkyl, and —(C=O)-$Het_3$; wherein each of said $C_{1-6}$alkyl is optionally and independently substituted with from 1 to 3 substituents selected from —OH, —$OC_{1-6}$alkyl, -$Het_3$, and —$NR_{13}R_{14}$;

$R_3$ is selected from —H, —$C_{1-6}$alkyl, and —(C=O)-$Het_2$; wherein each of said $C_{1-6}$alkyl is optionally and independently substituted with from 1 to 3 substituents —OH;

$R_4$ is selected from —OH, —O—$C_{1-6}$alkyl, —$NR_{17}R_{18}$, and -$Het_4$;

$R_5$ is selected from —H, —$C_{1-6}$alkyl, and —$C_{3-6}$cycloalkyl; wherein each of said $C_{1-6}$alkyl is optionally and independently substituted with from 1 to 3 substituents selected from —OH, and -$Het_5$;

$R_{13}$, $R_{14}$, $R_{17}$, $R_{18}$, $R_{19}$ and $R_{20}$ are each independently selected from —H, —O, —$C_{1-6}$alkyl, and $Het_1$;

$X_1$ is selected from —$C_{1-6}$alkyl-, —O—$C_{1-6}$alkyl-, —$NR_3$—(C=O)—, —$C_{1-6}$alkyl-$NR_3$—(C=O)—, and —$NR_3$—$C_{1-6}$alkyl-;

$X_2$ is selected from —O—$C_{1-6}$alkyl-, —(C=O)—$NR_2$—, and —$NR_2$—$C_{1-6}$alkyl-;

Y is selected from a direct bond, —O—, —S—, and —$NR_5$—;

$Het_1$, $Het_2$, $Het_3$, $Het_4$ and $Het_5$ are each independently a 5- or 6-membered monocyclic heterocycle having from 1 to 3 heteroatoms selected from O, N and S, wherein each heterocycle is being optionally substituted with from 1 to 3 —$C_{1-6}$alkyl;

$Z_1$, $Z_2$, $Z_3$, $Z_4$ and $Z_5$ are each independently selected from C and N;

m and n are each independently 1, 2, 3, or 4.

In another specific embodiment, the present invention provides a compound as defined herein, wherein $A_1$ and $A_2$ are selected from C and N; wherein when $A_1$ is C, than $A_2$ is N; and wherein when $A_2$ is C, than $A_1$ is N $R_1$ is selected from —H, -halo, —$CF_3$, —$OC_{1-6}$alkyl, and —(C=O)—$R_4$;

$R_7$ is —H;

$R_2$ is selected from —H, —$C_{1-6}$alkyl, —(C=O)—O—$C_{1-6}$alkyl, and —(C=O)-$Het_3$; wherein each of said $C_{1-6}$alkyl is optionally and independently substituted with from 1 to 3 substituents selected from —OH, —OC$_{1-6}$alkyl, -Het$_3$, and —NR$_{13}$R$_{14}$;

R$_3$ is selected from —H, —C$_{1-6}$alkyl, and —(C=O)-Het$_2$; wherein each of said C$_{1-6}$alkyl is optionally and independently substituted with from 1 to 3 —OH;

R$_4$ is selected from —OH, —OC$_{1-6}$alkyl, —NR$_{17}$R$_{18}$, and -Het$_4$;

R$_5$ is selected from —H, —C$_{1-6}$alkyl, —C$_{3-6}$cycloalkyl; wherein each of said C$_{1-6}$alkyl is optionally and independently substituted with from 1 to 3 substituents selected from —OH, and -Het$_5$;

R$_{13}$ and R$_{14}$ are each independently selected from —H, and —C$_{1-6}$alkyl;

R$_{17}$ and R$_{18}$ are each independently selected from —H, —C$_{1-6}$alkyl, and -Het$_1$;

R$_{19}$ and R$_{20}$ are each independently selected from —O, and —C$_{1-6}$alkyl;

X$_1$ is selected from —C$_{1-6}$alkyl-, —O—C$_{1-6}$alkyl-, —NR$_3$—(C=O)—, —C$_{1-6}$alkyl-NR$_3$—(C=O)—, and —NR$_3$—C$_{1-6}$alkyl-;

X$_2$ is selected from —O—C$_{1-6}$alkyl-, —(C=O)—NR$_2$—, and —NR$_2$—C$_{1-6}$alkyl-;

Y is selected from a direct bond, —O—, —S—, and —NR$_5$—;

Het$_1$, Het$_2$, Het$_3$, Het$_4$ and Het$_5$ are each independently selected from -morpholinyl, -piperidinyl, -piperazinyl, and pyrrolidinyl, wherein each heterocycle is optionally substituted with from 1 to 3 —C$_{1-6}$alkyl;

Z$_1$, Z$_2$, Z$_3$, Z$_4$ and Z$_5$ are each independently selected from C and N m and n are each independently 1, 2, 3, or 4.

In yet a further embodiment, the present invention provides a compound according to this invention, wherein A$_1$ and A$_2$ are selected from C and N; wherein when A$_1$ is C, than A$_2$ is N; and wherein when A$_2$ is C, than A$_1$ is N R$_1$ is selected from —H, -halo, —CF$_3$, —OCH$_3$, and —(C=O)—R$_4$;

R$_7$ is —H;

R$_2$ is selected from —H, —C$_{2-4}$alkyl, —(C=O)—O—C$_{2-4}$alkyl, and —(C=O)-Het$_3$; wherein each of said C$_{2-4}$alkyl is optionally and independently substituted with from 1 to 3 substituents selected from —OH, —OCH$_3$, -Het$_3$, and —NR$_{13}$R$_{14}$;

R$_3$ is selected from —H, —C$_{1-2}$alkyl, and —(C=O)-Het$_2$; wherein each of said C$_{1-2}$alkyl is optionally and independently substituted with from 1 to 3 —OH;

R$_4$ is selected from —OH, —OCH$_3$, —NR$_{17}$R$_{18}$, and -Het$_4$;

R$_5$ is selected from —H, —C$_{1-3}$alkyl, and —C$_{3-6}$cycloalkyl; wherein each C$_{1-3}$alkyl is optionally substituted with from 1 to 3 substituents selected from —OH, and -Het$_5$;

R$_{13}$ and R$_{14}$ are —CH$_3$;

R$_{17}$ and R$_{18}$ are each independently selected from —H, —CH$_3$, and -Het$_1$;

R$_{19}$ and R$_{20}$ are each —O;

X$_1$ is selected from —C$_{1-6}$alkyl-, —O—C$_{2-6}$alkyl-, —NR$_3$—(C=O)—, —C$_{1-6}$alkyl-NR$_3$—(C=O)—, and —NR$_3$—C$_{2-3}$alkyl-;

X$_2$ is selected from —O—C$_2$alkyl-, —(C=O)—NR$_2$—, and —NR$_2$—C$_{1-3}$alkyl-;

Y is selected from a direct bond, —O—, —S—, and —NR$_5$—;

Het$_1$, Het$_2$, Het$_3$, Het$_4$ and Het$_5$ are each independently selected from -morpholinyl, -piperidinyl, -piperazinyl, and pyrrolidinyl, wherein each heterocycle is optionally substituted with from 1 to 3 —CH$_3$;

Z$_1$, Z$_2$, Z$_3$, Z$_4$ and Z$_5$ are each independently selected from C and N m and n are each independently 1, 2, 3, or 4.

In a further specific embodiment, the invention provides a compound as defined herein, wherein A$_1$ and A$_2$ are selected from C and N; wherein when A$_1$ is C, than A$_2$ is N; and wherein when A$_2$ is C, than A$_1$ is N;

R$_1$ is selected from —H, -halo, —CF$_3$, —OCH$_3$, —(C=O)—OH, —(C=O)—OCH$_3$, —(C=O)-Het$_4$, —(C=O)—NH-Het$_4$, —(C=O)—NH$_2$, and —(C=O)—NH—CH$_3$;

R$_7$ is —H;

R$_2$ is selected from —H, —C$_{2-4}$alkyl, —(C=O)—O—C$_2$alkyl, and —(C=O)-Het$_3$; wherein each C$_{2-4}$alkyl is optionally and independently substituted with 1 substituent selected from —OH, —OCH$_3$, -Het$_3$, and —NR$_{13}$R$_{14}$;

R$_3$ is selected from —H, —C$_{1-2}$alkyl, and —(C=O)-Het$_2$; wherein said C$_{1-2}$alkyl is optionally and independently substituted with 1 —OH;

R$_5$ is selected from —H, —C$_{1-3}$alkyl, and —C$_{3-6}$cycloalkyl; wherein each C$_{1-3}$alkyl is optionally and independently substituted with 1 to 3 substituents selected from —OH, and -Het$_5$;

R$_{13}$ and R$_{14}$ are —CH$_3$;

X$_1$ is selected from —C$_{1-6}$alkyl-, —O—C$_{2-6}$alkyl-, —NR$_3$—(C=O)—, and —NR$_3$—C$_2$alkyl-;

X$_2$ is selected from —O—C$_2$alkyl-, —(C=O)—NR$_2$—, and —NR$_2$—C$_{1-3}$alkyl-;

Y is selected from a direct bond, —O—, —S—, and —NR$_5$—;

Ar$_3$ is phenyl substituted with —NO$_2$;

Het$_2$ is -piperidinyl substituted with —CH$_3$;

Het$_3$ is selected from -morpholinyl, and -piperazinyl;

Het$_4$ is selected from -morpholinyl, -piperidinyl, and -piperazinyl; wherein said -piperidinyl and -piperazinyl are substituted with —CH$_3$;

Het$_5$ is selected from -morpholinyl, and -pyrrolidinyl;

Z$_1$, Z$_2$, Z$_3$, Z$_4$ and Z$_5$ are each independently selected from C and N m and n are each independently 1, 2, 3, or 4.

The invention further provides a compound as defined herein, wherein

A$_1$ and A$_2$ are selected from C and N; wherein when A$_1$ is C, then A$_2$ is N; and wherein when A$_2$ is C, then A$_1$ is N;

R$_1$ and R$_7$ are each independently selected from —H, -halo, —C$_{1-6}$alkyl, —O—C$_{1-6}$alkyl, and —(C=O)—R$_4$; wherein each of said C$_{1-6}$alkyl is optionally and independently substituted with from 1 to 3 substituents selected from -halo, and —OH;

R$_2$ is selected from —H, —C$_{1-6}$alkyl, —(C=O)—NR$_{27}$R$_{28}$, and —(C=O)-Het$_3$; wherein each of said C$_{1-6}$alkyl is optionally and independently substituted with from 1 to 3 substituents selected from -halo, —OH, and —NR$_{13}$R$_{14}$;

R$_3$ is selected from —H, —C$_{1-6}$alkyl, and —(C=O)-Het$_2$; wherein each of said C$_{1-6}$alkyl is optionally and independently substituted with —OH;

R$_4$ is independently selected from —OH, and —NR$_{17}$R$_{18}$;

R$_5$ is selected from —H —C$_{1-6}$alkyl, and —C$_{3-6}$cycloalkyl; wherein each of said C$_{1-6}$alkyl is optionally and independently substituted with from 1 to 3 substituents selected from -halo, —OH, —OC$_{1-6}$alkyl, -Het$_5$, and —NR$_{31}$R$_{32}$;

R$_{13}$, R$_{14}$, R$_{17}$, R$_{18}$, R$_{27}$, R$_{28}$, R$_{31}$, R$_{32}$ are each independently selected from —H, and —C$_{1-6}$alkyl; wherein each of said C$_{1-6}$alkyl is optionally and independently substituted with from 1 to 3 substituents selected from -halo, —NR$_{35}$R$_{36}$, and -Het$_7$;

R$_{35}$ and R$_{36}$ are each —C$_{1-6}$alkyl;

$X_1$ is selected from —O—$C_{1-6}$alkyl-, —(C=O)—, —$NR_3$—(C=O)—, $C_{1-6}$alkyl-$NR_3$—(C=O)—; and —$NR_3$—;
$X_2$ is selected from —O—$C_{1-6}$alkyl-, and —$NR_2$—;
Y is selected from a direct bond, —O—, and —$NR_5$—;
$Het_3$ is -piperazinyl
$Het_2$ is -piperidinyl substituted with —$CH_3$;
$Het_5$ is selected from -morpholinyl and -pyrrolidinyl;
$Het_7$ is -pyrrolidinyl;
$Z_1$, $Z_2$, $Z_3$, $Z_4$ and $Z_5$ are each independently selected from C and N;
m and n are each independently 1, 2, 3, or 4.

In a preferred embodiment, the present invention provides a compound as defined herein, wherein
$A_1$ is N; and $A_2$ is C;
$R_1$ and $R_7$ are each independently selected from —H, —$C_{1-6}$alkyl, —O—$C_{1-6}$alkyl, and —(C=O)—$R_4$; wherein each of said $C_{1-6}$alkyl is optionally and independently substituted with from 1 to 3 substituents selected from -halo, and —OH;
$R_2$ is selected from —H, —$C_{1-6}$alkyl, —(C=O)—$NR_{27}R_{28}$; wherein each of said $C_{1-6}$alkyl is optionally and independently substituted with from 1 to 3 substituents selected from —OH;
$R_3$ and $R_{35}$ are each independently selected from —H, —$C_{1-6}$alkyl, and —(C=O)-$Het_2$; wherein each of said $C_{1-6}$alkyl is optionally and independently substituted with —OH;
$R_4$ is independently selected from —OH, and —$NR_{17}R_{18}$;
$R_5$ is selected from —H —$C_{1-6}$alkyl, and —$C_{3-6}$cycloalkyl; wherein each of said $C_{1-6}$alkyl is optionally and independently substituted with from 1 to 3 substituents selected from -halo, —OH, —O$C_{1-6}$alkyl, and -$Het_5$;
$R_{17}$, $R_{18}$, $R_{27}$, and $R_{28}$ are each independently selected from —H, and —$C_{1-6}$alkyl; wherein each of said $C_{1-6}$alkyl is optionally and independently substituted with from 1 to 3 substituents selected from —$NR_{35}R_{36}$, and -$Het_7$;
$R_{35}$ and $R_{36}$ are each —$C_{1-6}$alkyl;
$X_1$ is selected from —O—$C_{1-6}$alkyl-, —$NR_3$—(C=O)—, and —$NR_3$—;
$X_2$ is selected from —O—$C_{1-6}$alkyl-, and —$NR_2$—;
Y is selected from a direct bond, —O—, and —$NR_5$—;
$Het_2$ is -piperidinyl substituted with —$CH_3$;
$Het_5$ is selected from -morpholinyl and -pyrrolidinyl;
$Het_7$ is -pyrrolidinyl;
$Z_1$, $Z_2$, $Z_3$, $Z_4$ and $Z_5$ are each C;
m and n are each independently 1, 2, 3, or 4.

In another preferred embodiment, the present invention provides a compound as defined herein, wherein
$A_1$ is N; and $A_2$ is C;
$R_1$ and $R_7$ are each —H;
$R_2$ is selected from —H, —(C=O)—$NR_{27}R_{28}$ and —$C_{1-6}$alkyl; wherein each of said $C_{1-6}$alkyl is optionally and independently substituted with from 1 to 3 —OH;
$R_5$ is selected from —H and —$C_{1-6}$alkyl; wherein each of said $C_{1-6}$alkyl is optionally and independently substituted with from 1 to 3 -$Het_5$;
$R_{27}$, and $R_{28}$ are each independently selected from —H, and —$C_{1-6}$alkyl; wherein each of said $C_{1-6}$alkyl is optionally and independently substituted with from 1 to 3 substituents selected from —$NR_{35}R_{36}$, and -$Het_7$;
$R_{35}$ and $R_{36}$ are each —$C_{1-6}$alkyl;
$X_1$ is selected from —O—$CH_2$—;
$X_2$ is selected from —O—$CH_2$—, and —$NR_2$—;
Y is —$NR_5$—;
$Het_5$ is selected from -morpholinyl and -pyrrolidinyl;
$Het_7$ is -pyrrolidinyl;

$Z_1$, $Z_2$, $Z_3$, $Z_4$ and $Z_5$ are each C;
m is 1; and
n is selected from 1, 2 and 3.

Particularly interesting compounds of the invention are compounds according to formula (I) wherein one or more of the following applies:
$A_1$ and $A_2$ are selected from C and N; wherein when $A_1$ is C, then $A_2$ is N; and wherein when $A_2$ is C, then $A_1$ is N;
$R_1$ and $R_7$ are each independently selected from —H, -halo, —$C_{1-6}$alkyl, —O—$C_{1-6}$alkyl, and —(C=O)—$R_4$; wherein each of said $C_{1-6}$alkyl is optionally and independently substituted with from 1 to 3 substituents selected from -halo, and —OH;
$R_2$ is selected from —H, —$C_{1-6}$alkyl, —(C=O)—$NR_{27}R_{28}$, and —(C=O)-$Het_3$; wherein each of said $C_{1-6}$alkyl is optionally and independently substituted with from 1 to 3 substituents selected from -halo, —OH, and —$NR_{13}R_{14}$;
$R_3$ is selected from —H, —$C_{1-6}$alkyl, and —(C=O)-$Het_2$; wherein each of said $C_{1-6}$alkyl is optionally and independently substituted with —OH;
$R_4$ is independently selected from —OH, and —$NR_{17}R_{18}$;
$R_5$ is selected from —H —$C_{1-6}$alkyl, and —$C_{3-6}$cycloalkyl; wherein each of said $C_{1-6}$alkyl is optionally and independently substituted with from 1 to 3 substituents selected from -halo, —OH, —O$C_{1-6}$alkyl, -$Het_5$, and —$NR_{31}R_{32}$;
$R_{13}$, $R_{14}$, $R_{17}$, $R_{18}$, $R_{27}$, $R_{28}$, $R_{31}$, $R_{32}$ are each independently selected from —H, and —$C_{1-6}$alkyl; wherein each of said $C_{1-6}$alkyl is optionally and independently substituted with from 1 to 3 substituents selected from -halo, —$NR_{35}R_{36}$, and -$Het_7$;
$R_{35}$ and $R_{36}$ are each —$C_{1-6}$alkyl;
$X_1$ is selected from —O—$C_{1-6}$alkyl-, —(C=O)—, —$NR_3$—(C=O)—, $C_{1-6}$alkyl-$NR_3$—(C=O)—; and —$NR_3$—;
$X_2$ is selected from —O—$C_{1-6}$alkyl-, and —$NR_2$—;
Y is selected from a direct bond, —O—, and —$NR_5$—;
$Het_3$ is -piperazinyl
$Het_2$ is -piperidinyl substituted with —$CH_3$;
$Het_5$ is selected from -morpholinyl and -pyrrolidinyl;
$Het_7$ is -pyrrolidinyl;
$Z_1$, $Z_2$, $Z_3$, $Z_4$ and $Z_5$ are each independently selected from C and N;
m and n are each independently 1, 2, 3, or 4.

Further particularly interesting compounds of the invention are compounds according to formula (I) wherein one or more of the following applies:
$A_1$ is N; and $A_2$ is C;
$R_1$ is selected from —H, -halo, —$C_{1-6}$alkyl, —(C=O)—$R_4$, and —O—$C_{1-6}$alkyl, wherein each of said $C_{1-6}$alkyl is optionally and independently substituted with from 1 to 3 substituents selected from -halo, and —OH;
$R_7$ is —H;
$R_2$ is selected from —H, —$C_{1-6}$alkyl, —(C=O)—$NR_{27}R_{28}$, and —(C=O)-$Het_3$; wherein each of said $C_{1-6}$alkyl is optionally and independently substituted with from 1 to 3 substituents selected from -halo, —OH, and —$NR_{13}R_{14}$;
$R_3$ is selected from —H, —$C_{1-6}$alkyl, and —(C=O)-$Het_2$; wherein each of said $C_{1-6}$alkyl is optionally and independently substituted with from 1 to 3 —OH;
$R_4$ is independently selected from —OH and —$NH_{17}R_{18}$;
$R_5$ is selected from —H —$C_{1-6}$alkyl, —$C_{3-6}$cycloalkyl; wherein each of said $C_{1-6}$alkyl is optionally and independently substituted with from 1 to 3 substituents selected from -halo, —OH, —O$C_{1-6}$alkyl, -$Het_5$, and —$NR_{31}R_{32}$;
$R_{13}$ and $R_{14}$ are each —$C_{1-6}$alkyl;

$R_{17}$ and $R_{18}$ are each independently selected from —H, and —$C_{1-6}$alkyl; wherein each of said $C_{1-6}$alkyl is optionally and independently substituted with from 1 to 3 substituents selected from -halo, $R_{27}$, and $R_{28}$ are each independently selected from —H and —$C_{1-6}$alkyl; wherein each of said $C_{1-6}$alkyl is optionally and independently substituted with from 1 to 3 substituents selected from -halo, —$NR_{35}R_{36}$, and -Het$_7$;

$R_{31}$ and $R_{32}$ are each —$C_{1-6}$alkyl;

$R_{35}$ and $R_{36}$ are each —$C_{1-6}$alkyl $X_1$ is selected from —O—$C_{1-6}$alkyl-, —$NR_3$—(C=O)—, —$NR_3$—$C_{1-6}$alkyl-;

$X_2$ is selected from —O—$C_{1-6}$alkyl-, and —$NR_2$

Y is selected from —O— and —$NR_5$—;

Het$_3$ is -piperazinyl

Het$_2$ is -piperidinyl substituted with —$CH_3$;

Het$_5$ is selected from -morpholinyl and -pyrrolidinyl;

Het$_7$ is -pyrrolidinyl;

$Z_1, Z_2, Z_3, Z_4$ and $Z_5$ are each independently selected from C and N;

m and n are each independently 1, 2, 3, or 4.

In another particular embodiment, the present invention provides compounds of Formula I, wherein one or more of the following applies:

$A_1$ is N; and $A_2$ is C;

$R_1$ and $R_7$ are each —H;

$R_2$ is selected from —H, —(C=O)—$NR_{27}R_{28}$ and —$C_{1-6}$alkyl; wherein each of said $C_{1-6}$alkyl is optionally and independently substituted with from 1 to 3 —OH;

$R_5$ is selected from —H and —$C_{1-6}$alkyl; wherein each of said $C_{1-6}$alkyl is optionally and independently substituted with from 1 to 3-Het$_5$;

$R_{27}$, and $R_{28}$ are each independently selected from —H, and —$C_{1-6}$alkyl; wherein each of said $C_{1-6}$alkyl is optionally and independently substituted with from 1 to 3 substituents selected from —$NR_{35}R_{36}$, and -Het$_7$;

$R_{35}$ and $R_{36}$ are each —$C_{1-6}$alkyl;

$X_1$ is selected from —O—$CH_2$—;

$X_2$ is selected from —O—$CH_2$—, and —$NR_2$—;

Y is —$NR_5$—;

Het$_5$ is selected from -morpholinyl and -pyrrolidinyl;

Het$_7$ is -pyrrolidinyl;

$Z_1, Z_2, Z_3, Z_4$ and $Z_5$ are each C;

m is 1; and n is selected from 1, 2 and 3.

In particular the present invention provides a compound, or a stereoisomer, tautomer, racemic, metabolite, pro- or predrug, salt, hydrate, N-oxide form, or solvate thereof, selected from the list comprising:

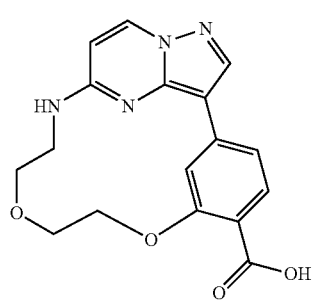

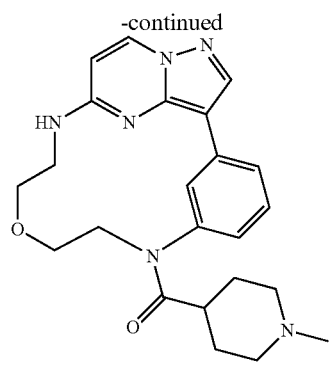

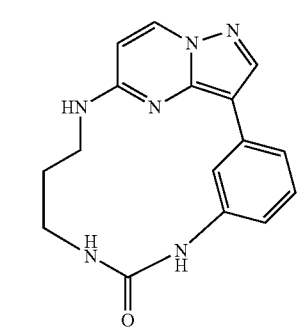

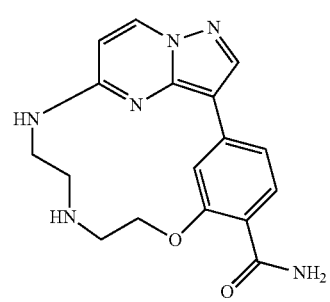

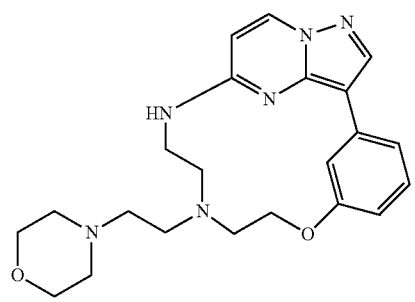

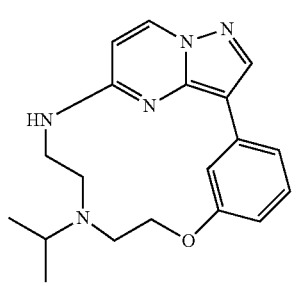

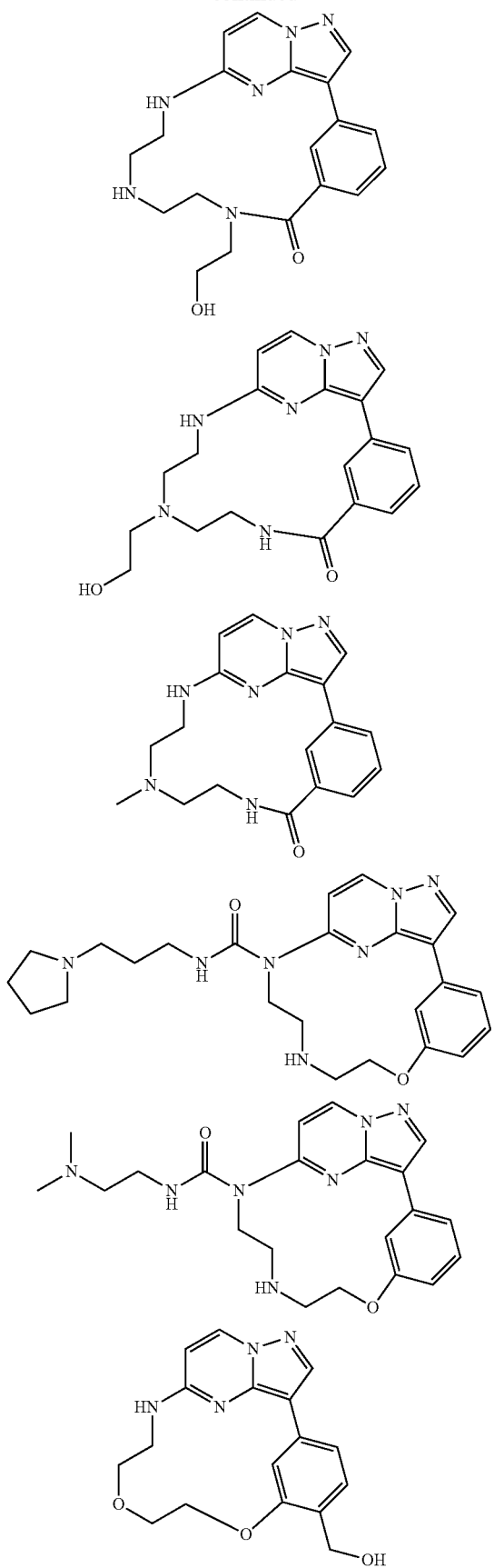
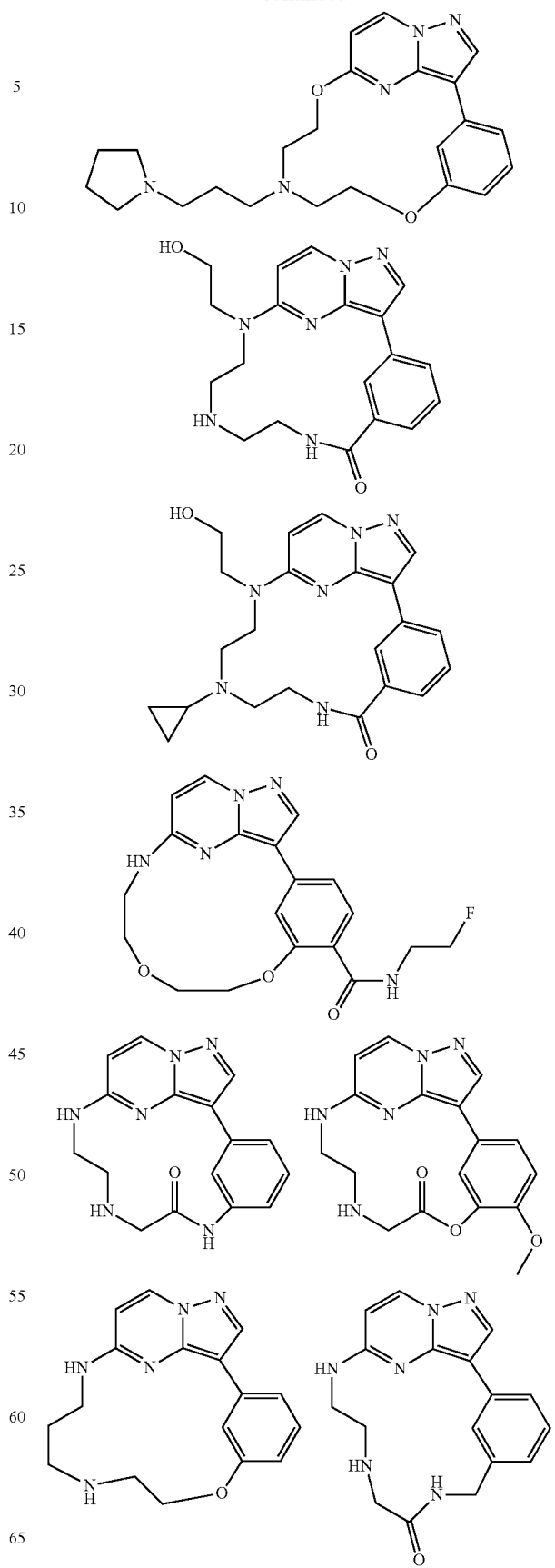

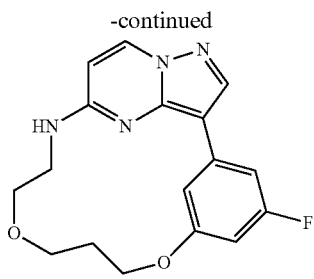

More in particular the present invention provides a compound selected from the list comprising:

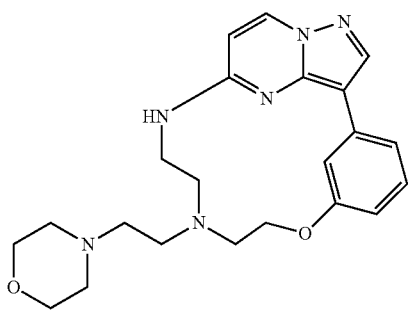

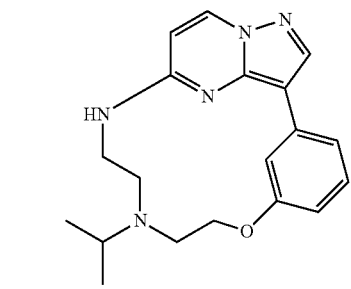

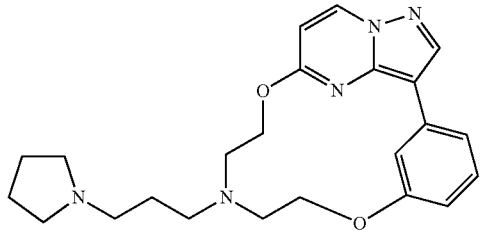

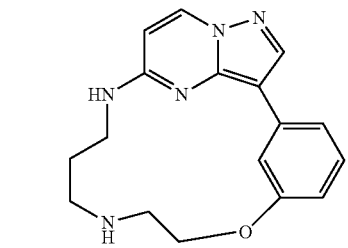

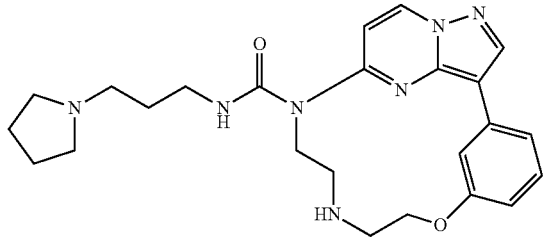

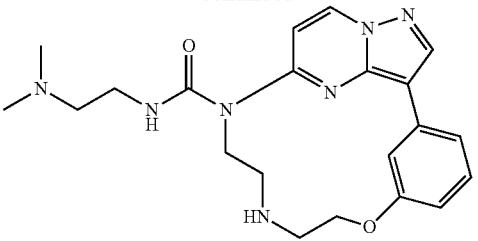

more in particular

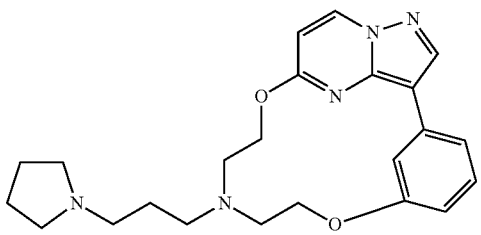 [SMILES: c1cc2cc(c1)-c1cnn3ccc(nc13)OCCN(CCCN1CCCC1)CCO2]

In a preferred embodiment, the present invention provides a compound as defined herein above, wherein the pyrazolopyrimidine moiety is linked to the aryl or heteroaryl moiety at position $Z_4$ and wherein $R_7$ is linked to the aryl or heteroaryl moiety at position $Z_5$ in accordance with Formula I.

The compounds of the present invention can be prepared according to the reaction schemes provided in the examples hereinafter, but those skilled in the art will appreciate that these are only illustrative for the invention and that the compounds of this invention can be prepared by any of several standard synthetic processes commonly used by those skilled in the art of organic chemistry.

In a preferred embodiment, the present invention provides a compound as defined herein above, wherein the pyrazolopyrimidine moiety is linked to the aryl or heteroaryl moiety at position $Z_4$ and wherein $R_7$ is linked to the aryl or heteroaryl moiety at position $Z_5$ in accordance with Formula I.

In a further aspect, the present invention provides a compound according to this invention for use as a human or veterinary medicine. More in particular, it provides the use of a compound according to this invention for the manufacture of a medicament for the treatment of cell proliferative disorders, such as cancer.

The present invention further provides a pharmaceutical composition comprising a compound according to this invention, suitable for use as a human or veterinary medicine.

In yet a further aspect, the present invention provides the use of a compound or a composition according to this invention, suitable for inhibiting the activity of a kinase; in particular a FLT3 kinase.

It further provides the use of a compound or a composition according to this invention for the prevention and/or or treatment of cell proliferative disorders, such as cancer.

In a further aspect, the present invention provides a method for the prevention and/or treatment of cell proliferative disorders such as cancer; said method comprising administering to a subject in need thereof a compound or a composition according to this invention. Further embodiments of the present invention are detailed herein below in the form of numbered statements:

1. A compound of Formula I or a stereoisomer, tautomer, racemic, metabolite, pro- or predrug, salt, hydrate, N-oxide form, or solvate thereof,

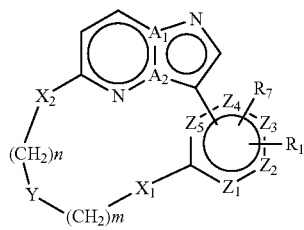

I

Wherein
A₁ and A₂ are selected from C and N; wherein when A₁ is C, then A₂ is N; and wherein when A₂ is C, then A₁ is N;
R₁ and R₇ are each independently selected from —H, -halo, —OH, —C₁₋₆alkyl, —O—C₁₋₆alkyl, —S—C₁₋₆alkyl, —NR₉R₁₀, —(C=O)—R₄, —SO₂—R₄, —CN, —NR₃—SO₂—R₄, —C₃₋₆cycloalkyl, and -Het₆; wherein each of said C₁₋₆alkyl is optionally and independently substituted with from 1 to 3 substituents selected from -halo, —OH, —NR₁₁R₁₂, —O—C₁₋₆alkyl, and —S—C₁₋₆alkyl;
R₂ is selected from —H, -halo, —OH, —C₁₋₆alkyl, —O—C₁₋₆alkyl, —S—C₁₋₆alkyl, —(C=O)—C₁₋₆alkyl, —(C=O)—O—C₁₋₆alkyl, —(C=O)—NR₂₇R₂₈, -Het₃, —(C=O)-Het₃, —SO₂—C₁₋₆alkyl, and —C₃₋₆cycloalkyl; wherein each of said C₁₋₆alkyl is optionally and independently substituted with from 1 to 3 substituents selected from -halo, —OH, —O—C₁₋₆alkyl, —S—C₁₋₆alkyl, -Het₃, —Ar₂, and —N₁₃R₁₄;
R₃ and R₃₅ are each independently selected from —H, -halo, —OH, —C₁₋₆alkyl, —O—C₁₋₆alkyl, —S—C₁₋₆alkyl, —(C=O)—C₁₋₆alkyl, —(C=O)—O—C₁₋₆alkyl, -Het₂, —C₃₋₆cycloalkyl —(C=O)-Het₂, —(C=O)—NR₂₉R₃₀, and —SO₂—C₁₋₆alkyl; wherein each of said C₁₋₆alkyl is optionally and independently substituted with from 1 to 3 substituents selected from -halo, —OH, —O—C₁₋₆alkyl, —S—C₁₋₆alkyl, —NR₁₅R₁₆, -Het₂, and —Ar₃;
R₄ is independently selected from -halo, —OH, —C₁₋₆alkyl, —O—C₁₋₆alkyl, —S—C₁₋₆alkyl, —NR₁₇R₁₈, and -Het₄;
R₅ is selected from —H —C₁₋₆alkyl, —C₃₋₆cycloalkyl; wherein each of said C₁₋₆alkyl is optionally and independently substituted with from 1 to 3 substituents selected from -halo, —OH, —OC₁₋₆alkyl, —SC₁₋₆alkyl, -Het₆, and —NR₃₁R₃₂;
R₆ is selected from —H, —OH, -halo, —C₁₋₆alkyl, —O—C₁₋₆alkyl, —S—C₁₋₆alkyl, —NR₃₃R₃₄, and -Het₈;
R₉, R₁₀, R₁₁, R₁₂, R₁₃, R₁₄, R₁₅, R₁₆, R₁₇, R₁₈, R₁₉, R₂₀, R₂₁, R₂₂, R₂₃, R₂₄, R₂₅, R₂₆, R₂₇, R₂₈, R₂₉, R₃₀, R₃₁, R₃₂, R₃₃, R₃₄ are each independently selected from —H, —O, —C₁₋₆alkyl, and Het₁; wherein each of said C₁₋₆alkyl is optionally and independently substituted with from 1 to 3 substituents selected from -halo, —OH, —O—C₁₋₆alkyl, —S—C₁₋₆alkyl, —NR₃₅R₃₆, -Het₇, and —Ar₄;
R₃₅ and R₃₆ are each independently selected from —H, —O, and C₁₋₆alkyl; wherein each of said C₁₋₆alkyl is optionally and independently substituted with from 1 to 3 substituents selected from -halo, —OH, —O—C₁₋₆alkyl, and —S—C₁₋₆alkyl;
X₁ is selected from —C₁₋₆alkyl-, —O—C₁₋₆alkyl-, —S—C₁₋₆alkyl-, —(C=O)—, —NR₃—(C=O)—, —NR₃—(C=O)—NR₃₅—, —NR₃—C₁₋₆alkyl-, —NR₃—, and —NR₃—SO₂—; wherein each of said C₁₋₆alkyl is optionally and independently substituted with from 1 to 3 substituents selected from -halo, —OH, —C₁₋₆alkyl, —O—C₁₋₆alkyl, —S—C₁₋₆alkyl, and —NR₂₃R₂₄;

X₂ is selected from —C₁₋₆alkyl-, —O—C₁₋₆alkyl-, —S—C₁₋₆alkyl-, —(C=O)—, —NR₂—(C=O)—, —NR₂—C₁₋₆alkyl-, —NR₂—, and —SO₂—NR₂—; wherein each of said C₁₋₆alkyl is optionally and independently substituted with from 1 to 3 substituents selected from -halo, —OH, —C₁₋₆alkyl, —O—C₁₋₆alkyl, —S—C₁₋₆alkyl, and —NR₂₅R₂₆;
Y is selected from a direct bond, —CHR₆—, —O—, —S—, and —NR₅—;
Ar₂, Ar₃, and Ar₄ are each independently a 5- or 6-membered aromatic heterocycle optionally comprising 1 or 2 heteroatoms selected from O, N and S; wherein each of said Ar₂, Ar₃, and Ar₄ is optionally and independently substituted with from 1 to 3 substituents selected from —NR₁₉R₂₀, —C₁₋₆alkyl, —O—C₁₋₆alkyl, and —S—C₁₋₆alkyl;
Het₁, Het₂, Het₃, Het₄, Het₅, Het₆, Het₇ and Het₈ are each independently a 5- or 6-membered monocyclic heterocycle having from 1 to 3 heteroatoms selected from O, N and S, wherein each heterocycle is optionally substituted with from 1 to 3 substituents selected from —C₁₋₆alkyl, —OC₁₋₆alkyl, —SC₁₋₆alkyl, and —NR₂₁R₂₂; wherein each of said C₁₋₆alkyl is optionally and independently substituted with from 1 to 3 -halo;
Z₁, Z₂, Z₃, Z₄ and Z₅ are each independently selected from C and N;
m and n are each independently 1, 2, 3, or 4.
2. A compound as defined in statement 1, wherein
A₁ and A₂ are selected from C and N; wherein when A₁ is C, then A₂ is N; and wherein when A₂ is C, then A₁ is N;
R₁ is selected from —H, -halo, —OH, —C₁₋₆alkyl, —O—C₁₋₆alkyl, —NR₉R₁₀, —(C=O)—R₄, —CN, —NR₉—SO₂—R₄, and -Het₆; wherein each of said C₁₋₆alkyl is optionally and independently substituted with from 1 to 3 substituents selected from -halo, —OH, and —NR₁₁R₁₂;
R₇ is selected from —H, and -halo;
R₂ is selected from —H, —C₁₋₆alkyl, —(C=O)—NR₂₇R₂₈, —(C=O)-Het₃, and —SO₂—C₁₋₆alkyl; wherein each of said C₁₋₆alkyl is optionally and independently substituted with from 1 to 3 substituents selected from -halo, —OH, —O—C₁₋₆alkyl, -Het₃, and —NR₁₃R₁₄;
R₃ and R₃₅ are each independently selected from —H, —C₁₋₆alkyl, —(C=O)—C₁₋₆alkyl, —(C=O)-Het₂, —(C=O)—NR₂₉R₃₀, and —SO₂—C₁₋₆alkyl; wherein each of said C₁₋₆alkyl is optionally and independently substituted with from 1 to 3 substituents selected from -halo, —OH, and —O—C₁₋₆alkyl;
R₄ is independently selected from —OH, —O—C₁₋₆alkyl, —NR₁₇R₁₈, and -Het₄;
R₅ is selected from —H, —C₁₋₆alkyl, and —C₃₋₆cycloalkyl; wherein each of said C₁₋₆alkyl is optionally and independently substituted with from 1 to 3 substituents selected from -halo, —OH, —OC₁₋₆alkyl, -Het₅, and —NR₃₁R₃₂;
R₆ is selected from —OH, and —NR₃₃R₃₄;
R₉, R₁₀, R₁₁, R₁₂, R₁₃, R₁₄, R₁₇, R₁₈, R₂₇, R₂₈, R₂₃, R₃₀, R₃₁, R₃₂, R₃₃, R₃₄ are each independently selected from —H, —C₁₋₆alkyl, or Het₁; wherein each of said C₁₋₆alkyl is optionally and independently substituted with from 1 to 3 substituents selected from -halo, —OH, and —-Het₇;
X₁ is selected from —C₁₋₆alkyl-, —O—C₁₋₆alkyl-, —S—C₁₋₆alkyl-, —NR₃—(C=O)—, —NR₃—(C=O)—NR₃₅—, 13 NR₃—C₁₋₆alkyl-, and —NR₃—SO₂—;
X₂ is selected from —C₁₋₆alkyl-, —O—C₁₋₆alkyl-, —(C=O)—NR₂—, and —NR₂—C₁₋₆alkyl-;
Y is selected from a direct bond, —CHR₆—, —O—, —S—, and —NR₅—;
Het₁, Het₂, Het₃, Het₄, Het₅, Het₆, and Het₇ are each independently a 5- or 6-membered monocyclic heterocycle having from 1 to 3 heteroatoms selected from O, N and S, wherein each heterocycle is being optionally substituted with from 1 to 3 —$C_{1-6}$alkyl; each of said $C_{1-6}$alkyl being optionally and independently substituted with from 1 to 3 -halo $Z_1$, $Z_2$, $Z_3$, $Z_4$ and $Z_5$ are each independently selected from C and N;

m and n are each independently 1, 2, 3, or 4.

3. A compound as defined in statement 1, wherein $A_1$ and $A_2$ are selected from C and N; wherein when $A_1$ is C, then $A_2$ is N; and wherein when $A_2$ is C, then $A_1$ is N;

$R_1$ is selected from —H, -halo, —OH, —$C_{1-2}$alkyl, —O—$C_{1-2}$alkyl, —$NR_9R_{10}$, —(C=O)—$R_4$, —CN, —$NR_9$—$SO_2$—$R_4$, and -$Het_6$; wherein each of said $C_{1-2}$alkyl is optionally and independently substituted with from 1 to 3 substituents selected from -halo, —OH, and —$NR_{11}R_{12}$;

$R_7$ is selected from —H, and -halo;

$R_2$ is selected from —H, —$C_{1-3}$alkyl, —(C=O)—$NR_{27}R_{28}$, —(C=O)-$Het_3$, and —$SO_2$—$C_{1-3}$alkyl; wherein each of said $C_{1-3}$alkyl is optionally and independently substituted with from 1 to 3 substituents selected from -halo, —OH, —O—$CH_3$, -$Het_3$, and —$NR_{13}R_{14}$;

$R_3$ and $R_{35}$ are each independently selected from —H, —$C_{1-2}$alkyl, —(C=O)—$C_{1-2}$alkyl, —(C=O)-$Het_2$, —(C=O)—$NR_{29}R_{30}$, and —$SO_2$—$C_{1-2}$alkyl; wherein each of said $C_{1-2}$alkyl is optionally and independently substituted with from 1 to 3 substituents selected from -halo, —OH, and —O—$CH_3$;

$R_4$ is selected from —OH, —O—$CH_3$, —$NR_{17}R_{18}$, and -$Het_4$;

$R_5$ is selected from —H —$C_{1-3}$alkyl, and —$C_{3-6}$cycloalkyl; wherein each of said $C_{1-3}$alkyl is optionally and independently substituted with from 1 to 3 substituents selected from -halo, —OH, —$OCH_3$, -$Het_5$, and —$NR_{31}R_{32}$;

$R_6$ is selected from —OH, and —$NR_{33}R_{34}$;

$R_9$, $R_{10}$, $R_{11}$, $R_{12}$, $R_{13}$, $R_{14}$, $R_{31}$, $R_{32}$, $R_{33}$, and $R_{34}$ are each independently selected from —H and —$CH_3$;

$R_{17}$, $R_{18}$, $R_{27}$, and $R_{28}$ are each independently selected from —H and —$C_{1-2}$alkyl, each of said —$C_{1-2}$alkyl being optionally and independently substituted with from 1 to 3 substituents selected from —OH, -halo and -$Het_7$ $R_{29}$ and $R_{30}$, are each independently selected from —H, —OH and —$OCH_3$;

$X_1$ is selected from —$C_{1-6}$alkyl-, —O—$C_{1-6}$alkyl-, —S—$C_{1-6}$alkyl-, —$NR_3$—(C=O)—, —$NR_3$—(C=O)—$NR_{35}$—, —$NR_3$—$C_{1-6}$alkyl-, and —$NR_3$—$SO_2$—$C_{1-6}$alkyl-;

$X_2$ is selected from —$C_{1-6}$alkyl-, —O—$C_{1-6}$alkyl-, —(C=O)—$NR_2$—, and —$NR_2$—$C_{1-6}$alkyl-;

Y is selected from a direct bond, —$CHR_6$—, —O—, —S—, and —$NR_5$—;

$Het_1$ is selected from -piperidinyl and -piperazinyl; each of said $Het_1$ being substituted with $C_{1-2}$alkyl; each of said $C_{1-2}$alkyl being optionally and independently substituted with from 1 to 3-halo;

$Het_2$ is -piperidinyl-$CH_3$;

$Het_3$ is selected from -piperazinyl, and -morpholinyl;

$Het_4$, is selected from -piperazinyl, and -morpholinyl; each of said $Het_4$ being optionally and independently substituted with $C_{1-2}$alkyl; each of said $C_{1-2}$alkyl being optionally and independently substituted with from 1 to 3 -halo;

$Het_5$ is -morpholinyl;

$Het_6$ is -piperazinyl;

$Het_7$ is -pyrrolidinyl;

$Z_1$, $Z_2$, $Z_3$, $Z_4$ and $Z_5$ are each independently selected from C and N m and n are each independently 1, 2, 3, or 4.

4. A compound as defined in statement 1, wherein $A_1$ and $A_2$ are selected from C and N; wherein when $A_1$ is C, than $A_2$ is N; and wherein when $A_2$ is C, than $A_1$ is N;

$R_1$ is selected from —H, -halo, —$C_{1-6}$alkyl, —$OC_{1-6}$alkyl, and —(C=O)—$R_4$; wherein each of said $C_{1-6}$alkyl is optionally and independently substituted with from 1 to 3 -halo;

$R_7$ is —H;

$R_2$ is selected from —H, —$C_{1-6}$alkyl, —(C=O)—O—$C_{1-6}$alkyl, and —(C=O)-$Het_3$; wherein each of said $C_{1-6}$alkyl is optionally and independently substituted with from 1 to 3 substituents selected from —OH, —$OC_{1-6}$alkyl, -$Het_3$, and —$NR_{13}R_{14}$;

$R_3$ is selected from —H, —$C_{1-6}$alkyl, and —(C=O)-$Het_2$; wherein each of said $C_{1-6}$alkyl is optionally and independently substituted with from 1 to 3 substituents —OH;

$R_4$ is selected from —OH, —O—$C_{1-6}$alkyl, —$NR_{17}R_{18}$, and -$Het_4$;

$R_5$ is selected from —H, —$C_{1-6}$alkyl, and —$C_{3-6}$cycloalkyl; wherein each of said $C_{1-6}$alkyl is optionally and independently substituted with from 1 to 3 substituents selected from —OH, and -$Het_5$;

$R_{13}$, $R_{14}$, $R_{17}$, $R_{18}$, $R_{19}$ and $R_{20}$ are each independently selected from —H, —O, —$C_{1-6}$alkyl, and $Het_1$;

$X_1$ is selected from —$C_{1-6}$alkyl-, —O—$C_{1-6}$alkyl-, —$NR_3$—(C=O)—, and —$NR_3$—$C_{1-6}$alkyl-;

$X_2$ is selected from —O—$C_{1-6}$alkyl-, —(C=O)—$NR_2$—, and —$NR_2$—$C_{1-6}$alkyl-;

Y is selected from a direct bond, —O—, —S—, and —$NR_5$—;

$Het_1$, $Het_2$, $Het_3$, $Het_4$ and $Het_5$ are each independently a 5- or 6-membered monocyclic heterocycle having from 1 to 3 heteroatoms selected from O, N and S, wherein each heterocycle is being optionally substituted with from 1 to 3 —$C_{1-6}$alkyl;

$Z_1$, $Z_2$, $Z_3$, $Z_4$ and $Z_5$ are each independently selected from C and N;

m and n are each independently 1, 2, 3, or 4.

5. A compound as defined in statement 1, wherein $A_1$ and $A_2$ are selected from C and N; wherein when $A_1$ is C, than $A_2$ is N; and wherein when $A_2$ is C, than $A_1$ is N $R_1$ is selected from —H, -halo, —$CF_3$, —$OC_{1-6}$alkyl, and —(C=O)—$R_4$;

$R_7$ is —H;

$R_2$ is selected from —H, —$C_{1-6}$alkyl, —(C=O)—O—$C_{1-6}$alkyl, and —(C=O)-$Het_3$; wherein each of said $C_{1-6}$alkyl is optionally and independently substituted with from 1 to 3 substituents selected from —OH, —$OC_{1-6}$alkyl, -$Het_3$, and —$NR_{13}R_{14}$;

$R_3$ is selected from —H, —$C_{1-6}$alkyl, and —(C=O)-$Het_2$; wherein each of said $C_{1-6}$alkyl is optionally and independently substituted with from 1 to 3 —OH;

$R_4$ is selected from —OH, —$OC_{1-6}$alkyl, —$NR_{17}R_{18}$, and -$Het_4$;

$R_5$ is selected from —H, —$C_{1-6}$alkyl, —$C_{3-6}$cycloalkyl; wherein each of said $C_{1-6}$alkyl is optionally and independently substituted with from 1 to 3 substituents selected from —OH, and -$Het_5$;

$R_{13}$ and $R_{14}$ are each independently selected from —H, and —$C_{1-6}$alkyl;

$R_{17}$ and $R_{18}$ are each independently selected from —H, —$C_{1-6}$alkyl, and -$Het_1$:

$R_{19}$ and $R_{20}$ are each independently selected from —O, and —$C_{1-6}$alkyl;

$X_1$ is selected from —$C_{1-6}$alkyl-, —O—$C_{1-6}$alkyl-, —$NR_3$—(C=O)—, and —$NR_3$—$C_{1-6}$alkyl-;

$X_2$ is selected from —O—$C_{1-6}$alkyl-, —(C=O)—$NR_2$—, and —$NR_2$—$C_{1-6}$alkyl-;

Y is selected from a direct bond, —O—, —S—, and —$NR_5$—;

$Het_1$, $Het_2$, $Het_3$, $Het_4$ and $Het_5$ are each independently selected from -morpholinyl, -piperidinyl, -piperazinyl, and pyrrolidinyl, wherein each heterocycle is optionally substituted with from 1 to 3 —$C_{1-6}$alkyl;

$Z_1$, $Z_2$, $Z_3$, $Z_4$ and $Z_5$ are each independently selected from C and N m and n are each independently 1, 2, 3, or 4.

6. A compound as defined in statement 1, wherein $A_1$ and $A_2$ are selected from C and N; wherein when $A_1$ is C, than $A_2$ is N; and wherein when $A_2$ is C, than $A_1$ is N $R_1$ is selected from —H, -halo, —$CF_3$, —$OCH_3$, and —(C=O)—$R_4$;

$R_7$ is —H;

$R_2$ is selected from —H, —$C_{2-4}$alkyl, —(C=O)—O—$C_{2-4}$alkyl, and —(C=O)-$Het_3$; wherein each of said $O_{2-4}$alkyl is optionally and independently substituted with from 1 to 3 substituents selected from —OH, —$OCH_3$, -$Het_3$, and —$NR_{13}R_{14}$;

$R_3$ is selected from —H, —$C_{1-2}$alkyl, and —(C=O)-$Het_2$; wherein each of said $C_{1-2}$alkyl is optionally and independently substituted with from 1 to 3 —OH;

$R_4$ is selected from —OH, —$OCH_3$, —$NR_{17}R_{18}$, and -$Het_4$;

$R_5$ is selected from —H, —$C_{1-3}$alkyl, and —$C_{3-6}$cycloalkyl; wherein each $C_{1-3}$alkyl is optionally substituted with from 1 to 3 substituents selected from —OH, and -$Het_5$;

$R_{13}$ and $R_{14}$ are —$CH_3$;

$R_{17}$ and $R_{18}$ are each independently selected from —H, —$CH_3$, and -$Het_1$;

$R_{19}$ and $R_{20}$ are each —O;

$X_1$ is selected from —$C_{1-6}$alkyl-, —O—$C_{2-6}$alkyl-, —$NR_3$—(C=O)—, and —$NR_3$—$C_{2-3}$alkyl-;

$X_2$ is selected from —O—$C_2$alkyl-, —(C=O)—$NR_2$—, and —$NR_2$—$C_{1-3}$alkyl-;

Y is selected from a direct bond, —O—, —S—, and —$NR_5$—;

$Het_1$, $Het_2$, $Het_3$, $Het_4$ and $Het_5$ are each independently selected from -morpholinyl, -piperidinyl, -piperazinyl, and pyrrolidinyl, wherein each heterocycle is optionally substituted with from 1 to 3 —$CH_3$;

$Z_1$, $Z_2$, $Z_3$, $Z_4$ and $Z_5$ are each independently selected from C and N m and n are each independently 1, 2, 3, or 4.

7. A compound as defined in statement 1, wherein $A_1$ and $A_2$ are selected from C and N; wherein when $A_1$ is C, than $A_2$ is N; and wherein when $A_2$ is C, than $A_1$ is N;

$R_1$ is selected from —H, -halo, —$CF_3$, —$OCH_3$, —(C=O)—OH, —(C=O)—$OCH_3$, —(C=O)-$Het_4$, —(C=O)—NH-$Het_4$, —(C=O)—$NH_2$, and —(C=O)—NH—$CH_3$;

$R_7$ is —H;

$R_2$ is selected from —H, —$C_{2-4}$alkyl, —(C=O)—O—$C_2$alkyl, and —(C=O)-$Het_3$; wherein each $C_{2-4}$alkyl is optionally and independently substituted with 1 substituent selected from —OH, —$OCH_3$, -$Het_3$, and —$NR_{13}R_{14}$;

$R_3$ is selected from —H, —$C_{1-2}$alkyl, and —(C=O)-$Het_2$; wherein said $C_{1-2}$alkyl is optionally and independently substituted with 1 —OH;

$R_5$ is selected from —H, —$C_{1-3}$alkyl, and —$C_{3-6}$cycloalkyl; wherein each $C_{1-3}$alkyl is optionally and independently substituted with 1 to 3 substituents selected from —OH, and -$Het_5$;

$R_{13}$ and $R_{14}$ are —$CH_3$;

$X_1$ is selected from —$C_{1-6}$alkyl-, —O—$C_{2-6}$alkyl-, —$NR_3$—(C=O)—, and —$NR_3$—$C_2$alkyl-;

$X_2$ is selected from —O—$C_2$alkyl-, —(C=O)—$NR_2$—, and —$NR_2$—$C_{1-3}$alkyl-;

Y is selected from a direct bond, —O—, —S—, and —$NR_5$—;

$Ar_3$ is phenyl substituted with —$NO_2$;

$Het_2$ is -piperidinyl substituted with —$CH_3$;

$Het_3$ is selected from -morpholinyl, and -piperazinyl;

$Het_4$ is selected from -morpholinyl, -piperidinyl, and -piperazinyl; wherein said -piperidinyl and -piperazinyl are substituted with —$CH_3$;

$Het_5$ is selected from -morpholinyl, and -pyrrolidinyl;

$Z_1$, $Z_2$, $Z_3$, $Z_4$ and $Z_5$ are each independently selected from C and N m and n are each independently 1, 2, 3, or 4.

8. A compound as defined in statement 1, wherein $A_1$ and $A_2$ are selected from C and N; wherein when $A_1$ is C, then $A_2$ is N; and wherein when $A_2$ is C, then $A_1$ is N;

$R_1$ and $R_7$ are each independently selected from —H, -halo, —$C_{1-6}$alkyl, —O—$C_{1-6}$alkyl, and —(C=O)—$R_4$; wherein each of said $C_{1-6}$alkyl is optionally and independently substituted with from 1 to 3 substituents selected from -halo, and —OH;

$R_2$ is selected from —H, —$C_{1-6}$alkyl, —(C=O)—$NR_{27}R_{28}$, and —(C=O)-$Het_3$; wherein each of said $C_{1-6}$alkyl is optionally and independently substituted with from 1 to 3 substituents selected from -halo, —OH, and —$NR_{13}R_{14}$;

$R_3$ and $R_{35}$ are each independently selected from —H, —$C_{1-6}$alkyl, and —(C=O)-$Het_2$; wherein each of said $C_{1-6}$alkyl is optionally and independently substituted with —OH;

$R_4$ is independently selected from —OH, and —$NR_{17}R_{18}$;

$R_5$ is selected from —H -$C_{1-6}$alkyl, and —$C_{3-6}$cycloalkyl; wherein each of said $C_{1-6}$alkyl is optionally and independently substituted with from 1 to 3 substituents selected from -halo, —OH, —$OC_{1-6}$alkyl, -$Het_5$, and —$NR_{31}R_{32}$;

$R_{13}$, $R_{14}$, $R_{17}$, $R_{18}$, $R_{27}$, $R_{28}$, $R_{31}$, $R_{32}$ are each independently selected from —H, and —$C_{1-6}$alkyl; wherein each of said $C_{1-6}$alkyl is optionally and independently substituted with from 1 to 3 substituents selected from -halo, —$NR_{35}R_{36}$, and -$Het_7$;

$R_{35}$ and $R_{36}$ are each —$C_{1-6}$alkyl;

$X_1$ is selected from —O—$C_{1-6}$alkyl-, —$NR_3$—(C=O)—, and —$NR_3$—;

$X_2$ is selected from —O—$C_{1-6}$alkyl-, and —$NR_2$—;

Y is selected from a direct bond, —O—, and —$NR_5$—;

$Het_3$ is -piperazinyl $Het_2$ is -piperidinyl substituted with —$CH_3$;

$Het_5$ is selected from -morpholinyl and -pyrrolidinyl;

$Het_7$ is -pyrrolidinyl;

$Z_1$, $Z_2$, $Z_3$, $Z_4$ and $Z_5$ are each independently selected from C and N;

m and n are each independently 1, 2, 3, or 4.

9. A compound as defined in statement 1, wherein $A_1$ is N; and $A_2$ is C;

$R_1$ and $R_7$ are each independently selected from —H, —$C_{1-6}$alkyl, —O—$C_{1-6}$alkyl, and —(C=O)—$R_4$; wherein each of said $C_{1-6}$alkyl is optionally and independently substituted with from 1 to 3 substituents selected from -halo, and —OH;

$R_2$ is selected from —H, —$C_{1-6}$alkyl, —(C=O)—$NR_{27}R_{28}$; wherein each of said $C_{1-6}$alkyl is optionally and independently substituted with from 1 to 3 substituents selected from —OH;

$R_3$ and $R_{35}$ are each independently selected from —H, —$C_{1-6}$alkyl, and —(C=O)-$Het_2$; wherein each of said $C_{1-6}$alkyl is optionally and independently substituted with —OH;

$R_4$ is independently selected from —OH, and —$NR_{17}R_{18}$;
$R_5$ is selected from —H —$C_{1-6}$alkyl, and —$C_{3-6}$cycloalkyl; wherein each of said $C_{1-6}$alkyl is optionally and independently substituted with from 1 to 3 substituents selected from -halo, —OH, —$OC_{1-6}$alkyl, and -$Het_5$;
$R_{17}$, $R_{18}$, $R_{27}$, and $R_{28}$ are each independently selected from —H, and —$C_{1-6}$alkyl; wherein each of said $C_{1-6}$alkyl is optionally and independently substituted with from 1 to 3 substituents selected from —$NR_{35}R_{36}$, and -$Het_7$;
$R_{35}$ and $R_{36}$ are each —$C_{1-6}$alkyl;
$X_1$ is selected from —O—$C_{1-6}$alkyl-, —$NR_3$—(C=O)—, and —$NR_3$—;
$X_2$ is selected from —O—$C_{1-6}$alkyl-, and —$NR_2$—;
Y is selected from a direct bond, —O—, and —$NR_5$—;
$Het_2$ is -piperidinyl substituted with —$CH_3$;
$Het_5$ is selected from -morpholinyl and -pyrrolidinyl;
$Het_7$ is -pyrrolidinyl;
$Z_1$, $Z_2$, $Z_3$, $Z_4$ and $Z_5$ are each C;
m and n are each independently 1, 2, 3, or 4.

10. A compound as defined in any one of statements 1 to 9 wherein the pyrazolopyrimidine moiety is linked to the aryl or heteroaryl moiety at position $Z_4$ and wherein $R_7$ is linked to the aryl or heteroaryl moiety at position $Z_5$ in accordance with Formula I.

11. A compound as defined in any one of statements 1 to 10, for use as a human or veterinary medicine.

12. Use of a compound as defined in any one of statements 1 to 10 in the manufacture of a medicament for the treatment of cell proliferative disorders, such as cancer.

13. A pharmaceutical composition comprising a compound as defined in any one of statements 1 to 10, suitable for use as a human or veterinary medicine.

14. Use of a compound as defined in any one of statements 1 to 10, or a composition as defined in statement 13, suitable for inhibiting the activity of a kinase; in particular a FLT3 kinase.

15. Use of a compound as defined in any one of statements 1 to 10, or a composition as defined in statement 13, for the prevention and/or treatment of cell proliferative disorders, such as cancer.

16. A method for the prevention and/or treatment of cell proliferative disorders such as cancer; said method comprising administering to a subject in need thereof a compound according to any one of statements 1 to 9 or a composition as defined in statement 13.

Method of Treatment

Compounds of formula (I) a stereoisomer, tautomer, racemic, metabolite, pro- or predrug, salt, hydrate, N-oxide form, or solvate thereof, are inhibitors of FLT3 kinase activity and are thus believed to be of potential use in the treatment of hematological malignancies include leukemias, lymphomas (non-Hodgkin's lymphoma), Hodgkin's disease (also called Hodgkin's lymphoma), and myeloma- for instance, acute lymphocytic leukemia (ALL), acute myeloid leukemia (AML), acute promyelocytic leukemia (APL), chronic lymphocytic leukemia (CLL), chronic myeloid leukemia (CML), chronic neutrophilic leukemia (CNL), acute undifferentiated leukemia (AUL), anaplastic large-cell lymphoma (ALCL), prolymphocytic leukemia (PML), juvenile myelomonocytic leukemia (JMML), adult T-cell ALL, AML with trilineage myelodysplasia (AML/TMDS), mixed lineage leukemia (MLL), myelodysplastic syndromes (MDSs), myeloproliferative disorders (MPD), multiple myeloma, (MM) and myeloid sarcoma. The methods of the present invention can be utilized in a variety of settings, including, for example, in selecting the optimal treatment course for a patient, in predicting the likelihood of success when treating an individual patient with a particular treatment regimen, in assessing disease progression, in monitoring treatment efficacy, in determining prognosis for individual patients and in assessing predisposition of an individual to benefit from a particular therapy.

In the invention, particular preference is given to compounds of Formula I or any subgroup thereof that in the inhibition assay for FLT3 described below inhibit kinase activity with an $IC_{50}$ value of less than 10 µM, preferably less than 1 µM, most preferably less than 100 nM.

Said inhibition may be effected in vitro and/or in vivo, and when effected in vivo, is preferably effected in a selective manner, as defined above.

The term "FLT3 kinase-mediated condition" or "disease", as used herein, means any disease or other deleterious condition in which the FLT3 kinase is known to play a role. The term "FLT3 kinase-mediated condition" or "disease" also means those diseases or conditions that are alleviated by treatment with a FLT3 kinase inhibitor. Accordingly, another embodiment of the present invention relates to treating or lessening the severity of one or more diseases in which the FLT3 kinase is known to play a role.

For pharmaceutical use, the compounds of the invention may be used as a free acid or base, and/or in the form of a pharmaceutically acceptable acid-addition and/or base-addition salt (e.g. obtained with non-toxic organic or inorganic acid or base), in the form of a hydrate, solvate and/or complex, and/or in the form or a pro-drug or pre-drug, such as an ester. As used herein and unless otherwise stated, the term "solvate" includes any combination which may be formed by a compound of this invention with a suitable inorganic solvent (e.g. hydrates) or organic solvent, such as but not limited to alcohols, ketones, esters and the like. Such salts, hydrates, solvates, etc. and the preparation thereof will be clear to the skilled person; reference is for instance made to the salts, hydrates, solvates, etc. described in U.S. Pat. Nos. 6,372,778, 6,369,086, 6,369,087 and 6,372,733.

The pharmaceutically acceptable salts of the compounds according to the invention, i.e. in the form of water-, oil-soluble, or dispersible products, include the conventional non-toxic salts or the quaternary ammonium salts which are formed, e.g., from inorganic or organic acids or bases. Examples of such acid addition salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalene-sulfonate, nicotinate, oxalate, palmoate, pectinate, persulfate, 3-phenylpropionate, picrate, pivalate, propionate, succinate, tartrate, thiocyanate, tosylate, and undecanoate. Base salts include ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine, lysine, and so forth. In addition, the basic nitrogen-containing groups may be quaternized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl-bromides and others. Other pharmaceutically acceptable salts include the sulfate salt ethanolate and sulfate salts.

Generally, for pharmaceutical use, the compounds of the inventions may be formulated as a pharmaceutical preparation or pharmaceutical composition comprising at least one compound of the invention and at least one pharmaceutically acceptable carrier, diluent or excipient and/or adjuvant, and optionally one or more further pharmaceutically active compounds.

By means of non-limiting examples, such a formulation may be in a form suitable for oral administration, for parenteral administration (such as by intravenous, intramuscular or subcutaneous injection or intravenous infusion), for administration by inhalation, by a skin patch, by an implant, by a suppository, etc. Such suitable administration forms—which may be solid, semi-solid or liquid, depending on the manner of administration—as well as methods and carriers, diluents and excipients for use in the preparation thereof, will be clear to the skilled person; reference is again made to for instance U.S. Pat. Nos. 6,372,778, 6,369,086, 6,369,087 and 6,372,733, as well as to the standard handbooks, such as the latest edition of Remington's Pharmaceutical Sciences.

Some preferred, but non-limiting examples of such preparations include tablets, pills, powders, lozenges, sachets, cachets, elixirs, suspensions, emulsions, solutions, syrups, aerosols, ointments, creams, lotions, soft and hard gelatin capsules, suppositories, eye drops, sterile injectable solutions and sterile packaged powders (which are usually reconstituted prior to use) for administration as a bolus and/or for continuous administration, which may be formulated with carriers, excipients, and diluents that are suitable per se for such formulations, such as lactose, dextrose, sucrose, sorbitol, mannitol, starches, gum acacia, calcium phosphate, alginates, tragacanth, gelatin, calcium silicate, microcrystalline cellulose, polyvinylpyrrolidone, polyethylene glycol, cellulose, (sterile) water, methylcellulose, methyl- and propylhydroxybenzoates, talc, magnesium stearate, edible oils, vegetable oils and mineral oils or suitable mixtures thereof. The formulations can optionally contain other pharmaceutically active substances (which may or may not lead to a synergistic effect with the compounds of the invention) and other substances that are commonly used in pharmaceutical formulations, such as lubricating agents, wetting agents, emulsifying and suspending agents, dispersing agents, desintegrants, bulking agents, fillers, preserving agents, sweetening agents, flavoring agents, flow regulators, release agents, etc. The compositions may also be formulated so as to provide rapid, sustained or delayed release of the active compound(s) contained therein, for example using liposomes or hydrophilic polymeric matrices based on natural gels or synthetic polymers. In order to enhance the solubility and/or the stability of the compounds of a pharmaceutical composition according to the invention, it can be advantageous to employ α-, β- or γ-cyclodextrins or their derivatives. An interesting way of formulating the compounds in combination with a cyclodextrin or a derivative thereof has been described in EP-A-721,331. In particular, the present invention encompasses a pharmaceutical composition comprising an effective amount of a compound according to the invention with a pharmaceutically acceptable cyclodextrin.

In addition, co-solvents such as alcohols may improve the solubility and/or the stability of the compounds. In the preparation of aqueous compositions, addition of salts of the compounds of the invention can be more suitable due to their increased water solubility.

For local administration, the compounds may advantageously be used in the form of a spray, ointment or transdermal patch or another suitable form for topical, transdermal and/or intradermal administration.

More in particular, the compositions may be formulated in a pharmaceutical formulation comprising a therapeutically effective amount of particles consisting of a solid dispersion of the compounds of the invention and one or more pharmaceutically acceptable water-soluble polymers.

The term "a solid dispersion" defines a system in a solid state (as opposed to a liquid or gaseous state) comprising at least two components, wherein one component is dispersed more or less evenly throughout the other component or components. When said dispersion of the components is such that the system is chemically and physically uniform or homogenous throughout or consists of one phase as defined in thermodynamics, such a solid dispersion is referred to as "a solid solution". Solid solutions are preferred physical systems because the components therein are usually readily bioavailable to the organisms to which they are administered.

It may further be convenient to formulate the compounds in the form of nanoparticles which have a surface modifier adsorbed on the surface thereof in an amount sufficient to maintain an effective average particle size of less than 1000 nm. Suitable surface modifiers can preferably be selected from known organic and inorganic pharmaceutical excipients. Such excipients include various polymers, low molecular weight oligomers, natural products and surfactants. Preferred surface modifiers include nonionic and anionic surfactants.

Yet another interesting way of formulating the compounds according to the invention involves a pharmaceutical composition whereby the compounds are incorporated in hydrophilic polymers and applying this mixture as a coat film over many small beads, thus yielding a composition with good bio-availability which can conveniently be manufactured and which is suitable for preparing pharmaceutical dosage forms for oral administration. Materials suitable for use as cores in the beads are manifold, provided that said materials are pharmaceutically acceptable and have appropriate dimensions and firmness. Examples of such materials are polymers, inorganic substances, organic substances, and saccharides and derivatives thereof.

The preparations may be prepared in a manner known per se, which usually involves mixing at least one compound according to the invention with the one or more pharmaceutically acceptable carriers, and, if desired, in combination with other pharmaceutical active compounds, when necessary under aseptic conditions. Reference is again made to U.S. Pat. Nos. 6,372,778, 6,369,086, 6,369,087 and 6,372,733 and the further prior art mentioned above, as well as to the standard handbooks, such as the latest edition of Remington's Pharmaceutical Sciences.

The pharmaceutical preparations of the invention are preferably in a unit dosage form, and may be suitably packaged, for example in a box, blister, vial, bottle, sachet, ampoule or in any other suitable single-dose or multi-dose holder or container (which may be properly labeled); optionally with one or more leaflets containing product information and/or instructions for use. Generally, such unit dosages will contain between 1 and 1000 mg, and usually between 5 and 500 mg, of the at least one compound of the invention, e.g. about 10, 25, 50, 100, 200, 300 or 400 mg per unit dosage.

The compounds can be administered by a variety of routes including the oral, rectal, ocular, transdermal, subcutaneous, intravenous, intramuscular or intranasal routes, depending mainly on the specific preparation used and the condition to be treated or prevented, and with oral and intravenous administration usually being preferred. The at least one compound of the invention will generally be administered in an "effective amount", by which is meant any amount of a compound of Formula or any subgroup thereof that, upon suitable administration, is sufficient to achieve the desired therapeutic or prophylactic effect in the individual to which it is administered. Usually, depending on the condition to be prevented or treated and the route of administration, such an effective amount will usually be between 0.01 to 1000 mg per kilogram body weight day of the patient per day, more often between 0.1 and 500 mg, such as between 1 and 250 mg, for example about 5, 10, 20, 50, 100, 150, 200 or 250 mg, per kilogram body weight day of the patient per day, which may be administered as a single daily dose, divided over one or more daily doses, or essentially continuously, e.g. using a drip infusion. The amount(s) to be administered, the route of administration and the further treatment regimen may be determined by the treating clinician, depending on factors such as the age, gender and general condition of the patient and the nature and severity of the disease/symptoms to be treated. Reference is again made to U.S. Pat. Nos. 6,372,778, 6,369,086, 6,369,087 and 6,372,733 and the further prior art mentioned above, as well as to the standard handbooks, such as the latest edition of Remington's Pharmaceutical Sciences.

In accordance with the method of the present invention, said pharmaceutical composition can be administered separately at different times during the course of therapy or concurrently in divided or single combination forms. The present invention is therefore to be understood as embracing all such regimes of simultaneous or alternating treatment and the term "administering" is to be interpreted accordingly.

For an oral administration form, the compositions of the present invention can be mixed with suitable additives, such as excipients, stabilizers, or inert diluents, and brought by means of the customary methods into the suitable administration forms, such as tablets, coated tablets, hard capsules, aqueous, alcoholic, or oily solutions. Examples of suitable inert carriers are gum arabic, magnesia, magnesium carbonate, potassium phosphate, lactose, glucose, or starch, in particular, corn starch. In this case, the preparation can be carried out both as dry and as moist granules. Suitable oily excipients or solvents are vegetable or animal oils, such as sunflower oil or cod liver oil. Suitable solvents for aqueous or alcoholic solutions are water, ethanol, sugar solutions, or mixtures thereof. Polyethylene glycols and polypropylene glycols are also useful as further auxiliaries for other administration forms. As immediate release tablets, these compositions may contain microcrystalline cellulose, dicalcium phosphate, starch, magnesium stearate and lactose and/or other excipients, binders, extenders, disintegrants, diluents and lubricants known in the art.

When administered by nasal aerosol or inhalation, these compositions may be prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art. Suitable pharmaceutical formulations for administration in the form of aerosols or sprays are, for example, solutions, suspensions or emulsions of the compounds of the invention or their physiologically tolerable salts in a pharmaceutically acceptable solvent, such as ethanol or water, or a mixture of such solvents. If required, the formulation can also additionally contain other pharmaceutical auxiliaries such as surfactants, emulsifiers and stabilizers as well as a propellant.

For subcutaneous administration, the compound according to the invention, if desired with the substances customary therefore such as solubilizers, emulsifiers or further auxiliaries are brought into solution, suspension, or emulsion. The compounds of the invention can also be lyophilized and the lyophilizates obtained used, for example, for the production of injection or infusion preparations. Suitable solvents are, for example, water, physiological saline solution or alcohols, e.g. ethanol, propanol, glycerol, in addition also sugar solutions such as glucose or mannitol solutions, or alternatively mixtures of the various solvents mentioned. The injectable solutions or suspensions may be formulated according to known art, using suitable non-toxic, parenterally-acceptable diluents or solvents, such as mannitol, 1,3-butanediol, water, Ringers solution or isotonic sodium chloride solution, or suitable dispersing or wetting and suspending agents, such as sterile, bland, fixed oils, including synthetic mono- or diglycerides, and fatty acids, including oleic acid.

When rectally administered in the form of suppositories, these formulations may be prepared by mixing the compounds according to the invention with a suitable non-irritating excipient, such as cocoa butter, synthetic glyceride esters or polyethylene glycols, which are solid at ordinary temperatures, but liquefy and/or dissolve in the rectal cavity to release the drug.

In preferred embodiments, the compounds and compositions of the invention are used orally or parenterally.

The invention will now be illustrated by means of the following synthetic and biological examples, which do not limit the scope of the invention in any way.

EXAMPLES

A. Compound Synthesis and Physicochemical Properties

The compounds of this invention can be prepared by any of several standard synthetic processes commonly used by those skilled in the art of organic chemistry. The compounds are generally prepared from starting materials which are either commercially available or prepared by standard means obvious to those skilled in the art.

General Schemes:

In general the compounds of formula (I) can be prepared as shown in scheme 1 below wherein a pyrazolo[1,5-a]pyrimidine or a imidazo[2,1-f]pyridazine of formula (II) is converted by reaction with a compound of formula (III) into a compound of formula (IV), which is then reacted with a (hetero-)aryl of formula (V) to form a compound of formula (VI). The compound of formula (VI) can then be optionally deprotected if desired before cyclisation to form a compound of formula (VII). The compound of formula (VII) can be optionally converted into a compound of general formula (I).

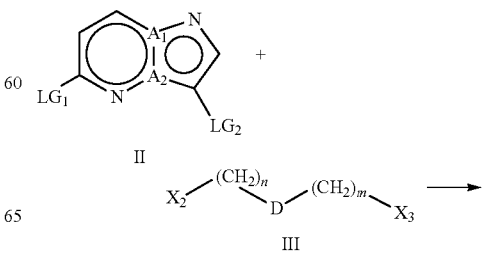

-continued

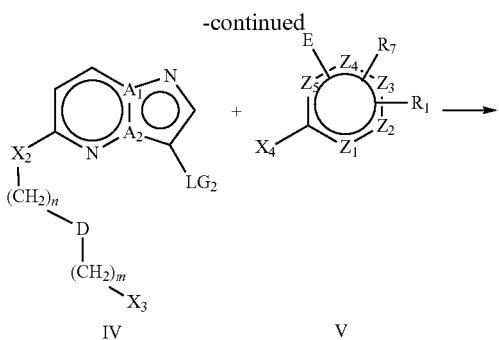

IV         V

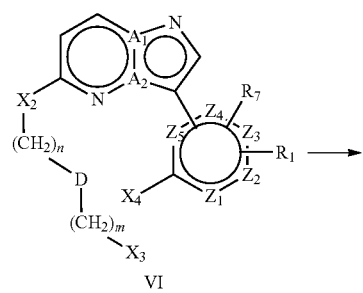

VI

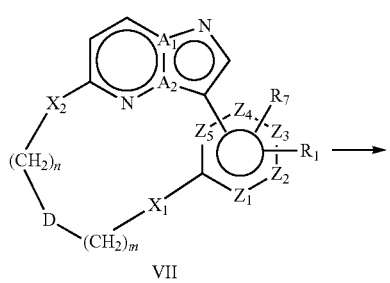

VII

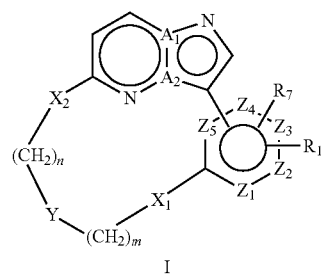

I

In the above scheme:

LG$_1$ and LG$_2$ each independently represent suitable leaving or functional groups;

X$_3$ and X$_4$ together with the functional moiety to which they are attached represent an unprotected or a protected functional group which upon reaction (after deprotection) produce together X$_1$ as defined in formula I;

E represents a suitable functional group that can be used to form a direct bond between the (hetero-)aryl group and the scaffold.

D represents a functional group such as Y or a protected functional group, which upon further reaction and/or deprotection produces a functional group such as Y as defined in formula I;

In the above reaction of the compound of formula (II) with the compound of formula (III) the leaving groups LG$_1$ and LG$_2$ are advantageously a halo group such as a chlorine or a bromine group. The reaction can be affected by a substitution for example by treating the compound of formula (II) with the compound of formula (III) in an organic solvent such as acetonitrile with an appropriate base such as for example diisopropylethylamine at an elevated temperature for example under reflux.

Compounds of formula (III) can be obtained through various selective protection and deprotection steps. The protection reactions can be effected using for example isoindoline-1,3-dione in a solvent such as toluene at an elevated temperature for example reflux or it can be effected by using for example benzaldehyde in the presence of a reducing agent for example sodium triacetoxyborohydride in a solvent such as 1,2-dichloroethane at room temperature or it can be effected using for example tert-butyldimethylsilyl chloride and triethylamine in a solvent such as N,N-dimethylformamide at room temperature. The deprotection reaction can be effected in a conventional manner using for example hydrazine in a solvent such as ethanol at an elevated temperature for example under reflux.

The compound of formula (IV) can optionally be protected with a suitable protecting group such as a tert-butyloxycarbonylamino group in a conventional manner for example by treatment with tert-butoxycarbonyl anhydride in basic conditions using for example triethylamine and 4-(dimethylamino)pyridine in a solvent such as tetrahydrofurane at an elevated temperature such as under reflux.

The reaction of the resulting compound (IV) with a (hetero-)aryl compound of formula (V) is advantageously effected through the coupling of a boronic acid E or boronic ester E derivative of the (hetero-)aryl compound under Suzuki conditions using for example tetrakis(triphenylphosphine)palladium(0), 2-dicyclohexylphosphino-2',4',6'-triisopropylbiphenyl (Xphos) and potassium phosphate tribasic in a solvent mixture such as 1,4-dioxane/water at an elevated temperature for example under reflux.

The resulting compound of formula (VI) can optionally be treated to remove any desired protecting groups for example silyl ether groups such as tert-butyldimethylsilyl groups can be converted to the parent free hydroxy group. Such deprotection can be effected in a conventional manner for example using tetrabutylammonium fluoride in tetrahydrofuran at room temperature. The resulting compound of formula (VI) can also optionally be treated to remove any desired protecting groups for example benzyl groups can be removed in a conventional manner for example using hydrogen gas and palladium on activated charcoal (10%) in a solvent such as methanol at a temperature such as room temperature. The compound of formula (VI) can optionally be treated to remove any desired protecting groups for example tert-butyloxycarbonylamino groups can be converted to the parent free amino group. Such deprotection can be effected in a conventional manner for example by treatment under acidic conditions for example using a 4N acetyl chloride solution in a solvent such as methanol at for example room temperature.

The cyclisation of the compound of formula (VI) can be effected for example under Mitsunobu conditions using for example diisopropyl azodicarboxylate and triphenylphosphine in a solvent mixture such as 2-methyl-1,4-dioxane and toluene at an elevated temperature such as 90° C. The resulting compound of formula (VII) can optionally be treated to remove any desired protecting groups for example tert-butyloxycarbonylamino groups can be converted to the parent free amino group. Such deprotection can be effected in a conventional manner for example by treatment under acidic conditions for example using a 4N hydrochloric acid solution in methanol at room temperature.

The compounds of formula (I) can also be prepared as shown in general scheme 2 below wherein a pyrazolo[1,5-a]pyrimidine or a imidazo[2,1-f]pyridazine of formula (II) is converted by reaction with a compound of formula (VIII) into a compound of formula (IX). The compound of formula (IX) can be optionally converted into a compound of formula (IV) which is then reacted with a (hetero-)aryl of formula (V) to form a compound of formula (VI). The compound of formula (VI) can then be optionally deprotected if desired before cyclisation to form a compound of formula (VII). The compound of formula (VII) can be optionally converted into a compound of general formula (I).

Scheme 2

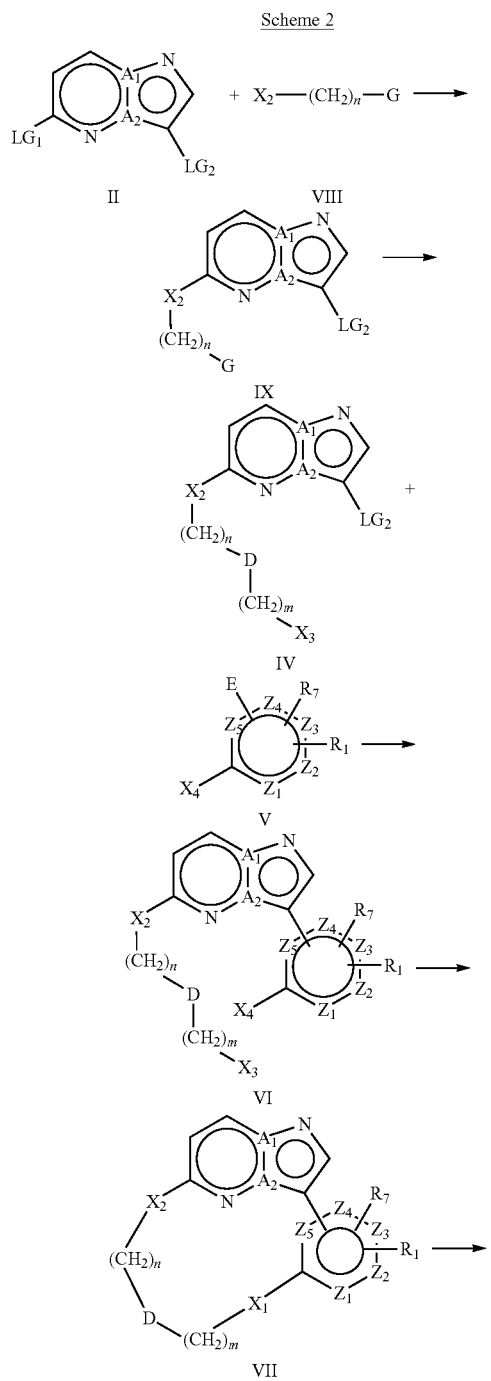

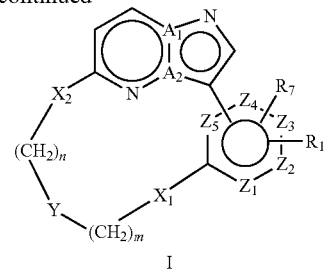

I

In the above scheme:
$LG_1$ and $LG_2$ each independently represent suitable leaving or functional groups;
E represents a suitable functional group that can be used to form a direct bond between the (hetero-)aryl group and the scaffold.
G represents a suitable functional group or protected functional group, which upon further reaction and/or deprotection produces a functional group such as D;
D represents a functional group such as B or a protected functional group, which upon further reaction and/or deprotection produces a functional group such as B as defined in formula I;

In the above reaction of the compound of formula (II) with the compound of formula (VIII) the leaving groups $LG_1$ and $LG_2$ are advantageously a halo group such as a chlorine or a bromine group. The reaction can be affected by a substitution for example by treating the compound of formula (II) with the compound of formula (VIII) in an organic solvent such as tetrahydrofuran with an appropriate base such as for example sodium hydride at for example room temperature.

Compounds of formula (VIII) can be either commercially acquired or obtained through various selective protection and deprotection steps.

The compounds of formula (IX) can be deprotected using for example acidic conditions such as a 4N hydrochloric acid solution in methanol at room temperature.

The compounds of formula (IX) can be converted into compounds of formula (IV) by using for example a reductive amination. The reaction can be affected by treating the compound of formula (IX) with an alhyde in the presence of a reducing agent such as sodium triacetoxy borohydride and a base such as triethylamine in a solvent such as dichloromethane at for example room temperature.

The reaction of the compound with formula (IV) with a (hetero-)aryl compound of formula (V) is advantageously effected under Suzuki conditions using for example tetrakis (triphenylphosphine)palladium(0) and potassium phosphate tribasic in a solvent mixture such as 1,4-dioxane/water at an elevated temperature for example 80° C.

The resulting compound of formula (VI) can optionally be treated to remove any desired protecting groups for example silyl ether groups such as tert-butyldimethylsilyl groups can be converted to the parent free hydroxy group. Such deprotection can be effected using for example acetic acid in tetrahydrofuran at for example room temperature. The compound of formula (VI) can optionally be treated to remove any desired protecting groups for example tert-butyloxycarbonylamino groups can be converted to the parent free amino group. Such deprotection can be effected in a conventional manner for example by treatment under acidic conditions for example using a 4N acetyl chloride solution in a solvent such as methanol at for example room temperature.

The free hydroxyl group can be converted into a leaving group such as a chloride by reacting the hydroxyl group for example with thionyl chloride in the presence of a base such as pyridine in a solvent such as dichloromethane at an elevated temperature for example under reflux.

The cyclisation of the compound of formula (VII) can be advantageously effected under Williamson conditions using a base such as cesium carbonate in a solvent such as N,N-dimethylformamide at an elevated temperature such as 90° C. Other condtions that can be used for the cyclisation of the compound of formula (VII) can be for example by treatment with O-(benzotriazol-1-yl)-N,N,N',N'-tetramethyluronium hexafluorophosphate (HBTU) and N,N-diisopropylethylamine in a solvent such as N,N-dimethylformamide at for example room temperature.

Conversion into B The resulting compound of formula (VII) can optionally be treated to form a compound of formula (I).

The above general processes are illustrated by the following specific processes which describe the preparation of the compounds of formula (I).

Experimental Part

In obtaining the compounds described in the examples, the following experimental protocols were followed unless otherwise indicated.

Unless otherwise stated, reaction mixtures were magnetically stirred at room temperature. Where solutions were "dried", they were generally dried over a drying agent such as sodium sulfate or magnesium sulfate. Where mixtures, solutions and extracts were "concentrated", they were typically concentrated on a rotary evaporator under reduced pressure.

For some compounds that were purified by reversed phase high-performance liquis chromatography (HPLC) the used method is described below (indicated in the compound procedure with HPLC method A. When necessary, these methods can be slightly adjusted by a person skilled in the art to obtain a more optimal result for the separation.

HPLC Method A

The crude product was purified by reverse phase HPLC, using a Gilson semi-preparative HPLC system operated by Gilson UNIPOINT software.

The purification was carried out on a Phenomenex Luna column (100 mm long×21.2 mm i.d.; 5 µm particles) at room temperature, with a constant flow rate of 20.0 mL/min. A gradient elution was performed from 32% (25 mM NH4HCO3 aqueous solution)/68% (Acetonitrile-Methanol 1:1) to 4% (25 mM NH4HCO3 aqueous solution)/96% (Acetonitrile-Methanol 1:1) in 20 minutes. The UV detector was set to 226 nm, which corresponds to the wavelength of maximum absorbance observed for the compound.

Preparation of the Compounds

Example 1

Example 1 is prepared following general scheme 1.

Preparation of Intermediate 1

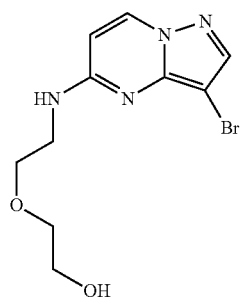 [SMILES: OCCOCCNc1ccn2ncc(Br)c2n1]

A mixture of 3-bromo-5-chloro-pyrazolo[1,5-a]pyrimidine (5.00 g, 21.51 mmol), 2-(2-aminoethoxy)ethanol (2.37 ml, 23.66 mmol) and N,N-diisopropylethylamine (4.50 ml, 25.81 mmol) in acetonitrile (65 ml) was refluxed overnight. The reaction mixture was cooled and the solvent was removed under reduced pressure. The residue was dissolved in ethyl acetate and washed with water and brine. The organic layer was dried, filtered and the solvent was removed under reduced pressure. The residue was purified by flash column chromatography over silica gel using heptane and ethyl acetate as eluents. The product fractions were collected and the solvent was evaporated.

LCMS method 1: MH$^+$=301, RT=0.586 min

Preparation of Intermediate 2

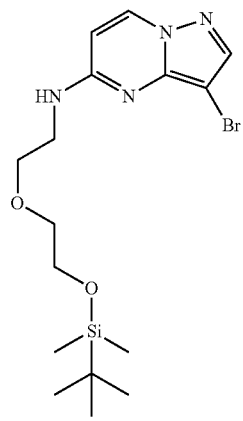 [SMILES: CC(C)(C)[Si](C)(C)OCCOCCNc1ccn2ncc(Br)c2n1]

Tert-butyldimethylsilyl chloride (4.86 g, 32.27 mmol) was added to a suspension of intermediate 1 (21.51 mmol) and triethylamine (5.96 ml, 43.02 mmol) in N,N-dimethylformamide (65 ml). The mixture was stirred at room temperature for 1 hour. The reaction mixture was diluted with ethyl acetate and washed with water and brine (3×). The organic layer was dried, filtered and the solvent was removed under reduced pressure. The product was used in the next step without further purification.

LCMS method 1: MH$^+$=417, RT=1.783 min

Preparation of Intermediate 3

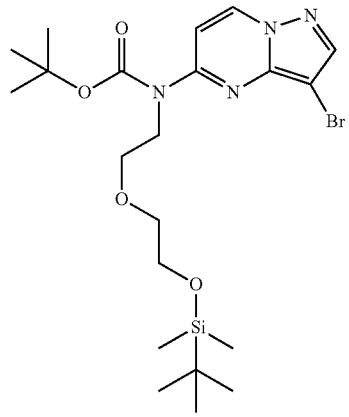 [SMILES: CC(C)(C)OC(=O)N(CCOCCO[Si](C)(C)C(C)(C)C)c1ccn2ncc(Br)c2n1]

A mixture of intermediate 2 (21.51 mmol), tert-butoxycarbonyl anhydride (5.16 g, 52.81 mmol), triethylamine (2.61 ml, 25.81 mmol) and 4-(dimethylamino)pyridine (53 mg, 0.43 mmol) in tetrahydrofurane (65 ml) was refluxed for 3 hours. The reaction mixture was cooled and the solvent was removed under reduced pressure. The residue was dissolved in ethyl acetate and washed with water and brine. The organic layer was dried, filtered and the solvent was removed under reduced pressure. The residue was purified by flash column chromatography over silica gel using heptane and ethyl acetate as eluents. The product fractions were collected and the solvent was evaporated.

Yield: 9.30 g of intermediate 3 (84%, yield over 3 steps)
LCMS method 1: MH$^+$=415 (MW-Boc), RT=2.438 min Preparation of Intermediate 4

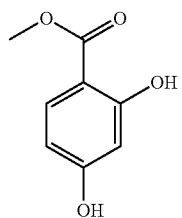

To a stirred solution of 2,4-dihydroxybenzoic acid (20.00 g, 129.77 mmol) in MeOH (100 ml) was added dropwise at 0° C. a solution of sulfuric acid (96%) in MeOH (290 ml). The reaction mixture was refluxed overnight. The reaction mixture was cooled and the solvent was removed under reduced pressure. The residue was dissolved in ethyl acetate and washed with brine. The organic layer was dried, filtered and the solvent was removed under reduced pressure. The residue was purified by flash column chromatography over silica gel using heptane and ethyl acetate as eluents. The product fractions were collected and the solvent was evaporated.

LCMS method 1: MH$^+$=169, RT=0.660 min

Preparation of Intermediate 5

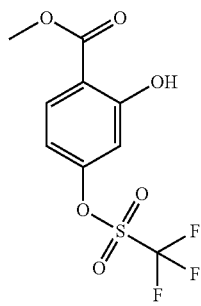 [SMILES: COC(=O)c1ccc(OS(=O)(=O)C(F)(F)F)cc1O]

Trifluoromethanesulfonic anhydride (5.97 ml, 35.32 mmol) was added dropwise at 0° C. under nitrogen atmosphere to a solution of intermediate 4 (5.40 g, 32.11 mmol) and triethylamine (8.90 ml, 64.22 mmol) in dichloromethane (96 ml). The mixture was allowed to warm up to room temperature. Water was added and the aqueous phase extracted with dichloromethane. The organic layers were combined, dried, filtered and the solvent was removed under reduced pressure. The residue was purified by flash chromatography over silica gel using heptane and ethyl acetate as eluents. The product fractions were collected and the solvent was evaporated.

Yield: 3.40 g of intermediate 5 (35%)
LCMS method 1: MH$^+$=301, RT=1.458 min

Preparation of Intermediate 6

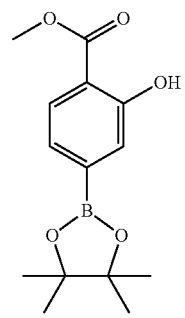 [SMILES: COC(=O)c1ccc(B2OC(C)(C)C(C)(C)O2)cc1O]

1,4-Dioxane (27 ml) was degassed by bubbling nitrogen gas through it. Intermediate 5 (2.75 g, 9.16 mmol), bis(pinacolato)diboron (2.33 g, 9.16 mmol), tris(dibenzylideneacetone)dipalladium(0) (82 mg, 0.09 mmol) and 2-(dicyclohexylphosphino)-2',4',6'-triisopropylbiphenyl (348 mg, 0.73 mmol) were added. The suspension was stirred under nitrogen atmosphere at 110° C. for 30 minutes. The reaction mixture was cooled and was used as such in the next step.

LCMS method 1: MH$^+$=279, RT=1.599 min

Preparation of Intermediate 7

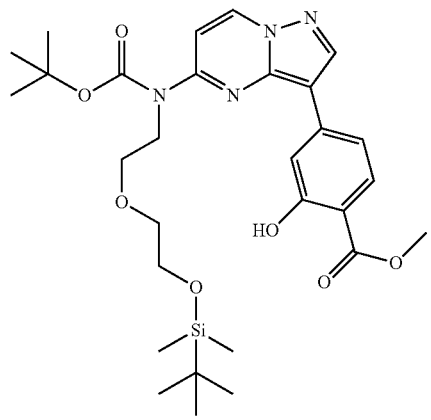 [SMILES: COC(=O)c1ccc(-c2cnn3ccc(N(CCOCCO[Si](C)(C)C(C)(C)C)C(=O)OC(C)(C)C)nc23)cc1O]

A solution of intermediate 3 (4.25 g, 8.24 mmol) in 1,4-dioxane (8.24 ml) and a solution of potassium phosphate (7.78 g, 36.64 mmol) in water (7.33 ml) were added to crude intermediate 6 (9.16 mmol). The mixture was stirred at 110° C. for 1 hour. The reaction mixture was cooled, diluted with ethyl acetate and the organic layer was washed with water and brine. The organic layer was dried, filtered and the solvent was removed under reduced pressure. The residue was purified by flash column chromatography over silica gel using heptane and ethyl acetate as eluents. The product fractions were collected and the solvent was evaporated.

Yield: 3.46 g of intermediate 7 (64%)
LCMS method 1: MH$^+$=487 (MW-Boc), RT=2.544 min

Preparation of Intermediate 8

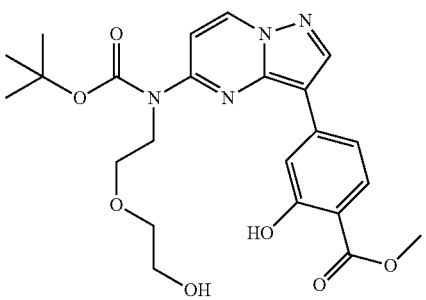 [SMILES: COC(=O)c1ccc(-c2cnn3ccc(N(CCOCCO)C(=O)OC(C)(C)C)nc23)cc1O]

A mixture of intermediate 7 (3.46 g, 5.90 mmol) and tetrabutylammonium fluoride (2.31 g, 8.85 mmol) in tetrahydrofuran (18 ml) was stirred at room temperature for 1 hour. The solvent was removed under reduced pressure, the residue was dissolved in ethyl acetate and washed with water (3×) and brine. The organic layer was dried, filtered and the solvent was removed under reduced pressure. The residue was purified by flash chromatography over silica gel using dichloromethane and methanol as eluents. The product fractions were collected and the solvent was evaporated.

LCMS method 1: $MH^+=473$, RT=1.425 min

Preparation of Intermediate 9

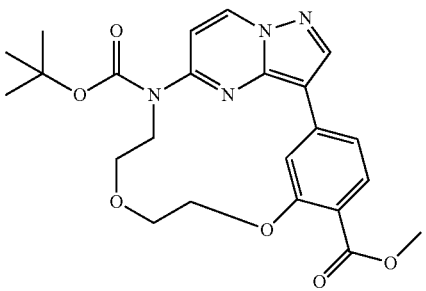 [SMILES: COC(=O)c1ccc2cc1OCCOCCN(C(=O)OC(C)(C)C)c1ccn3ncc-2c3n1]

A solution of intermediate 8 (2.45 g, 5.19 mmol) in 2-methyltetrahydrofuran (20 ml/mmol) and a solution of diisopropyl azodicarboxylate (3.09 g, 15.57 mmol) in toluene (20 ml/mmol) were added simultaneously to a solution of triphenylphosphine (4.08 g, 15.57 mmol) in toluene (75 ml/mmol). The mixture was stirred at 90° C. for 3 hours. The reaction mixture was cooled and the solvent was removed under reduced pressure. The residue was triturated in ethyl acetate and filtered to give the desired product.

Yield: 1.75 g of intermediate 9 (74%)
LCMS method 1: $MH^+=455$, RT=1.505 min

Preparation of Example 1

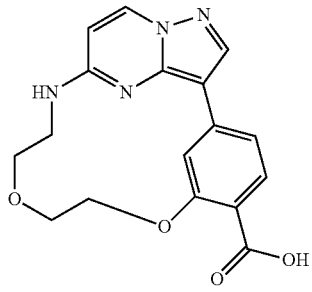 [SMILES: O=C(O)c1ccc2cc1OCCOCCNc1ccn3ncc-2c3n1]

Intermediate 9 (1.75 g, 3.85 mmol) and lithium hydroxide monohydrate (12.00 g, 11.55 mmol) were suspended in tetrahydrofuran/methanol (1:1, 12 ml). The mixture was stirred overnight at 50° C. The reaction mixture was cooled and 1N hydrochloric acid in water was added to obtain pH 3. The solvent was removed under reduced pressure and purified by flash chromatography on silica gel using dichloromethane and methanol as eluents. The product fractions were collected and the solvent was evaporated. The obtained solid was triturated in methanol to yield the desired product.

Yield: 705 mg of example 1 (54%)
LCMS method 1: $MH^+=341$, RT=0.696 min

Example 2

Example 2 is prepared following general scheme 1.

Preparation of Intermediate 10

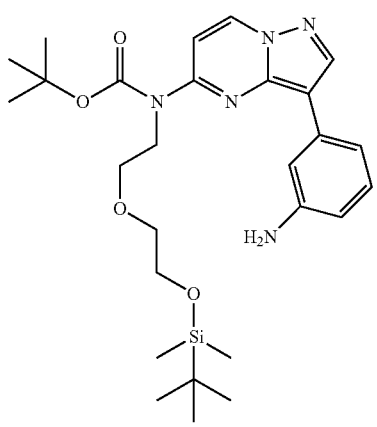 [SMILES: CC(C)(C)OC(=O)N(CCOCCO[Si](C)(C)C(C)(C)C)c1ccn2ncc(-c3cccc(N)c3)c2n1]

A mixture of 1,4-dioxane and water (3:1, 40 ml) was degassed by bubbling nitrogen gas through the mixture. Intermediate 3 (1.85 g, 3.59 mmol), (3-aminophenyl)boronic acid (0.72 g, 4.67 mmol), tetrakis(triphenylphosphine)palladium (0) (46 mg, 0.04 mmol), 2-dicyclohexylphosphino-2',4',6'-triisopropylbiphenyl (Xphos) (67 mg, 0.14 mmol) and potassium phosphate tribasic (5 eq.) were added and the mixture was stirred under nitrogen gas at 80° C. for 2 hours. The reaction mixture was cooled, diluted with ethyl acetate and the organic layer was washed with brine. The organic layer was dried, filtered and the solvent was removed under reduced pressure. The residue was purified by flash column chromatography over silica gel using heptane and ethyl acetate as eluents. The product fractions were collected and the solvent was evaporated.

Yield: 1.64 g of intermediate 10 (87%)
LCMS method 1: $MH^+=528$, RT=2.129 min

Preparation of Intermediate 11

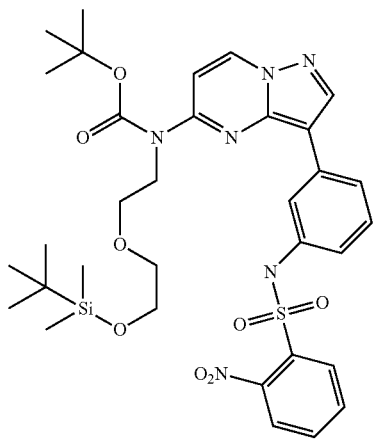 [SMILES: CC(C)(C)OC(=O)N(CCOCCO[Si](C)(C)C(C)(C)C)c1ccn2ncc(-c3cccc(NS(=O)(=O)c4ccccc4[N+](=O)[O-])c3)c2n1]

2-Nitrobenzenesulfonyl chloride (0.83 g, 3.73) mmol was added portionwise at 0° C. and under nitrogen atmosphere to a solution of intermediate 10 (1.64 g, 3.11 mmol), triethylamine (0.56 ml, 4.04 mmol) and 4-dimethylaminopyridine (20 mg, 0.16 mmol) in dichloromethane (20 ml). The reaction mixture was allowed to warm up to room temperature and stirred overnight. The crude reaction mixture was diluted with ethyl acetate and washed with a saturated aqueous sodium bicarbonate solution, water and brine. The organic layer was dried, filtered and the solvent was removed under reduced pressure. The residue was purified by flash column chromatography over silica gel using heptane and ethyl acetate as eluents. The product fractions were collected and the solvent was evaporated.

Yield: 1.32 g of intermediate 11 (55%)
LCMS method 1: MH$^+$=613 (MW-Boc), RT=2.328 min Preparation of Intermediate 12

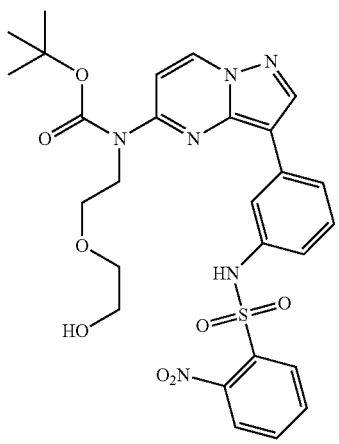 [SMILES: CC(C)(C)OC(=O)N(CCOCCO)c1ccn2ncc(-c3cccc(NS(=O)(=O)c4ccccc4[N+](=O)[O-])c3)c2n1]

A mixture of intermediate 11 (1.24 g, 1.73 mmol) and tetrabutylammonium fluoride (0.68 g, 2.59 mmol) in tetrahydrofuran (5 ml) was stirred at room temperature for 1 hour. The solvent was removed under reduced pressure, the residue was dissolved in ethyl acetate and washed with water (3×) and brine. The organic layer was dried, filtered and the solvent was removed under reduced pressure. The residue was used in the next step without further purification.

LCMS method 1: MH$^+$=599, RT=1.322 min

Preparation of Intermediate 13

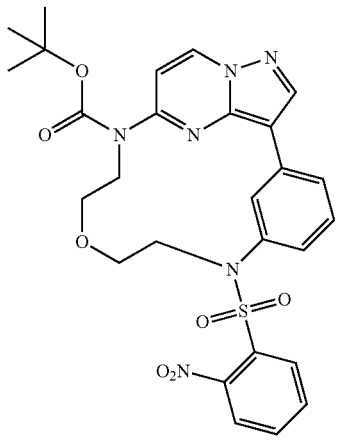 [SMILES: CC(C)(C)OC(=O)N1CCOCCN(S(=O)(=O)c2ccccc2[N+](=O)[O-])c2cccc(c2)-c2cnn3ccc1nc23]

A solution of intermediate 12 (1.13 g, 1.89 mmol) in 2-methyltetrahydrofuran (20 ml/mmol) and a solution of diisopropyl azodicarboxylate (1.12 g, 5.67 mmol) in toluene (20 ml/mmol) were added simultaneously to a solution of triphenylphosphine (1.49 g, 5.67 mmol) in toluene (75 ml/mmol). The mixture was stirred at 90° C. for 3 hours. The reaction mixture was cooled and the solvent was removed under reduced pressure. The residue was purified by flash column chromatography over silica gel using heptane and ethyl acetate as eluents. The product fractions were collected and the solvent was evaporated.

LCMS method 1: MH$^+$=581, RT=1.700 min

Preparation of Intermediate 14

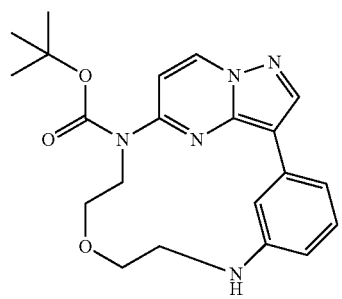 [SMILES: CC(C)(C)OC(=O)N1CCOCCNc2cccc(c2)-c2cnn3ccc1nc23]

Intermediate 13 (1.89 mmol) and cesium carbonate (1.23 g, 3.78 mmol) were suspended in N,N-dimethylformamide (6 ml). Thiophenol (230 µl, 2.27 mmol) was added and the mixture was stirred at room temperature for 2 hours. The reaction mixture was diluted with ethyl acetate and washed with brine. The organic layer was dried, filtered and the solvent was removed under reduced pressure. The residue was purified by flash column chromatography over silica gel using dichloromethane and methanol as eluents. The product fractions were collected and the solvent was evaporated.

Yield: 0.50 g of intermediate 14 (67%)
LCMS method 1: MH$^+$=396, RT=1.346 min

Preparation of Example 2

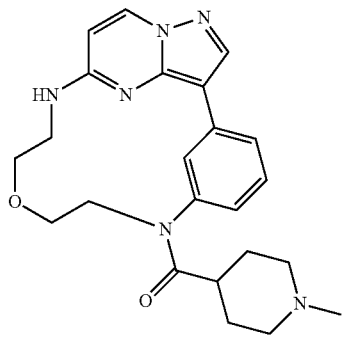 [SMILES: CN1CCC(C(=O)N2CCOCCNc3ccn4ncc(c4n3)-c3cccc2c3)CC1]

Phosphorus trichloride (66 mg, 0.76 mmol) was added to a suspension of intermediate 14 (0.300 g, 0.76 mmol) and 1-methylpiperidine-4-carboxylic acid hydrochloride (0.15 g, 0.76 mmol) in acetonitrile (2.3 ml) in a sealed tube. The mixture was heated by microwave at 150° C. for 10 min. The reaction mixture was poured into a saturated aqueous sodium bicarbonate solution and extracted with dichloromethane (3×). The organic layer was dried, filtered and the solvent was removed under reduced pressure. The residue was purified by flash column chromatography over silica gel using dichloromethane and methanol as eluents. The product fractions were collected and the solvent was evaporated.

Yield: 210 g of example 2 (66%)
LCMS method 1: MH$^+$=421, RT=0.531 min

Example 3

Example 3 is prepared following general scheme 1.

Preparation of Intermediate 15

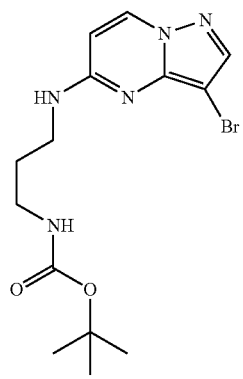 [SMILES: CC(C)(C)OC(=O)NCCCNc1ccn2ncc(Br)c2n1]

A mixture of 3-bromo-5-chloro-pyrazolo[1,5-a]pyrimidine (1.00 g, 4.30 mmol), tert-butyl N-(3-aminopropyl)carbamate (0.82 g, 4.73 mmol) and N,N-diisopropylethylamine (0.91 ml, 5.16 mmol) in acetonitrile (13 ml) was refluxed overnight. The reaction mixture was cooled and the solvent was removed under reduced pressure. The residue was dissolved in ethyl acetate and washed with water and brine. The organic layer was dried, filtered and the solvent was removed under reduced pressure. The residue was purified by flash column chromatography over silica gel using heptane and ethyl acetate as eluents. The product fractions were collected and the solvent was evaporated.

Yield: 1.58 g of intermediate 15 (99%)

LCMS method 1: $MH^+$=372, RT=1.104 min

Preparation of Intermediate 16

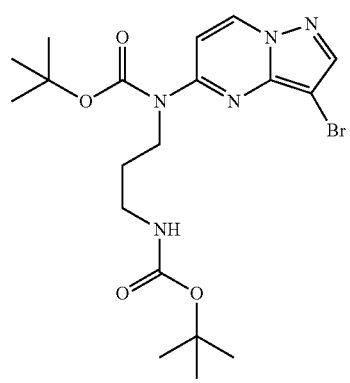 [SMILES: CC(C)(C)OC(=O)NCCCN(C(=O)OC(C)(C)C)c1ccn2ncc(Br)c2n1]

A mixture of intermediate 15 (1.58 g, 4.27 mmol), tert-butoxycarbonyl anhydride (0.98 g, 4.48 mmol), triethylamine (0.68 ml, 4.91 mmol) and 4-(dimethylamino)pyridine (26 mg, 0.21 mmol) in tetrahydrofuran (13 ml) was refluxed for 2 hours. The reaction mixture was cooled and the solvent was removed under reduced pressure. The residue was dissolved in ethyl acetate and washed with water and brine. The organic layer was dried, filtered and the solvent was removed under reduced pressure. The residue was used in the next step without further purification.

LCMS method 1: $MH^+$=370 (MW-Boc), RT=1.712 min

Preparation of Intermediate 17

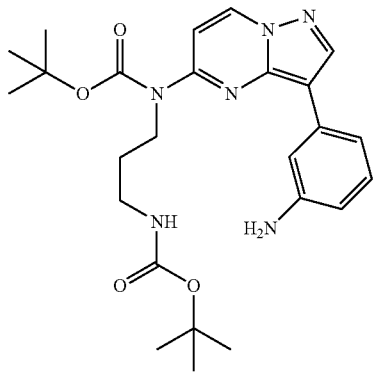 [SMILES: CC(C)(C)OC(=O)NCCCN(C(=O)OC(C)(C)C)c1ccn2ncc(-c3cccc(N)c3)c2n1]

A mixture of 1,4-dioxane and water (3:1, 7.6 ml) was degassed by bubbling nitrogen gas through the mixture. Intermediate 16 (1.18 g, 2.52 mmol), (3-aminophenyl)boronic acid (0.47 g, 3.02 mmol), tetrakis(triphenylphosphine)palladium(0) (35 mg, 0.03 mmol), 2-dicyclohexylphosphino-2',4',6'-triisopropylbiphenyl (Xphos) (48 mg, 0.10 mmol) and potassium phosphate tribasic (5 eq.) were added and the mixture was stirred under nitrogen gas at 80° C. overnight. The reaction mixture was cooled, diluted with ethyl acetate and the organic layer was washed with brine. The organic layer was dried, filtered and the solvent was removed under reduced pressure. The residue was purified by flash column chromatography over silica gel using heptane and ethyl acetate as eluents. The product fractions were collected and the solvent was evaporated.

Yield: 1.04 g of intermediate 17 (86% over 2 steps)

LCMS method 1: $MH^+$=483, RT=1.379 min

Preparation of Intermediate 18

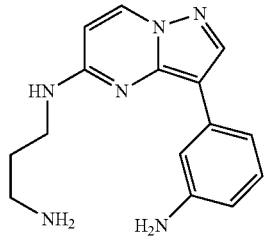 [SMILES: NCCCNc1ccn2ncc(-c3cccc(N)c3)c2n1]

Intermediate 17 (1.04 g, 2.16 mmol) was dissolved in 4N hydrochloric acid in methanol (20 ml). The mixture was stirred at room temperature overnight. The reaction mixture was diluted with ethyl acetate and the organic layer was washed with a saturated aqueous sodium bicarbonate solution. The organic layer was dried, filtered and the solvent was removed under reduced pressure. The residue was purified by flash column chromatography over silica gel using dichloromethane and methanol with ammonia as eluents. The product fractions were collected and the solvent was evaporated.

Yield: 0.40 g of intermediate 17 (66%)

LCMS method 1: $MH^+$=283, RT=0.194 min

Preparation of Example 3

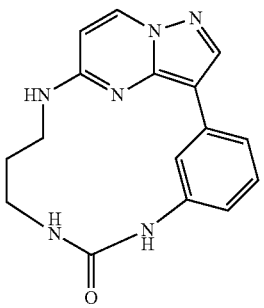 [SMILES: O=C1NCCCNc2ccn3ncc(c3n2)-c2cccc(c2)N1]

Triphosgene (10 mg, 0.05 mmol) was added to a solution of intermediate 17 (50 mg, 0.18 mmol) in dichloromethane (0.54 ml). The reaction mixture was stirred at room temperature for 3 hours. The reaction mixture was diluted with dichloromethane and the organic layer was washed with water. The organic layer was dried, filtered and the solvent was removed under reduced pressure. The residue was purified by reversed phase column chromatography (HPLC method A).
Yield: 7 mg of Example 3 (13%)
LCMS method 2: MH$^+$=309, RT=2,181 min

Example 4

Example 4 is prepared following general scheme 1.

Preparation of Intermediate 18

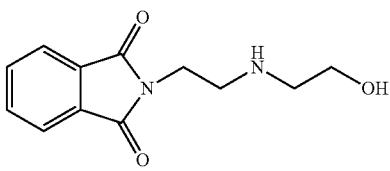 [SMILES: O=C1c2ccccc2C(=O)N1CCNCCO]

A mixture of 2-(2-aminoethylamino)ethanol (14.56 g, 139.80 mmol) and isoindoline-1,3-dione (20.16 g, 137.00 mmol) in toluene (420 ml) was refluxed for 3 hours. The solvent was removed under reduced pressure and the residue was used in the next step without further purification.
LCMS method 1: MH$^+$=235, RT=0.181 min

Preparation of Intermediate 19

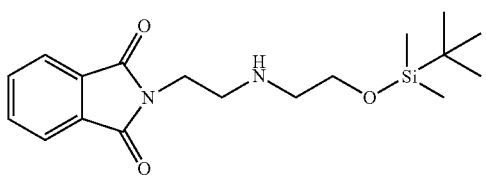 [SMILES: CC(C)(C)[Si](C)(C)OCCNCCN1C(=O)c2ccccc2C1=O]

Tert-butyldimethylsilyl chloride (31.0 g, 205.5 mmol) was added to a suspension of intermediate 18 (32.0 g, 137.0 mmol) and triethylamine (38.0 ml, 274.0 mmol) in N,N-dimethylformamide (411 ml). The mixture was stirred overnight at room temperature. The reaction mixture was diluted with ethyl acetate and washed with water and brine (3×). The organic layer was dried, filtered and the solvent was removed under reduced pressure. The residue was purified by flash column chromatography using heptane and ethyl acetate as eluents. The product fractions were collected and the solvent was evaporated.
Yield: 16.6 g of intermediate 19 (35%)
LCMS method 1: MH$^+$=349, RT=0.728 min

Preparation of Intermediate 20

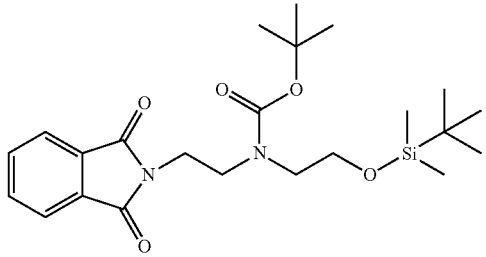 [SMILES: CC(C)(C)OC(=O)N(CCO[Si](C)(C)C(C)(C)C)CCN1C(=O)c2ccccc2C1=O]

Tert-butoxycarbonyl anhydride (4.3 g, 19.6 mmol) was added to a mixture of intermediate 19 (6.5 g, 18.6 mmol) and triethylamine (3.1 ml, 22.4 mmol) in tetrahydrofuran (56 ml). The reaction mixture was stirred for 1 hour and the solvent was removed under reduced pressure. The residue was dissolved in ethyl acetate and washed with water and brine (3×). The organic layer was dried, filtered and the solvent was removed under reduced pressure. Intermediate 3 was used in the next step without further purification.
Yield: 6.0 g of intermediate 20 (72%)
LCMS method 1: MH$^+$=349 (MW-Boc), RT=2.185 min

Preparation of Intermediate 21

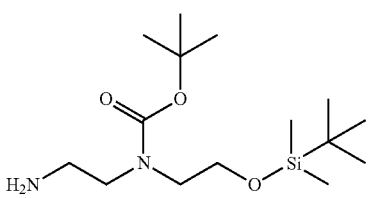

A mixture of intermediate 20 (6.0 g, 13.4 mmol) and hydrazine (1.2 ml, 40.1 mmol) was stirred overnight at 60° C. The reaction mixture was cooled, filtered and the solvent was removed under reduced pressure. The residue was dissolved in ethyl acetate and washed with 1N sodium hydroxide and water. The organic layer was dried, filtered and the solvent was removed under reduced pressure. Intermediate 4 was used in the next step without further purification.
Yield: 3.8 g of intermediate 21 (89%)
LCMS method 1: MH$^+$=319, RT=0.948 min Preparation of Intermediate 22

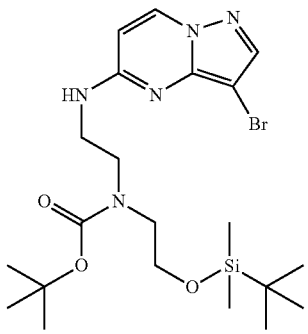 [SMILES: CC(C)(C)OC(=O)N(CCNc1ccn2ncc(Br)c2n1)CCO[Si](C)(C)C(C)(C)C]

A mixture of 3-bromo-5-chloro-pyrazolo[1,5-a]pyrimidine (2.5 g, 10.7 mmol), intermediate 21 (3.8 g, 11.8 mmol) and N,N-diisopropylethylamine (2.2 ml, 12.9 mmol) in acetonitrile (32 ml) was refluxed overnight. The reaction mixture was cooled and the solvent was removed under reduced pressure. The residue was dissolved in ethyl acetate and washed with water and brine. The organic layer was dried, filtered and the solvent was removed under reduced pressure. The residue was purified by flash column chromatography over silica gel using heptane and ethyl acetate as eluents. The product fractions were collected and the solvent was evaporated.

Yield: 4.7 g of intermediate 22 (84%)
LCMS method 1: MH$^+$=516, RT=2.154 min

Preparation of Intermediate 23

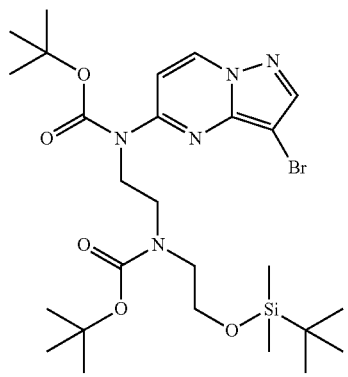 [SMILES: CC(C)(C)OC(=O)N(CCO[Si](C)(C)C(C)(C)C)CCN(C(=O)OC(C)(C)C)c1ccn2ncc(Br)c2n1]

A mixture of intermediate 22 (4.7 g, 9.1 mmol), tert-butoxycarbonyl anhydride (2.1 g, 9.5 mmol), triethylamine (1.4 ml, 10.0 mmol) and 4-(dimethylamino)pyridine (0.05 g, 0.45 mmol) in tetrahydrofuran (27 ml) was refluxed overnight. The reaction mixture was cooled and the solvent was removed under reduced pressure. The residue was dissolved in ethyl acetate and washed with water and brine. The organic layer was dried, filtered and the solvent was removed under reduced pressure. The residue was purified by flash column chromatography over silica gel using heptane and ethyl acetate as eluents. The product fractions were collected and the solvent was evaporated.

Yield: 5.2 g of intermediate 23 (92%)
LCMS method 1: MH$^+$=516 (MW-Boc), RT=2.615 min Preparation of Intermediate 24

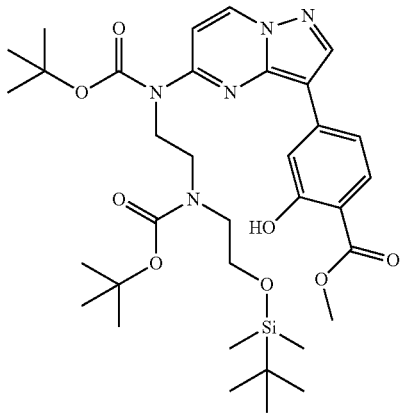 [SMILES: COC(=O)c1ccc(-c2cnn3ccc(N(CCN(CCO[Si](C)(C)C(C)(C)C)C(=O)OC(C)(C)C)C(=O)OC(C)(C)C)nc23)cc1O]

A mixture of 1,4-dioxane and water (3:1, 62 ml) was degassed by bubbling nitrogen gas through the mixture. Intermediate 23 (3.83 g, 6.23 mmol), methyl 2-hydroxy-4-(4,4,5,5-tetramethyl-1,3,2-dioxaborolan-2-yl)benzoate (2.25 g, 8.10 mmol), tris(dibenzylideneacetone)dipalladium(0) (55 mg, 0.06 mmol), 2-dicyclohexylphosphino-2',4',6'-triisopropylbiphenyl (Xphos) (119 mg, 0.25 mmol) and potassium phosphate tribasic (5.28 g, 4 eq.) were added and the mixture was stirred under nitrogen gas at 80° C. for 2 hours. The reaction mixture was cooled, diluted with ethyl acetate and the organic layer was washed with brine. The organic layer was dried, filtered and the solvent was removed under reduced pressure. The residue was purified by flash column chromatography over silica gel using heptane and ethyl acetate as eluents. The product fractions were collected and the solvent was evaporated.

Yield: 1.88 g of intermediate 24 (44%)
LCMS method 1: MH$^+$=572 (MW-Me-Boc), RT=2.303 min Preparation of Intermediate 25

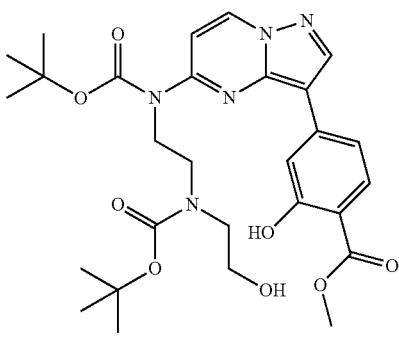 [SMILES: COC(=O)c1ccc(-c2cnn3ccc(N(CCN(CCO)C(=O)OC(C)(C)C)C(=O)OC(C)(C)C)nc23)cc1O]

A mixture of intermediate 24 (1.88 g, 2.74 mmol) and tetrabutylammonium fluoride (1.07 g, 4.11 mmol) in tetrahydrofuran (8 ml) was stirred at room temperature for 1 hour.

The solvent was removed under reduced pressure. The residue was purified by flash column chromatography over silica gel using heptane and ethyl acetate as eluents. The product fractions were collected and the solvent was evaporated.

Yield: 1.51 g of intermediate 25 (96%)
LCMS method 1: MH$^+$=472 (MW-Boc, RT=1.691 min Preparation of Intermediate 26

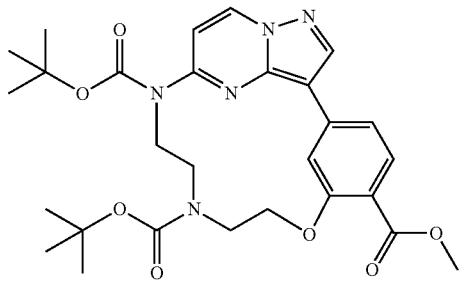 [SMILES: COC(=O)c1ccc2cc1OCCN(C(=O)OC(C)(C)C)CCN(C(=O)OC(C)(C)C)c1ccn3ncc-2c3n1]

A solution of intermediate 25 (1.51 g, 2.64 mmol) in 2-methyltetrahydrofuran (20 ml/mmol) and a solution of diisopropyl azodicarboxylate (1.57 g, 7.92 mmol) in toluene (20 ml/mmol) were added simultaneously to a solution of triphenylphosphine (2.08 g, 7.92 mmol) in toluene (75 ml/mmol). The mixture was stirred at 90° C. for 3 hours. The reaction mixture was cooled and the solvent was removed under reduced pressure. The residue was purified by flash column chromatography over silica gel using heptane and ethyl acetate as eluents. The product fractions were collected and the solvent was evaporated. The residue was triturated in methanol and filtered to give the desired product.

Yield: 0.60 g of intermediate 26 (41%)
LCMS method 1: MH$^+$=454 (MW-Boc), RT=2.031 min Preparation of Intermediate 27

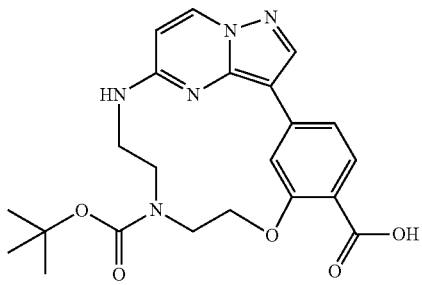 [SMILES: CC(C)(C)OC(=O)N1CCNc2ccn3ncc(c3n2)-c2ccc(C(=O)O)c(c2)OCC1]

Intermediate 26 (0.60 g, 1.08 mmol) and lithium hydroxide monohydrate (0.23 g, 3.24 mmol) were suspended in tetrahydrofuran/methanol (1:1, 3 ml). The mixture was stirred overnight at 50° C. The reaction mixture was cooled and the solvent was removed under reduced pressure and purified by flash chromatography on silica gel using dichloromethane and methanol as eluents. The product fractions were collected and the solvent was evaporated.

Preparation of Intermediate 28

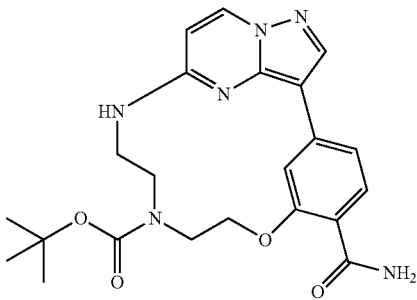 [SMILES: CC(C)(C)OC(=O)N1CCNc2ccn3ncc(c3n2)-c2ccc(C(N)=O)c(c2)OCC1]

Intermediate 27 (1.08 mmol), ammonium chloride (0.13 g, 2.38 mmol) and N,N-diisopropylethylamine (0.5 ml, 2.81 mmol) were dissolved in N,N-dimethylformamide (3 ml). O-(benzotriazol-1-yl)-NN,N',N'-tetramethyluronium hexafluorophosphate (HBTU) (0.98 g, 2.59 mmol) was added and the reaction mixture was stirred at room temperature for 1 hour. The mixture was poured into ethyl and washed with a saturated aqueous sodium bicarbonate solution, water and brine. The organic layer was dried, filtered and the solvent was removed under reduced pressure. The residue was triturated in hot methanol, cooled and filtered to give the desired product.

Yield: 392 mg of intermediate 28 (83% over 2 steps)
LCMS method 1: MH$^+$=439, RT=1.003 min Preparation of Example 4

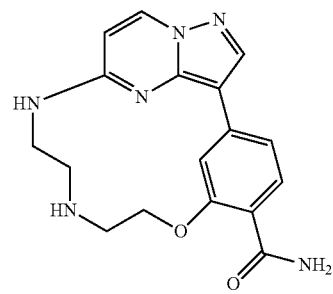 [SMILES: NC(=O)c1ccc2cc1OCCNCCNc1ccn3ncc-2c3n1]

Intermediate 28 (0.39 g, 0.89 mmol) was dissolved in 4N hydrochloric acid in methanol (3 ml). The mixture was stirred at room temperature for 2 hours. The solvent was removed under reduced pressure. The resulting solid was triturated in methanol, filtered and washed with methanol to yield the desired product.

Yield: 325 mg of example 4 (97%)
LCMS method 2: MH$^+$=339, RT=1.254 min

Example 5

Example 5 is prepared following general scheme 1.
Example 5 is prepared according to the same methods as for the synthesis of Example 4 using (3-hydroxyphenyl)boronic acid for the Suzuki coupling.

Preparation of Example 5

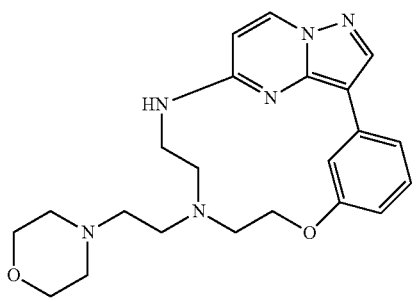 [SMILES: c1cc2cc(c1)-c1cnn3ccc(nc13)NCCN(CCN1CCOCC1)CCO2]

7-Oxa-10,13,17,18,21-pentaazatetracyclo[12.5.2.1^{2,6}.0^{17,20}]docosa-(20),2,4,6(22),14(21), -15,18-heptaene (200 mg, 0.60 mmol) and triethylamine (0.291 ml, 2.10 mmol) were dissolved in a mixture of 1,2-dichloroethane and methanol (1:1, 5 ml). 2-Morpholinoacetaldehyde (0.12 g, 0.72 mmol) was added and the mixture was stirred at room temperature for 30 minutes. Sodium triacetoxyborohydride (254 mg, 1.20 mmol) was added and the mixture was stirred at room temperature until the reaction was completed (TLC). The reaction mixture was poured into ethyl acetate and the organic layer was washed with a saturated aqueous sodium bicarbonate solution and brine. The organic layer was dried, filtered and the solvent was removed under reduced pressure. The residue was purified by flash column chromatography over silica gel using dichloromethane and methanol as eluents. The product fractions were collected and the solvent was evaporated.

Yield: 163 mg of example 5 (66%)
LCMS method 1: MH$^+$=409, RT=0.606 min

Example 6

Example 6 is prepared following general scheme 1.
Example 6 is prepared according to the same methods used for the synthesis of Example 5.

Preparation of Example 6

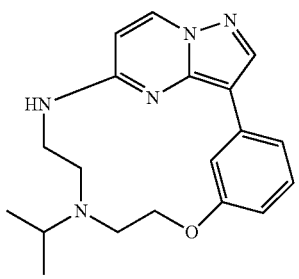 [SMILES: CC(C)N1CCNc2ccn3ncc(c3n2)-c2cccc(c2)OCC1]

7-Oxa-10,13,17,18,21-pentaazatetracyclo[12.5.2.1^{2,6}.0^{17,20}]docosa-(20),2,4,6(22),14(21), -15,18-heptaene (200 mg, 0.60 mmol) and triethylamine (0.208 ml, 1.50 mmol) were dissolved in a mixture of 1,2-dichloroethane and methanol (1:1, 5 ml). Acetone (0.05 ml, 0.72 mmol) was added and the mixture was stirred at room temperature for 30 minutes. Sodium triacetoxyborohydride (254 mg, 1.20 mmol) was added and the mixture was stirred at room temperature until the reaction was completed (TLC). The reaction mixture was poured into ethyl acetate and the organic layer was washed with a saturated aqueous sodium bicarbonate solution and brine. The organic layer was dried, filtered and the solvent was removed under reduced pressure. The residue was purified by flash column chromatography over silica gel using dichloromethane and methanol as eluents. The product fractions were collected and the solvent was evaporated.

Yield: 148 mg of example 6 (73%)
LCMS method 1: MH$^+$=338, RT=0.555 min

Example 7

Example 7 is prepared following general scheme 1.

Preparation of Intermediate 29

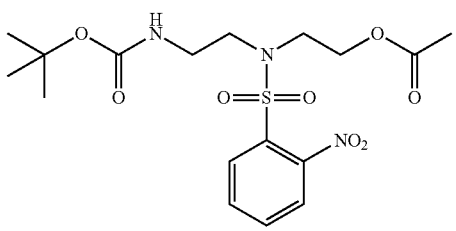 [SMILES: CC(=O)OCCN(CCNC(=O)OC(C)(C)C)S(=O)(=O)c1ccccc1[N+](=O)[O-]]

To a solution of tert-butyl N-[2-(benzenesulfonamido)ethyl]carbamate (21.70 g, 62.83 mmol) in N,N-dimethylformamide (189 ml) were added 2-bromoethyl acetate (11.54 g, 69.11 mmol) and cesium carbonate (26.60 g, 75.39 mmol). The mixture was stirred overnight at 50° C. Water was added and the product was extracted with ethyl acetate. The organic layer was dried, filtered and the solvent was removed under reduced pressure. The product was used without further purification in the next step.

LCMS method 1: MH$^+$=332 (MW-Boc), RT=1.151 min

Preparation of Intermediate 30

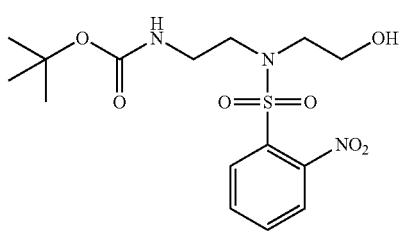 [SMILES: CC(C)(C)OC(=O)NCCN(CCO)S(=O)(=O)c1ccccc1[N+](=O)[O-]]

Sodium hydroxide (2.513 g, 62.83 mmol) was added to a solution of intermediate 29 (27.11 g, 62.83 mmol) in methanol/water (3:1, 188 ml). The mixture was stirred at room temperature for 90 minutes. The solvent was removed under reduced pressure, water was added and the product was extracted with ethyl acetate. The organic layer was dried, filtered and the solvent was removed under reduced pressure. The product was used without further purification in the next step.

LCMS method 1: MH$^+$=290 (MW-Boc), RT=0.956 min

Preparation of Intermediate 31

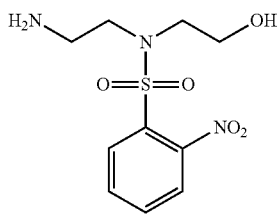 [SMILES: NCCN(CCO)S(=O)(=O)c1ccccc1[N+](=O)[O-]]

Intermediate 30 (62.83 mmol) was stirred in acetyl chloride (188 ml) at room temperature for 2 hours. The solvent was removed under reduced pressure. Toluene was added, stirred and removed under reduced pressure. The product was used without further purification in the next step.
LCMS method 1: $MH^+=290$, $RT=0.219$ min Preparation of Intermediate 32

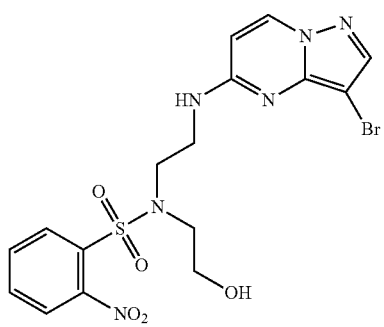 [SMILES: O=[N+]([O-])c1ccccc1S(=O)(=O)N(CCO)CCNc1ccn2ncc(Br)c2n1]

A mixture of 3-bromo-5-chloro-pyrazolo[1,5-a]pyrimidine (10.0 g, 43.02 mmol), intermediate 31 (18.22 g, 55.92 mmol) and N,N-diisopropylethylamine (22.48 ml, 129.05 mmol) in acetonitrile (129 ml) was refluxed overnight. The reaction mixture was cooled and the solvent was removed under reduced pressure. The residue was dissolved in ethyl acetate and washed with water and brine. The organic layer was dried, filtered and the solvent was removed under reduced pressure. The residue was purified by flash column chromatography over silica gel using dichloromethane and methanol as eluents. The product fractions were collected and the solvent was evaporated.
Yield: 16.74 g of intermediate 32 (80%)
LCMS method 1: $MH^+=487$, $RT=0.942$ min Preparation of Intermediate 33

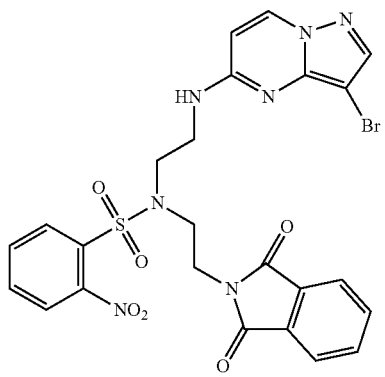 [SMILES: O=C1c2ccccc2C(=O)N1CCN(CCNc1ccn2ncc(Br)c2n1)S(=O)(=O)c1ccccc1[N+](=O)[O-]]

A solution of intermediate 32 (12.66 g, 26.09 mmol) in dry tetrahydrofuran (78 ml) was degassed by bubbling nitrogen gas through the solution. Isoindoline-1,3-dione (5.76 g, 39.13 mmol) and triphenylphosphine (10.26 g, 39.13 mmol) were added and the mixture was cooled to 5° C. Diisopropyl azodicarboxylate (7.76 g, 39.13 mmol) was added and the mixture was stirred at room temperature for 2 hours. The solvent was removed under reduced pressure and water was added. The water layer was extracted with ethyl acetate. The organic layer was dried, filtered and the solvent was removed under reduced pressure. The product was used without further purification in the next step.
LCMS method 1: $MH^+=616$, $RT=1.225$ min Preparation of Intermediate 34

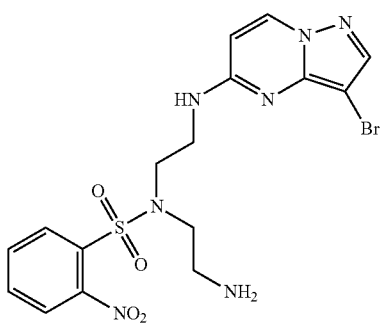

A mixture of intermediate 33 (12.26 g, 19.96 mmol) and hydrazine (1.86 ml, 29.94 mmol) in ethanol (60 ml) was stirred under reflux overnight. The reaction mixture was cooled, filtered and the solvent was removed under reduced pressure. The residue was dissolved in ethyl acetate and washed with 1N sodium hydroxide and water. The organic layer was dried, filtered and the solvent was removed under reduced pressure. The product was used without further purification in the next step.
LCMS method 1: $MH^+=486$, $RT=0.503$ min Preparation of Intermediate 35

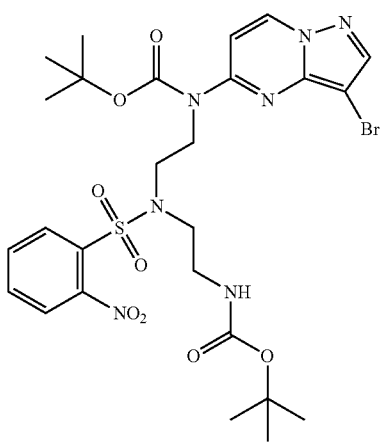 [SMILES: CC(C)(C)OC(=O)NCCN(CCN(C(=O)OC(C)(C)C)c1ccn2ncc(Br)c2n1)S(=O)(=O)c1ccccc1[N+](=O)[O-]]

To a solution of intermediate 34 (19.97 mmol) in tetrahydrofuran (60 ml) were added tert-butoxycarbonyl anhydride (10.89 g, 49.91 mmol) and 4-(dimethylamino)pyridine (244 mg, 2.00 mmol). The mixture was stirred at room temperature overnight. The solvent was removed under reduced pressure. The residue was purified by flash column chromatography over silica gel using heptane and ethyl acetate as eluents. The product fractions were collected and the solvent was evaporated.

LCMS method 1: MH⁺=586 (MW-Boc), RT=1.769 min

Preparation of Intermediate 36

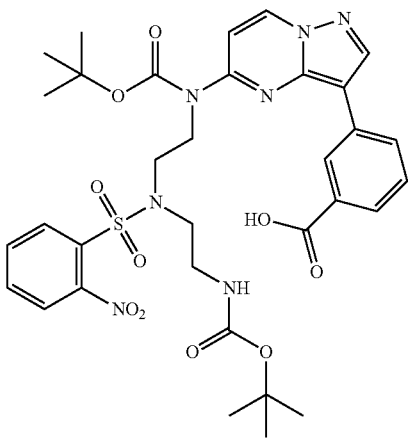 [SMILES: CC(C)(C)OC(=O)NCCN(CCN(C(=O)OC(C)(C)C)c1ccn2ncc(-c3cccc(C(=O)O)c3)c2n1)S(=O)(=O)c1ccccc1[N+](=O)[O-]]

A mixture of 1,4-dioxane and water (3:1, 85 ml) was degassed by bubbling nitrogen gas through the mixture. Intermediate 35 (5.78 g, 8.44 mmol), 3-boronobenzoic acid (2.10 g, 12.66 mmol), tetrakis(triphenylphosphine)palladium(0) (97 mg, 0.084 mmol), 2-dicyclohexylphosphino-2',4',6'-triisopropylbiphenyl (Xphos) (243 mg, 0.51 mmol) and potassium phosphate tribasic (8.96 g, 5 eq.) were added and the mixture was stirred under nitrogen gas at 80° C. for 5 hours. The reaction mixture was cooled, diluted with ethyl acetate and the organic layer was washed with water. The organic layer was dried, filtered and the solvent was removed under reduced pressure. The residue was purified by flash column chromatography over silica gel using heptane and ethyl acetate and then dichloromethane and methanol as eluents. The product fractions were collected and the solvent was evaporated.

Yield: 4.75 g of intermediate 36 (78%)

LCMS method 1: MH⁺=626 (MW-Boc), RT=1.586 min

Preparation of Intermediate 37

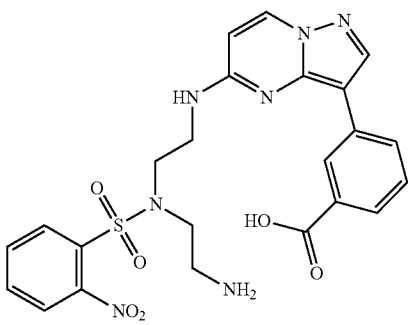 [SMILES: NCCN(CCNc1ccn2ncc(-c3cccc(C(=O)O)c3)c2n1)S(=O)(=O)c1ccccc1[N+](=O)[O-]]

Intermediate 36 (4.75 g, 6.54 mmol) was dissolved in 4N hydrochloric acid solution in dioxane/water (1:1, 20 ml). The mixture was stirred at room temperature for 2 hours. The solvent was removed under reduced pressure and toluene was added. The mixture was stirred and the solvent was removed under reduced pressure. The product was used without further purification in the next step.

LCMS method 1: MH⁺=526, RT=0.606 min

Preparation of Intermediate 38

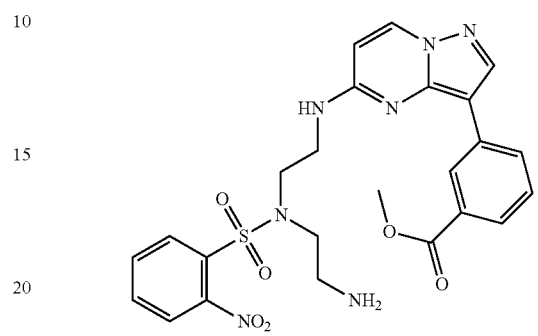

A mixture of intermediate 37 (2.00 g, 3.56 mmol) and 4N acetylchloride in methanol (11 ml) was heated at 60° C. for 54 hours. The solvent was removed under reduced pressure and the product was without any further purification used in the next step.

Preparation of Intermediate 39

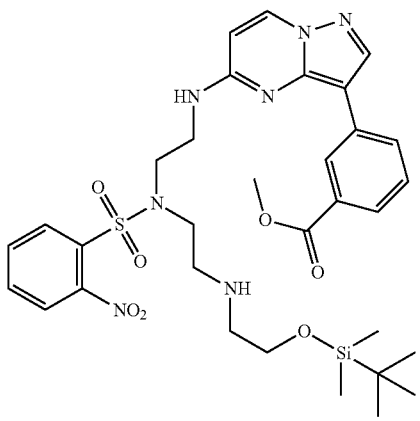 [SMILES: COC(=O)c1cccc(-c2cnn3ccc(NCCN(CCNCCO[Si](C)(C)C(C)(C)C)S(=O)(=O)c4ccccc4[N+](=O)[O-])nc23)c1]

2-(tert-Butyl(dimethyl)silyl)oxyacetaldehyde (0.854 ml, 4.40 mmol) was added to a suspension of intermediate 38 (1.95 g, 3.385 mmol) and diisopropyl ethylamine (1.768 ml, 10.15 mmol) in methanol (10 ml). The mixture was stirred at room temperature for 1 hour and sodium borohydride (0.192 g, 5.08 mmol) was added in small portions. The mixture was stirred at room temperature for 1 hour. The solvent was removed under reduced pressure, water was added and the product was extracted with ethyl acetate. The organic layer was dried, filtered and the solvent was removed under reduced pressure. The product was purified by flash chromatography over silica gel using mixtures of dichloromethane and methanol as eluents. The product fractions were collected and the solvent was evaporated.

Yield: 748 mg of intermediate 39 (32%)

LCMS method 1: MH⁺=698, RT=1.221 min

Preparation of Intermediate 40

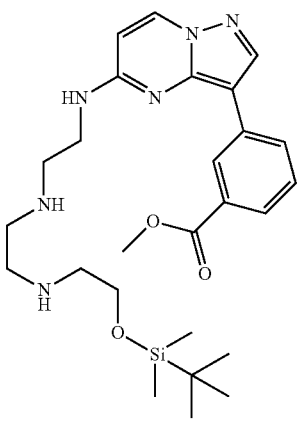 [SMILES: COC(=O)c1cccc(-c2cnn3ccc(NCCNCCNCCO[Si](C)(C)C(C)(C)C)nc23)c1]

Intermediate 39 (0.748 g, 1.072 mmol) and cesium carbonate (0.755 g, 2.14 mmol) were suspended in N,N-dimethylformamide (3 ml). Thiophenol (132 µl, 2.14 mmol) was added and the mixture was stirred at room temperature for 3 hours. The solvent was removed under reduced pressure. The residue was purified by flash column chromatography over silica gel using dichloromethane and methanol as eluents. The product fractions were collected and the solvent was evaporated.

Yield: 0.496 g of intermediate 40 (90%)

LCMS method 1: $MH^+$=513, RT=0.831 min

Preparation of Intermediate 41

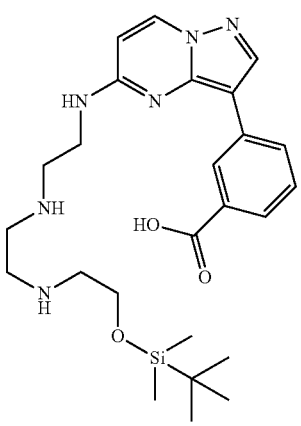 [SMILES: CC(C)(C)[Si](C)(C)OCCNCCNCCNc1ccn2ncc(-c3cccc(C(=O)O)c3)c2n1]

Intermediate 40 (0.448 g, 0.874 mmol) and lithium hydroxide monohydrate (37 mg, 0.87 mmol) were suspended in tetrahydrofuran/methanol (1:1, 3.5 ml). The mixture was stirred overnight at room temperature. 1N HCl solution was added until pH 7 and the solvent was evaporated twice with toluene. The TBDMS group was partially removed. The product was used without further purification in the next step.

LCMS method 1: $MH^+$=499, RT=0.714 min

Preparation of Example 7

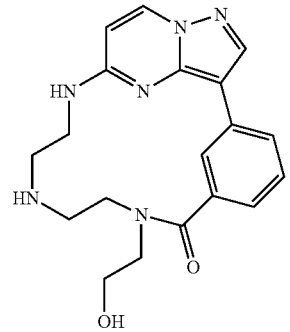 [SMILES: O=C1c2cccc(c2)-c2cnn3ccc(nc23)NCCNCCN1CCO]

A solution of intermediate 41 (0.434 g, 0.870 mmol) in N,N-dimethylformamide (26 ml) was added dropwise over a period of 2 hours to a solution of N,N-diisopropylethylamine (0.90 ml, 5.22 mmol) and O-(benzotriazol-1-yl)-N,N,N',N'-tetramethyluronium hexafluorophosphate (HBTU) (0.99 g, 2.61 mmol) in N,N-dimethylformamide (61 ml). The solvent was removed under reduced pressure and the residue was purified by reversed phase column chromatography (HPLC method A). The product fractions were collected and the solvent was evaporated.

Yield: 65 mg of example 7 (20%)

LCMS method 2: $MH^+$=367, RT=1.223 min

Example 8

Example 8 is prepared following general scheme 1.

Example 8 is prepared according to the synthetic methods used for the preparation of Example 7.

Preparation of Intermediate 42

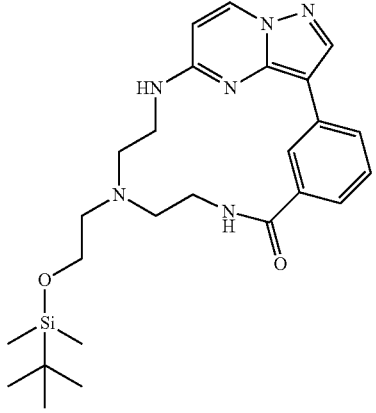 [SMILES: CC(C)(C)[Si](C)(C)OCCN1CCNC(=O)c2cccc(c2)-c2cnn3ccc(nc23)NCC1]

8,11,14,18,19,22-Hexaazatetracyclo[13.5.2.1^{2,6}.0^{18,21}]tricosa-1(21),2,4,6(23),15(22),16,19-heptaen-7-one (330 mg, 1.02 mmol), triethylamine (0.357 ml, 2.05 mmol) and 2-(tert-butyl(dimethyl)silyl)oxyacetaldehyde (0.258 ml, 1.23 mmol) were dissolved in a mixture of 1,2-dichloroethane and methanol (10:1, 20 ml) and the mixture was stirred at room temperature for 3 hours. Sodium triacetoxyborohydride (2.048 mmol) was added in small portions and the mixture was stirred at room temperature for 2 hours. The reaction mixture was poured into ethyl acetate and the organic layer was washed with a saturated aqueous sodium bicarbonate solution and brine. The organic layer was dried, filtered and the solvent was removed under reduced pressure. The product was used without further purification in the next step.

LCMS method 1: MH$^+$=481, RT=0.954 min

Preparation of Example 8

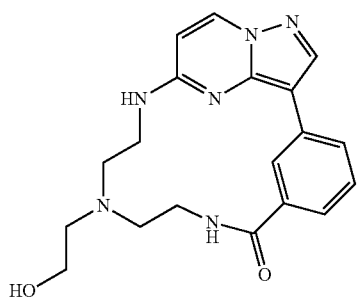 [SMILES: O=C1NCCN(CCO)CCNc2ccn3ncc(c3n2)-c2cccc1c2]

Intermediate 42 (0.39 g, 0.81 mmol) in a mixture of acetic acid/water/tetrahydrofuran (3:1:1, 2.43 ml) was stirred at 60° C. for 4 hours. The solvent was removed under reduced pressure and dichloromethane was added. A precipitate was formed which was filtered, washed with methanol and dried under vacuum. The solvent of the mother liquor was removed under reduced pressure. The residue was purified by flash column chromatography over silica gel using dichloromethane and methanol as eluents. The product fractions were collected and the solvent was evaporated. The residue was added to the solid obtained after the addition of dichloromethane.

Yield: 242 mg of example 8 (81%)
LCMS method 2: MH$^+$=367, RT=1.256 min

Example 9

Example 9 is prepared following general scheme 1.
Example 9 is prepared according to the synthetic methods used for the preparation of Example 8.

Preparation of Example 9

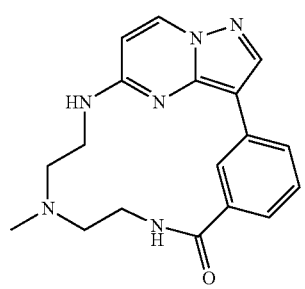 [SMILES: CN1CCNC(=O)c2cccc(c2)-c2cnn3ccc(nc23)NCC1]

Palladium/C (10% wet, 0.24 mmol) was added to a solution of 8,11,14,18,19,22-Hexaazatetracyclo[13.5.2.1ˆ{2,6}.0ˆ{18,21}]tricosa-1(21),2,4,6(23),15(22),16,19-heptaen-7-one (77 mg, 0.239 mmol) in N,N-dimethylformamide (0.72 ml). The mixture was stirred under atmospheric pressure of hydrogen gas at room temperature for 48 hours. Methanol (1 ml) and acetic acid (1 ml) were added and the mixture was stirred under atmospheric pressure of hydrogen gas at room temperature for 24 hours. Methanol (1 ml) and acetic acid (1 ml) and palladium/C (10% wet, 0.24 mmol) were added and the mixture was again stirred under atmospheric pressure of hydrogen gas at room temperature for 48 hours. The reaction mixture was filtered over celite and washed with dichloromethane and methanol. The solvent was removed under reduced pressure and the prodcut was purified by flash chromatography over silica gel using dichloromethane and methanol as eluents. The product fractions were collected and the solvent was evaporated.

Yield: 15 mg of example 9 (19%)
LCMS method 2: MH$^+$=337, RT=1.290 min

Example 10

Example 10 is prepared following general scheme 1.

Preparation of Intermediate 43

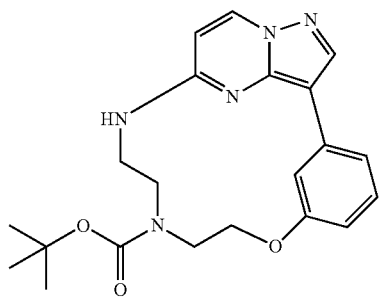 [SMILES: CC(C)(C)OC(=O)N1CCNc2ccn3ncc(c3n2)-c2cccc(c2)OCC1]

A mixture of 7-oxa-10,13,17,18,21-pentaazatetracyclo[12.5.2.1ˆ{2,6}.0ˆ{17,20}]docosa-1(20),2,4,6(22),14(21),15,18-heptaene (0.42 g, 1.27 mmol), tert-butoxycarbonyl anhydride (0.33 g, 1.52 mmol) and triethylamine (0.528 ml, 3.81 mmol) in tetrahydrofurane (4 ml) was stirred at room temperature overnight. The solvent was removed under reduced pressure. The residue was recrystallized from acetonitrile and the product was used without further purification in the next step.

LCMS method 1: MH$^+$=396, RT=1.472 min

Preparation of Intermediate 44

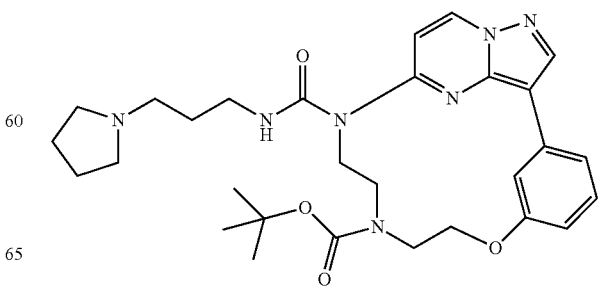

Triphosgene (0.53 g, 1.78 mmol) was added to a solution of intermediate 43 (0.35 mg, 0.89 mmol) in 1,2-dichloroethane (1.2 ml) at 0° C. under nitrogen atmosphere. The reaction mixture was stirred at room temperature for 30 minutes. 3-Pyrrolidin-1-ylpropan-1-amine (0.169 ml, 1.34 mmol) was added and the mixture was stirred at 50° C. for 30 minutes. The reaction mixture was cooled and the solvent was removed under reduced pressure. The residue was purified by flash column chromatography over silica gel using heptane and ethyl acetate as eluents. The product fractions were collected and the solvent was evaporated.

Yield: 0.400 g of intermediate 44 (82%)

LCMS method 2: MH$^+$=550, RT=2.550 min

Preparation of Example 10

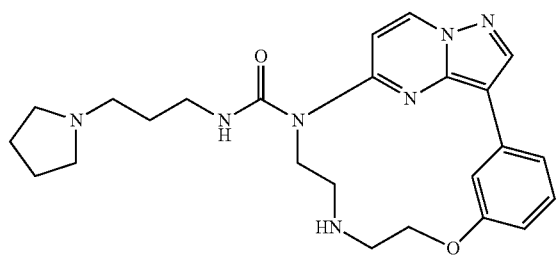 [SMILES: O=C(NCCCN1CCCC1)N1CCNCCOc2cccc(c2)-c2cnn3ccc1nc23]

Intermediate 44 (0.40 g, 0.73 mmol) was dissolved in 4N hydrochloric acid solution in methanol (2 ml). The mixture was stirred at room temperature for 3 hours. The formed solid was filtered and dried under high vacuum.

Yield: 102 mg of example 10 (31%)

LCMS method 2: MH$^+$=451, RT=1.180 min

Example 11

Example 11 is prepared following general scheme 1.

Preparation of Intermediate 45

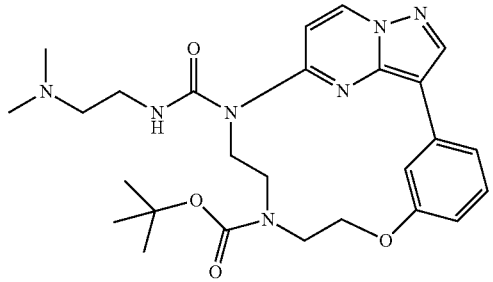 [SMILES: CN(C)CCNC(=O)N1CCN(C(=O)OC(C)(C)C)CCOc2cccc(c2)-c2cnn3ccc1nc23]

Triphosgene (0.33 g, 1.12 mmol) was added to a solution of intermediate 43 (0.22 mg, 0.56 mmol) in 1,2-dichloroethane (2.6 ml) at 0° C. under nitrogen atmosphere. The reaction mixture was stirred at room temperature for 30 minutes. N',N'-Dimethylethane-1,2-diamine (0.093 ml, 0.84 mmol) was added and the mixture was stirred at 50° C. for 30 minutes. The reaction mixture was cooled and the solvent was removed under reduced pressure. The residue was purified by flash column chromatography over silica gel using heptane and ethyl acetate as eluents. The product fractions were collected and the solvent was evaporated.

Yield: 0.260 g of intermediate 45 (91%)

Preparation of Example 11

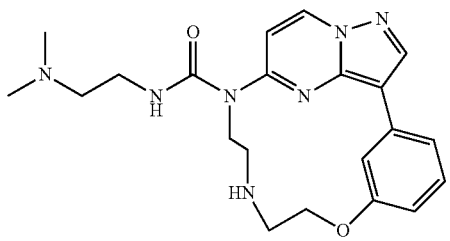 [SMILES: CN(C)CCNC(=O)N1CCNCCOc2cccc(c2)-c2cnn3ccc1nc23]

Intermediate 44 (0.26 g, 0.51 mmol) was dissolved in 4N hydrochloric acid solution in methanol (1.5 ml). The mixture was stirred at room temperature for 3 hours. The formed solid was filtered and dried under high vacuum.

Yield: 189 mg of example 11 (77%)

LCMS method 2: MH$^+$=410, RT=1.131 min

Example 12

Example 12 is prepared following general scheme 1.

Preparation of Example 12

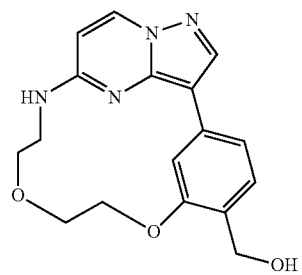 [SMILES: OCc1ccc2cc1OCCOCCNc1ccn3ncc-2c3n1]

Isobutyl carbonochloridate (0.20 g, 1.54 mmol) was added to a solution of Example 1 (0.435 g, 1.28 mmol) and triethylamine (0.266 ml, 1.92 mmol) in tetrahydrofuran (4 ml). The mixture was stirred at room temperature for 30 minutes. Sodium borohydride (0.145 g, 3.84 mmol) was added at the mixture was refluxed for 30 minutes. Methanol (2 ml/mmol) was added and the mixture was refluxed for 1 hour. The reaction mixture was cooled and a saturated aqueous ammonium chloride solution was added. The product was extracted with ethyl acetate. The organic layer was dried, filtered and the solvent was removed under reduced pressure. The resulting solid was triturated with methanol to yield the desired product.

Yield: 62 mg of example 12 (15%)

LCMS method 2: MH$^+$=327, RT=2.223 min

Example 13

Example 13 is prepared following general scheme 2.

Preparation of Intermediate 46

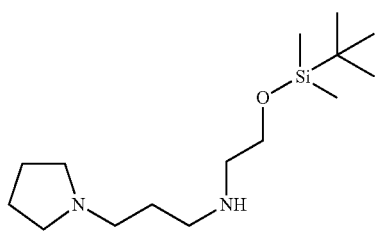 [SMILES: CC(C)(C)[Si](C)(C)OCCNCCCN1CCCC1]

3-pyrrolidin-1-ylpropan-1-amine (3.00 g, 23.40 mmol) and 2-(tert-butyl(dimethyl)silyl)oxyacetaldehyde (4.88 ml, 25.74 mmol) were dissolved in methanol (70 ml) and the mixture was stirred at room temperature for 30 minutes. Sodium borohydride (0.974 g, 25.74 mmol) was added in small portions and the reaction mixture was stirred at room temperature for 1 hour. The solvent was removed under reduced pressure and the product was without any further purification used in the next step.

LCMS method 2: MH$^+$=287, RT=1.375 min

Preparation of Intermediate 47

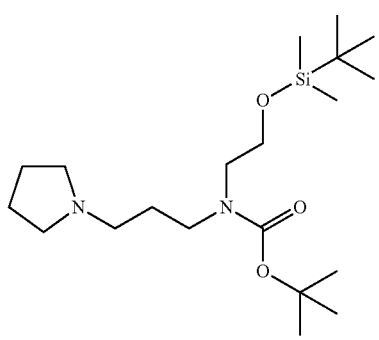 [SMILES: CC(C)(C)OC(=O)N(CCCN1CCCC1)CCO[Si](C)(C)C(C)(C)C]

A mixture of intermediate 46 (23.4 mmol), tert-butoxycarbonyl anhydride (5.62 g, 25.74 mmol) and triethylamine (3.892 ml, 28.08 mmol) in tetrahydrofurane (70 ml) was stirred at 50° C. for 2 hours. The solvent was removed under reduced pressure. The residue was purified by flash column chromatography over silica gel using dichloromethane and methanol as eluents. The product fractions were collected and the solvent was evaporated.

Yield: 2.810 g of intermediate 47 (31%)

LCMS method 1: MH$^+$=387, RT=1.063 min

Preparation of Intermediate 48

Intermediate 47 (2.810 g, 7.27 mmol) in a mixture of acetic acid/tetrahydrofuran/water (3:1:1, 22 ml) was stirred at 60° C. overnight. The solvent was removed under reduced pressure and the product was without any further purification used in the next step.

LCMS method 2: MH$^+$=273, RT=1.274 min

Preparation of Intermediate 49

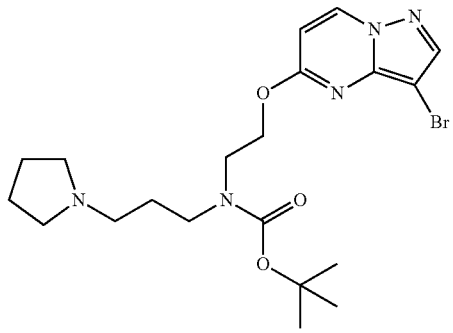 [SMILES: CC(C)(C)OC(=O)N(CCCN1CCCC1)CCOc1ccn2ncc(Br)c2n1]

Sodium hydride (60% in mineral oil, 318 mg, 7.95 mg) was dissolved in dry tetrahydrofuran under nitrogen atmosphere. Intermediate 48 (0.96 g, 3.50 mmol) was added and the mixture was stirred at room temperature for 15 minutes. 3-Bromo-5-chloro-pyrazolo[1,5-a]pyrimidine (0.74 g, 3.18 mmol) was added and the mixture was stirred at room temperature for 30 minutes. The solvent was removed under reduced pressure. The residue was purified by flash column chromatography over silica gel using dichloromethane and methanol as eluents. The product fractions were collected and the solvent was evaporated.

Yield: 0.860 g of intermediate 49 (58%)

LCMS method 1: MH$^+$=468, RT=0.834 min

Preparation of Intermediate 50

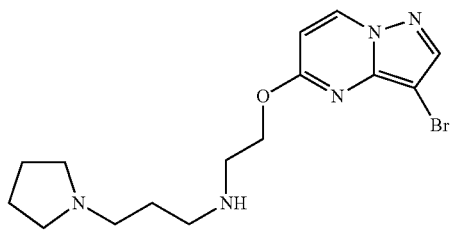 [SMILES: Brc1cnn2ccc(OCCNCCCN3CCCC3)nc12]

Intermediate 49 (0.86 g, 1.84 mmol) was dissolved in 4N hydrochloric acid solution in methanol (5.5 ml). The mixture was stirred at room temperature overnight. The solvent was removed under reduced pressure and the product was without any further purification used in the next step.

LCMS method 1: MH$^+$=370, RT=0.178 min

Preparation of Intermediate 51

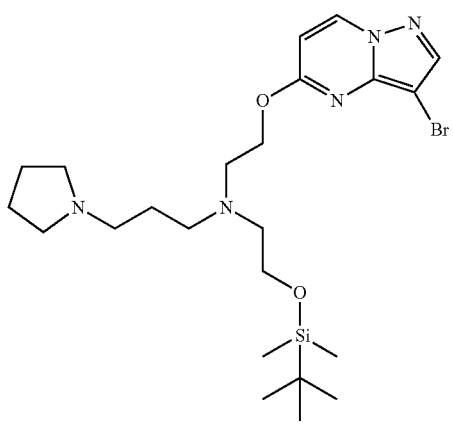 [SMILES: CC(C)(C)[Si](C)(C)OCCN(CCCN1CCCC1)CCOc1ccn2ncc(Br)c2n1]

Intermediate 50 (1.84 mmol), triethylamine (0.559 ml, 5.52 mmol) and 2-(tert-butyl(dimethyl)silyl)oxyacetaldehyde (0.38 ml, 2.02 mmol) were dissolved in dichlormoethane (5.5 ml). Sodium triacetoxyborohydride (0.780 g, 3.68 mmol) was added in small portions and the mixture was stirred at room temperature for 1 hour. The solvent was removed under reduced pressure. The residue was purified by flash column chromatography over silica gel using dichloromethane and methanol as eluents. The product fractions were collected and the solvent was evaporated.

LCMS method 1: MH$^+$=526, RT=0.693 min

Preparation of Intermediate 52

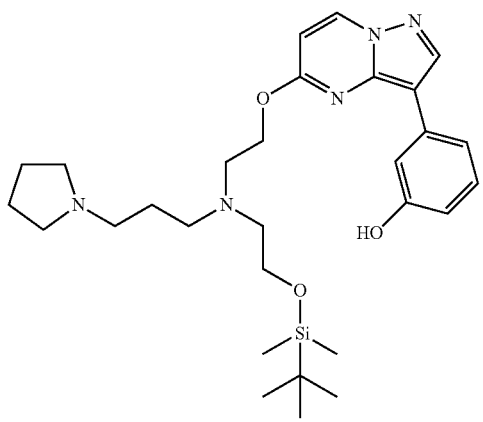 [SMILES: CC(C)(C)[Si](C)(C)OCCN(CCCN1CCCC1)CCOc1ccn2ncc(-c3cccc(O)c3)c2n1]

A mixture of 1,4-dioxane and water (3:1, 8.5 ml) was degassed by bubbling nitrogen gas through the mixture. Intermediate 51 (0.449 g, 0.85 mmol), (3-hydroxyphenyl)boronic acid (0.15 g, 1.11 mmol), tetrakis(triphenylphosphine)palladium(0) (12 mg, 0.01 mmol), 2-dicyclohexylphosphino-2',4',6'-triisopropylbiphenyl (Xphos) (14 mg, 0.03 mmol) and potassium phosphate tribasic (0.9 g, 5 eq.) were added and the mixture was stirred under nitrogen gas at 80° C. for 2 hours. The reaction mixture was cooled, diluted with ethyl acetate and the organic layer was washed with water and brine. The organic layer was dried, filtered and the solvent was removed under reduced pressure. The residue was purified by flash column chromatography over silica gel using heptane and ethyl acetate as eluents. The product fractions were collected and the solvent was evaporated.

Yield: 0.23 g of intermediate 52 (50%)

LCMS method 2: MH$^+$=540, RT=1.897 min

Preparation of Intermediate 53

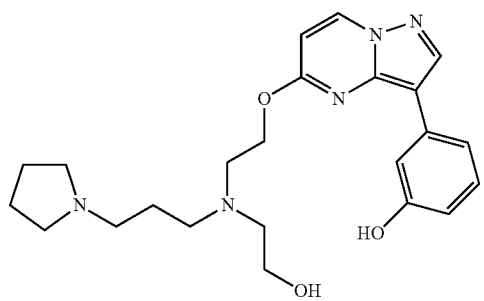 [SMILES: OCCN(CCCN1CCCC1)CCOc1ccn2ncc(-c3cccc(O)c3)c2n1]

Intermediate 52 (0.23 g, 0.43 mmol) in a mixture of acetic acid/tetrahydrofuran/water (3:1:1, 1.3 ml) was stirred at room temperature for 1 hour. Toluene was added and the solvent was removed under reduced pressure and the product was without any further purification used in the next step.

Yield: 0.14 g of intermediate 53 (77%)

LCMS method 2: MH$^+$=426, RT=1.136 min

Preparation of Intermediate 54

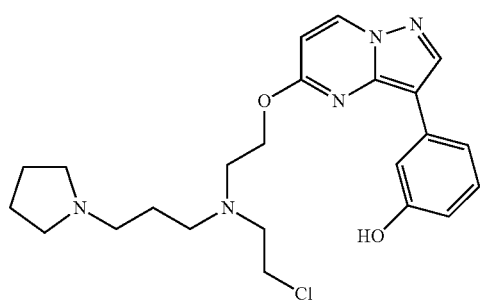 [SMILES: Oc1cccc(-c2cnn3ccc(OCCN(CCCl)CCCN4CCCC4)nc23)c1]

Thionyl chloride (0.07 ml, 0.99 mmol) was added to a solution of intermediate 53 (0.14 g, 0.33 mmol) and pyridine (80 µl, 0.99 mmol) in dichloromethane (1 ml). The mixture was refluxed for 2 hours. The solvent was removed under reduced pressure and the product was without any further purification used in the next step.

LCMS method 1: MH$^+$=444, RT=0.500 min

Preparation of Example 13

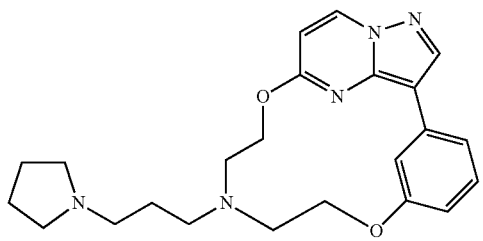 [SMILES: c1cc2cc(c1)-c1cnn3ccc(nc13)OCCN(CCCN1CCCC1)CCO2]

A solution of intermediate 53 (0.33 mmol) in 4N HCl in 1,4-dioxane (0.33 mmol) was added drop wise to a solution of cesium carbonate (0.54 g, 1.65 mmol) in N,N-dimethylformamide (1 ml) at 90° C. The mixture was stirred at 90° C. for 2 hours. The solvent was removed under reduced pressure. The residue was purified by flash column chromatography over silica gel using heptane and ethyl acetate as eluents. The product fractions were collected and the solvent was evaporated.

Yield: 51 g of example 13 (35%)

LCMS method 2: MH$^+$=408, RT=1.926 min

Example 14

Example 13 is prepared following general scheme 1.

Preparation of Intermediate 55

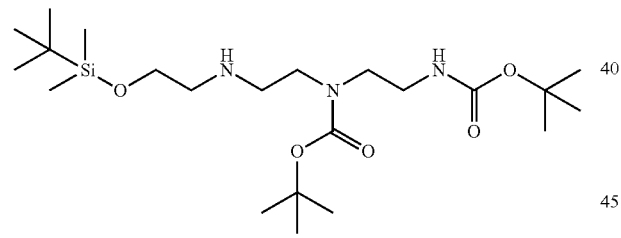

2-(tert-Butyl(dimethyl)silyl)oxyacetaldehyde (1.527 ml, 8.24 mmol) was added to a solution of tert-butyl N-[2-(2-aminoethyl(tert-butoxycarbonyl)amino)ethyl]carbamate (2.50 g, 8.24 mmol) in methanol (25 ml). The mixture was stirred at room temperature for 30 minutes and sodium borohydride (0.312 g, 8.24 mmol) was added in small portions. The mixture was stirred at room temperature for 1 hour. 0.2 Equivalents of 2-(tert-Butyl(dimethyl)silyl)oxyacetaldehyde was added and the mixture was stirred at room temperature for 30 minutes. 0.22 Equivalents of sodium borohydride and the mixture was stirred at room temperature for 30 more minutes. A few drops of water were added and the solvent was removed under reduced pressure. The residue was purified by flash chromatography over silica gel using mixtures of dichloromethane and methanol as eluents. The product fractions were collected and the solvent was evaporated.

Yield: 3.06 mg of intermediate 55 (80%)

LCMS method 2: MH$^+$=462, RT=1.899 min

Preparation of Intermediate 56

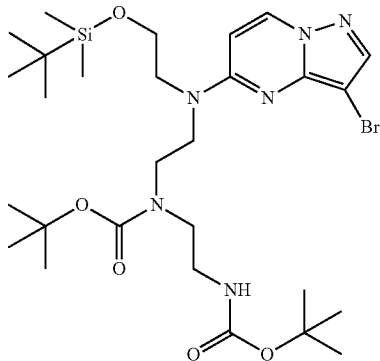 [SMILES: CC(C)(C)OC(=O)NCCN(CCN(CCO[Si](C)(C)C(C)(C)C)c1ccn2ncc(Br)c2n1)C(=O)OC(C)(C)C]

A mixture of 3-bromo-5-chloro-pyrazolo[1,5-a]pyrimidine (1.5 g, 9.75 mmol), intermediate 55 (3.0 g, 6.497 mmol) and N,N-diisopropylethylamine (2.263 ml, 12.99 mmol) in acetonitrile (19.5 ml) was stirred at 85° C. for 22 hours. 0.3 Equivalents of 3-bromo-5-chloro-pyrazolo[1,5-a]pyrimidine was added and the mixture was stirred at 90° C. for 22 hours. The reaction mixture was cooled and the solvent was removed under reduced pressure. The residue was purified by flash column chromatography over silica gel using heptane and ethyl acetate as eluents. The product fractions were collected and the solvent was evaporated.

Yield: 3.15 g of intermediate 56 (74%)

LCMS method 1: MH$^+$=659, RT=2.398 min

Preparation of Intermediate 57

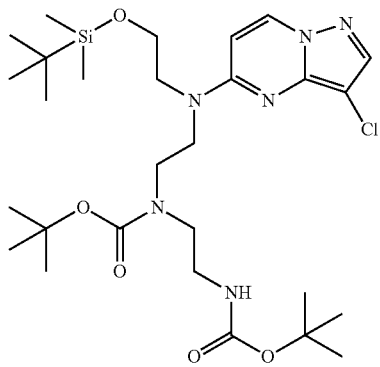 [SMILES: CC(C)(C)OC(=O)NCCN(CCN(CCO[Si](C)(C)C(C)(C)C)c1ccn2ncc(Cl)c2n1)C(=O)OC(C)(C)C]

During the Suzuki coupling performed below, the compound was obtained in which the bromo was reduced. Subsequently a chlorogroup was introduced.

A mixture of N,N-dimethylformamide and water (3:1, 11.6 ml) was degassed by bubbling nitrogen gas through the mixture. Intermediate 56 (2.550 g, 3.877 mmol), 3-boronobenzoic acid (0.966 g, 5.82 mmol), palladium(II)acetate (26 mg, 0.116 mmol), 2-dicyclohexylphosphino-2',4',6'-triisopropylbiphenyl (Xphos) (167 mg, 0.35 mmol) and sodium carbonate (1.233 g, 3 eq.) were added and the mixture was stirred under nitrogen gas at 80° C. overnight. The reaction mixture was cooled, water was added and the product was extracted with ethyl acetate. The organic layer was dried, filtered and the solvent was removed under reduced pressure. The product obtained was the product in which the bromo of the starting material was reduced.

A solution of the product from the previous step (1.87 g, 3.231 mmol) was together with 1-chloropyrrolidine-2,5-dione (0.431 g, 3.23 mmol) in acetonitrile (10 ml) was stirred at room temperature for 4 hours. The solvent was removed under reduced pressure. The residue was purified by flash column chromatography over silica gel using heptane and ethyl acetate as eluents. The product fractions were collected and the solvent was evaporated.

Yield: 0.45 g of intermediate 57 (23%)
LCMS method 1: MH$^+$=613, RT=2.382 min

Preparation of Intermediate 58

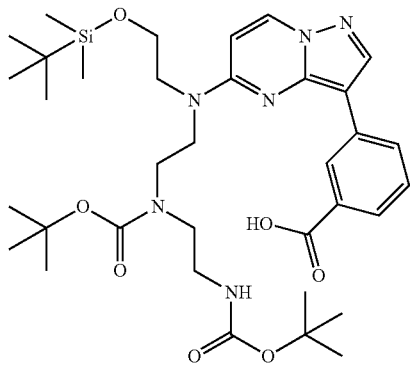 [SMILES: CC(C)(C)OC(=O)NCCN(CCN(CCO[Si](C)(C)C(C)(C)C)c1ccn2ncc(-c3cccc(C(=O)O)c3)c2n1)C(=O)OC(C)(C)C]

A mixture of N,N-dimethylformamide and water (3:1, 3.5 ml) was degassed by bubbling nitrogen gas through the mixture. Intermediate 57 (0.350 g, 0.571 mmol), 3-boronobenzoic acid (0.189 g, 1.14 mmol), palladium(II)acetate (7 mg, 0.029 mmol), 2-dicyclohexylphosphino-2',4',6'-triisopropylbiphenyl (Xphos) (38 mg, 0.08 mmol) and sodium carbonate (3 eq.) were added and the mixture was stirred under nitrogen gas at 80° C. overnight. 0.5 Equivalents of -boronobenzoic acid, palladium(II)acetate, 2-dicyclohexylphosphino-2',4',6'-triisopropylbiphenyl (Xphos) were added and the mixture was stirred at 80° C. for 6 hours. The reaction mixture was cooled, water was added and the product was extracted with ethyl acetate. The organic layer was dried, filtered and the solvent was removed under reduced pressure. The residue was purified by flash column chromatography over silica gel using dichloromethane and methanol as eluents. The product fractions were collected and the solvent was evaporated.

Yield: 0.112 g of intermediate 58 (30%)
LCMS method 1: MH$^+$=699, RT=2.095 min

Preparation of Intermediate 59

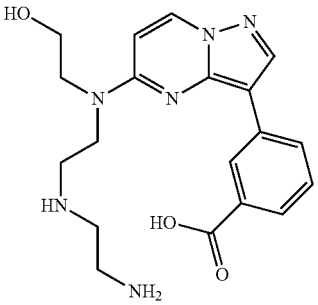 [SMILES: NCCNCCN(CCO)c1ccn2ncc(-c3cccc(C(=O)O)c3)c2n1]

Intermediate 58 (0.118 g, 0.169 mmol) was dissolved in 4N hydrochloric acid solution in 1,4-dioxane (0.5 ml). The mixture was stirred at room temperature for 2 hours. The solvent was removed under reduced pressure and the product was without any further purification used in the next step.

LCMS method 1: MH$^+$=385, RT=0.288 min

Preparation of Example 14

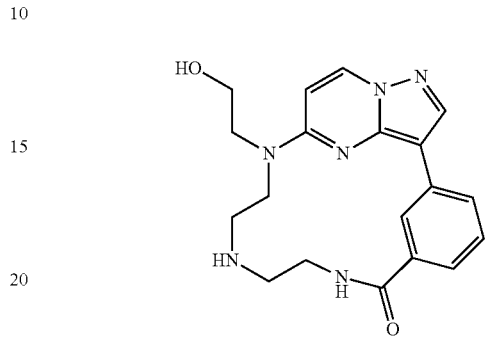

A solution of intermediate 59 (97 mg, 0.23 mmol) in N,N-dimethylformamide (7 ml) was added dropwise to a solution of N,N-diisopropylethylamine (0.40 ml, 2.30 mmol) and O-(benzotriazol-1-yl)-N,N,N',N'-tetramethyluronium hexafluorophosphate (HBTU) (0.262 g, 0.69 mmol) in N,N-dimethylformamide (16 ml). The reaction mixture was stirred at room temperature for 1 hour. The mixture was quenched with an aqueous solution of ammonia (25%, 10 ml) and the mixture was stirred at room temperature for 30 minutes. The solvent was removed under reduced pressure and the residue was purified by reversed phase column chromatography (HPLC method A). The product fractions were collected and the solvent was evaporated.

Yield: 22 mg of example 14 (26%)
LCMS method 2: MH$^+$=367, RT=1.201 min

Example 15

Example 15 is prepared following general scheme 1.

Preparation of Example 15

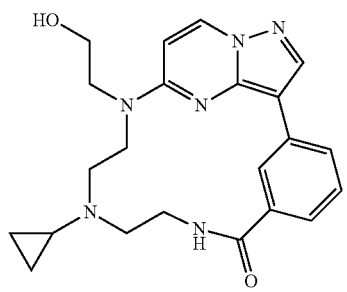 [SMILES: O=C1NCCN(C2CC2)CCN(CCO)c2ccn3ncc(c3n2)-c2cccc1c2]

Molecular sieves were added to a solution of Example 14 (8 mg, 0.02 mmol) in dry methanol (0.25 ml). Acetic acid (23 µl, 0.40 mmol), (1-ethoxycyclopropoxy)-trimethyl-silane (50 µl, 0.24 mmol) and sodium cyanoborohydride (11 mg, 0.18 mmol) were added and the reaction mixture was stirred at 70° C. for 18 hours. The solvent was removed under reduced pressure and the residue was purified by reversed phase column chromatography (HPLC method A). The product fractions were collected and the solvent was evaporated.
Yield: 2 mg of example 15 (8%)
LCMS method 2: MH$^+$=407, RT=1.105 min Example 16

Preparation of Eexample 16,

Example 16 is prepared following general scheme 2.

Preparation of Intermediate 60

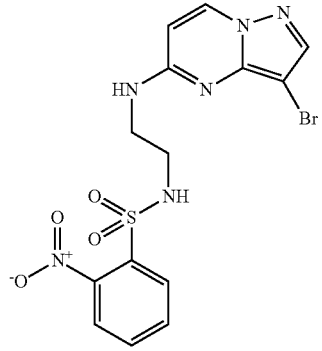

A mixture of 3-bromo-5-chloro-pyrazolo[1,5-a]pyrimidine (10.2 g, 43.88 mmol), N-(2-aminoethyl)-2-nitro-benzenesulfonamide hydrochloride (12.98 g, 46.07 mmol) and N,N-diisopropylethylamine (22.387 ml, 131.64 mmol) in acetonitrile (131.64 ml) was refluxed for 10 hours. The reaction mixture was cooled and concentrated under reduced pressure. The precipitate was filtered, washed with water, acetonitrile and diethyl ether. The compound was dried under reduced pressure and used in the next step without further purification.
Yield: 16.8 g of intermediate 60 (87%)
LCMS method 1: MH$^+$=442, RT=0.729 min Preparation of Intermediate 61

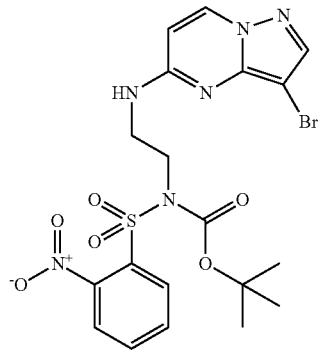

A mixture of intermediate 60 (18.10 g, 41.02 mmol), tert-butoxycarbonyl anhydride (8.95 g, 41.02 mmol) and 4-(dimethylamino)pyridine (250 mg, 2.05 mmol) in tetrahydrofuran (123.06 ml) was stirred at 55° C. for 5 hours. More tert-butoxycarbonyl anhydride (895 mg, 4.102 mmol) was added and the reaction mixture was stirred at 55° C. for 5 hours. The reaction mixture was cooled and the solvent was removed under reduced pressure. The residue was purified by flash column chromatography over silica gel using heptane and ethyl acetate as eluents (gradient elution from 10% to 40% ethyl acetate). The product fractions were collected and the solvent was removed under reduced pressure.
Yield: 18.3 g of intermediate 61 (82%)
LCMS method 1: MH$^+$=542, RT=1.028 min Preparation of Intermediate 62

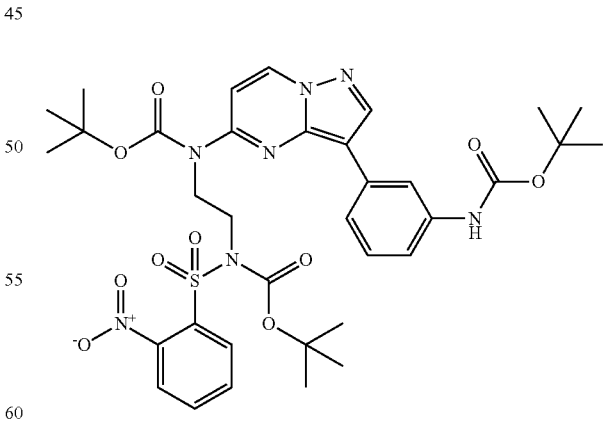

A mixture of intermediate 61 (12.70 g, 23.46 mmol), tert-butoxycarbonyl anhydride (5.63 g, 25.81 mmol) and 4-(dimethylamino)pyridine (143 mg, 1.17 mmol) in tetrahydrofuran (70.38 ml) was stirred at 55° C. for 5 hours. The reaction mixture was cooled and the solvent was removed under reduced pressure. The residue was purified by flash column chromatography over silica gel using heptane and ethyl acetate as eluents (gradient elution from 10% to 65% ethyl acetate). The product fractions were collected and the solvent was removed under reduced pressure. The residue was triturated with diethyl ether, filtered and dried under reduced pressure.
Yield: 14.7 g of intermediate 62 (98%)
LCMS method 2: MH$^+$=642, RT=4.593 min Preparation of Intermediate 63

A mixture of 1,4-dioxane and water (3:1, 9.36 ml) was degassed by bubbling nitrogen gas through the mixture. Intermediate 62 (2.00 g, 3.12 mmol), [3-(tert-butoxycarbonylamino)phenyl]boronic acid (780 mg, 3.28 mmol), tetrakis(triphenylphosphine)palladium(0) (70 mg, 0.06 mmol), 2-dicyclohexylphosphino-2',4',6'-triisopropylbiphenyl (Xphos) (119 mg, 0.25 mmol) and potassium phosphate tribasic (3.307 g, 5 eq.) were added and the mixture was stirred under nitrogen gas at 80° C. for 18 hours. The reaction mixture was cooled and the solvent was removed under reduced pressure. Ethyl acetate was added and the organic layer was washed with water. The organic layer was dried, filtered and the solvent was removed under reduced pressure. The product was used in the next step without further purification.

Preparation of Intermediate 64

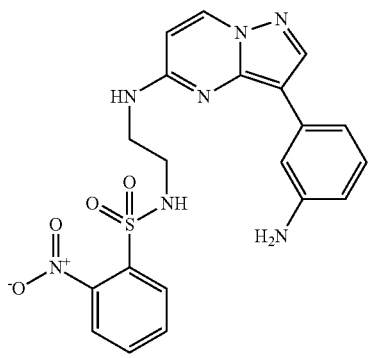

Intermediate 63 (2.351 g, 3.12 mmol) was dissolved in 2N HCl in methanol (9.36 ml) and the mixture was stirred at room temperature for 2 hours. The solvent was removed under reduced pressure. The residue was triturated with diethyl ether and the product was dried under reduced pressure. The residue was purified by flash column chromatography over silica gel using dichloromethane and methanol as eluents (gradient elution from 0% to 50% methanol). The product fractions were collected and the solvent was removed under reduced pressure.

Yield: 1.341 g of intermediate 63 (95%)

Preparation of Intermediate 65

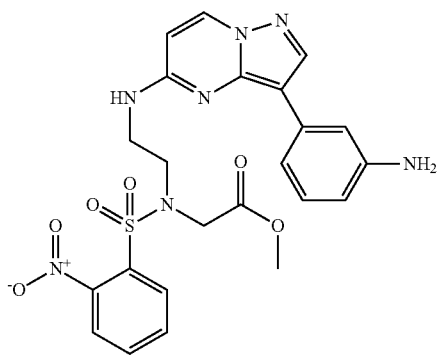

A mixture of intermediate 64 (1.341 g, 2.96 mmol), methyl 2-bromoacetate (300 mg, 3.11 mmol) and cesium carbonate (1.157 g, 3.55 mmol) was stirred overnight at 50° C. Water was added and the product was extracted with ethyl acetate. The organic layer was washed with brine, dried, filtered and the solvent was removed under reduced pressure. The residue was purified by flash column chromatography over silica gel using heptane and ethyl acetate as eluents (gradient elution from 0% to 100% ethyl acetate). The product fractions were collected and the solvent was removed under reduced pressure.

Yield: 1.321 g of intermediate 65 (85%)

LCMS method 1: MH$^+$=526, RT=0.791 min

Preparation of Intermediate 66

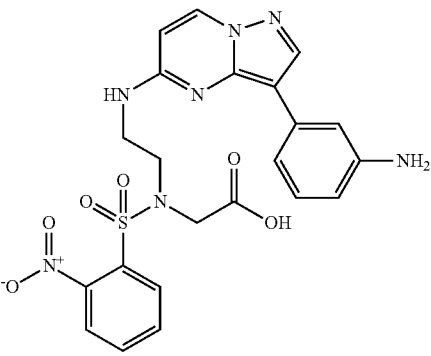

Intermediate 65 (1.321 g, 2.51 mmol) and lithium hydroxide monohydrate (190 mg, 2.76 mmol) in a mixture tetrahydrofuran/methanol/water (2:2:1, 7.53 ml) were stirred at room temperature for 2 hours. The solvent was removed under reduced pressure and the residue was used in the next step without further purification.

LCMS method 2: MH$^+$=512, RT=2.663 min

Preparation of Intermediate 67

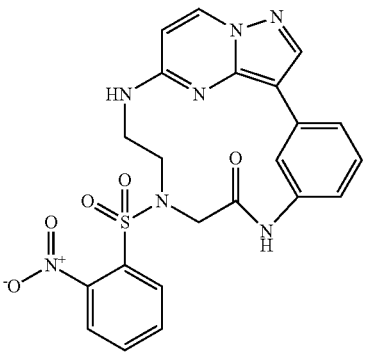

A suspension of intermediate 66 (1.59 g, 3.08 mmol) in N,N-dimethylformamide (100 ml) was added drop wise to a solution of O-(benzotriazol-1-yl)-N,N,N',N'-tetramethyluronium hexafluorophosphate (HBTU) (3.50 g, 9.24 mmol) and N,N-diisopropylethylamine (3.143 ml, 18.48 mmol) in N,N-dimethylformamide (200 ml). The mixture was stirred at room temperature for 1 hour. The reaction mixture was concentrated. Ethyl acetate was added and the organic layer was washed with a saturated aqueous sodium bicarbonate solution and brine. The organic layer was dried, filtered and the solvent was removed under reduced pressure. The residue was purified by flash column chromatography over silica gel using heptane and ethyl acetate as eluents (gradient elution from 20% to 100% ethyl acetate). The product fractions were collected and the solvent was removed under reduced pressure.

Yield: 290 mg of intermediate 67 (19%)

LCMS method 1: MH$^+$=494

Preparation of Example 16

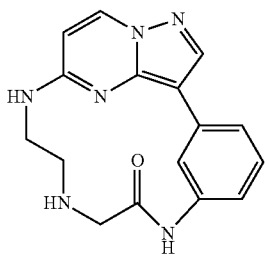 [SMILES: O=C1CNCCNc2ccn3ncc(c3n2)-c2cccc(c2)N1]

Cesium carbonate (384 mg, 1.18 mmol) and thiophenol (70 µl, 0.71 mmol) were suspended in N,N-dimethylformamide (1 ml) and the mixture was stirred at room temperature for 15 minutes. A solution of intermediate 66 (290 mg, 0.59 mmol) in N,N-dimethylformamide (1 ml) was added. The reaction mixture was stirred at room temperature for 3 hours. Sodium hydroxide (0.3 eq) was added and the solvent was removed under reduce pressure. The residue was purified by reversed phase column chromatography (HPLC method A). The product fractions were collected and the solvent was removed under reduced pressure.

Yield: 40 mg of example 16 (22%)
LCMS method 2: MH$^+$=309, RT=1.764 min

Example 17

Preparation of Example 17

Example 17 is prepared following general scheme 1.

Preparation of Intermediate 68

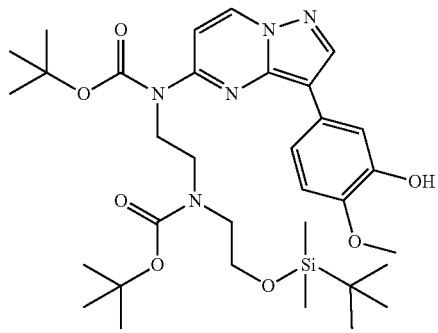 [SMILES: COc1ccc(-c2cnn3ccc(N(CCN(CCO[Si](C)(C)C(C)(C)C)C(=O)OC(C)(C)C)C(=O)OC(C)(C)C)nc23)cc1O]

A mixture of 1,4-dioxane and water (3:1, 7.32 ml) was degassed by bubbling nitrogen gas through the mixture. Intermediate 23 (1.50 g, 2.44 mmol), (3-hydroxy-4-methoxy-phenyl)boronic acid (430 mg, 2.56 mmol), tris(dibenzylideneacetone)dipalladium(0) (58 mg, 0.05 mmol), 2-dicyclohexylphosphino-2',4',6'-triisopropylbiphenyl (Xphos) (95 mg, 0.20 mmol) and potassium phosphate tribasic (2.826 g, 5 eq.) were added and the mixture was stirred under nitrogen gas at 80° C. for 18 hours. The reaction mixture was cooled, diluted with ethyl acetate and the organic layer was washed with water and brine. The organic layer was dried, filtered and the solvent was removed under reduced pressure. The product was used in the next step without further purification.

Yield: 1.124 g of intermediate 68 (70%)
LCMS method 1: MH$^+$=558 (MW—Boc), RT=1.517 min

Preparation of Intermediate 69

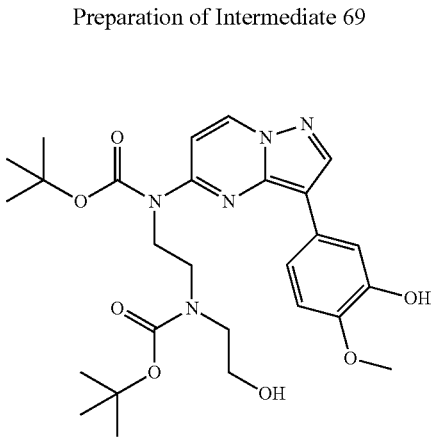

Tetrabutylammonium fluoride (1M solution in tetrahydrofuran, 2.05 ml, 2.05 mmol) was added to a solution of intermediate 68 (1.124 g, 1.71 mmol) in tetrahydrofuran (5.13 ml) and the mixture was stirred at room temperature for 3 hours. The solvent was removed under reduced pressure. Ethyl acetate was added and the organic layer was washed with water and brine. The organic layer was dried, filtered and the solvent was removed under reduced pressure. The residue was purified by flash column chromatography over silica gel using heptane and ethyl acetate as eluents. The product fractions were collected and the solvent was evaporated.

Yield: 749 mg of intermediate 69 (81%)
LCMS method 1: MH$^+$=444 (MW-Boc), RT=0.995 min

Preparation of Intermediate 70

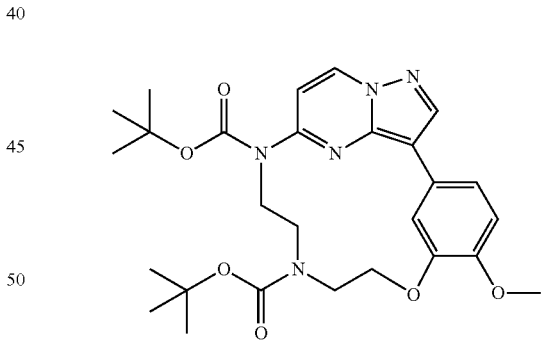

A solution of intermediate 69 (749 mg, 1.38 mmol) in 2-methyltetrahydrofuran (20 ml/mmol) and a solution of diisopropyl azodicarboxylate (820 µl, 4.14 mmol) in toluene (20 ml/mmol) were added simultaneously to a solution of triphenylphosphine (1.086 g, 4.14 mmol) in toluene (75 ml/mmol of intermediate 68). The mixture was stirred at 90° C. for 3 hours. The reaction mixture was cooled and the solvent was removed under reduced pressure. The residue was purified by flash column chromatography over silica gel using heptane and ethyl acetate as eluents (gradient elution from 0% to 80% ethyl acetate). The product fractions were collected and the solvent was evaporated.

Yield: 441 g of intermediate 70 (61%)

Preparation of Example 17

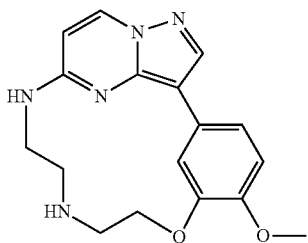 [SMILES: COc1ccc2cc1OCCNCCNc1ccn3ncc-2c3n1]

Intermediate 70 (441 mg, 0.84 mmol) was dissolved in 4N hydrochloric acid in methanol (2.52 ml). The mixture was stirred at room temperature for 2 hours. The solvent was removed under reduced pressure. The resulting solid was triturated in diethyl ether, filtered and dried under reduced pressure.

Yield: 125 mg of example 17 (46%)

LCMS method 2: $MH^+$=326, RT=1.636 min

Example 18

Preparation of Example 18

Example 18 is prepared following general scheme 1.

Preparation of Intermediate 71

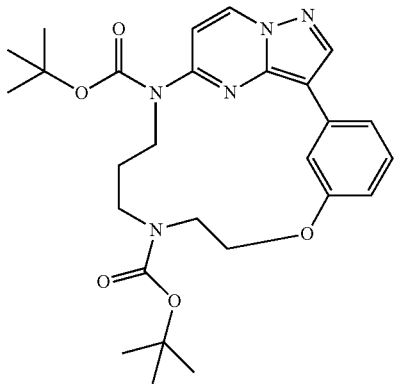 [SMILES: CC(C)(C)OC(=O)N1CCCN(C(=O)OC(C)(C)C)c2ccn3ncc(c3n2)-c2cccc(c2)OCC1]

Intermediate 70 was prepared according to the experimental procedures followed to obtain intermediate 69, except that tert-butyl N-(3-aminopropyl)-N-[2-(tert-butyl(dimethyl)silyl)oxyethyl]carbamate (prepared in the same way as intermediate 21) is being used for the coupling to the scaffold and (3-hydroxyphenyl)boronic acid for the Suzuki coupling. The ring closure was performed following the method described to obtain intermediate 69.

Yield: 700 mg of intermediate 71 (92%)

LCMS method 1: $MH^+$=510, RT=1.695 min

Preparation of Example 18

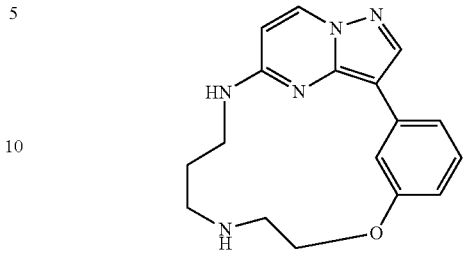

Intermediate 70 (700 mg, 1.37 mmol) was dissolved in 4N hydrochloric acid in methanol (4.11 ml). The mixture was stirred at room temperature for 2 hours. The solvent was removed under reduced pressure. The resulting solid was triturated in diethyl ether, filtered and dried under reduced pressure.

Yield: 387 mg of example 18 (82%)

LCMS method 2: $MH^+$=310, RT=1.753 min

Example 19

Preparation of Example 19

Example 19 is prepared following general scheme 2.

Preparation of Intermediate 72

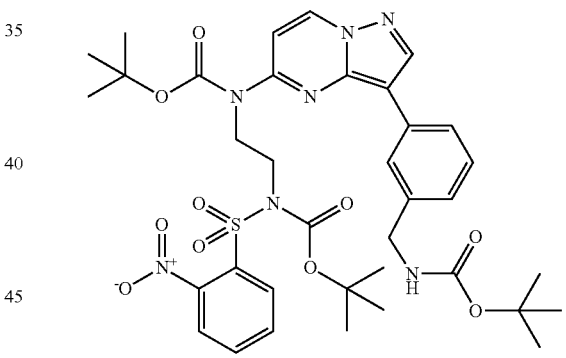

A mixture of 1,4-dioxane and water (3:1, 9.36 ml) was degassed by bubbling nitrogen gas through the mixture. Intermediate 62 (2.00 g, 3.12 mmol), [3-[(tert-butoxycarbonylamino)methyl]phenyl]boronic acid (820 mg, 3.28 mmol), tetrakis(triphenylphosphine)palladium(0) (70 mg, 0.06 mmol), 2-dicyclohexylphosphino-2',4',6'-triisopropylbiphenyl (Xphos) (119 mg, 0.25 mmol) and potassium phosphate tribasic (3.307 g, 5 eq.) were added and the mixture was stirred under nitrogen gas at 80° C. for 18 hours. The reaction mixture was cooled and the solvent was removed under reduced pressure. Ethyl acetate was added and the organic layer was washed with water. The organic layer was dried, filtered and the solvent was removed under reduced pressure. The residue was purified by flash column chromatography over silica gel using heptane and ethyl acetate as eluents (gradient elution from 0% to 50% ethyl acetate). The product fractions were collected and the solvent was removed under reduced pressure.

Yield: 1.70 g of intermediate 72 (71%)

Preparation of Intermediate 73

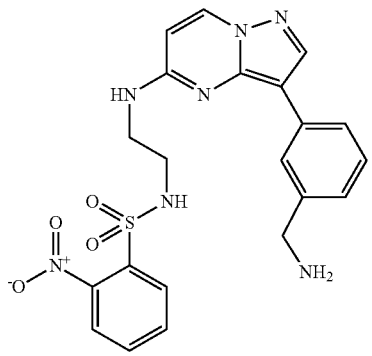

Intermediate 72 (2.396 g, 3.12 mmol) was dissolved in 2N HCl in methanol (9.36 ml) and the mixture was stirred at room temperature overnight. The solvent was removed under reduced pressure. The residue was triturated with diethyl ether and the product was dried under reduced pressure.

Yield: 1.174 g of intermediate 73 (80%)

Preparation of Intermediate 74

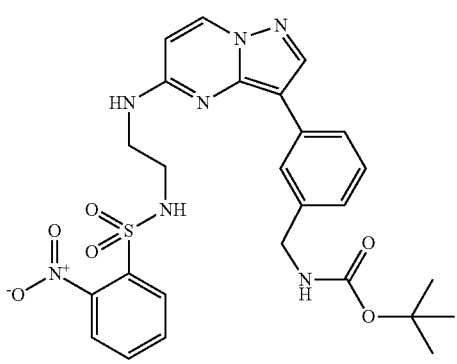

Tert-butoxycarbonyl anhydride (520 mg, 2.36 mmol) was added to a suspension of intermediate 73 (1.053 g, 2.25 mmol) in tetrahydrofuran (6.75 ml) and the mixture was stirred at room temperature for 4 hours. N,N-Diisopropylethylamine (383 µl, 2.25 mmol) was added and the reaction mixture was stirred at room temperature for 4 hours. More tert-butoxycarbonyl anhydride (245 mg, 1.125 mmol) was added and the reaction mixture was stirred at room temperature for 4 hours. The solvent was removed under reduced pressure. Ethyl acetate was added and the organic layer was washed with water and brine. The organic layer was dried, filtered and the solvent was removed under reduced pressure. The residue was purified by flash column chromatography over silica gel using heptane and ethyl acetate as eluents (gradient elution from 20% to 80% ethyl acetate). The product fractions were collected and the solvent was removed under reduced pressure.

Yield: 450 mg of intermediate 74 (35%)

Preparation of Intermediate 75

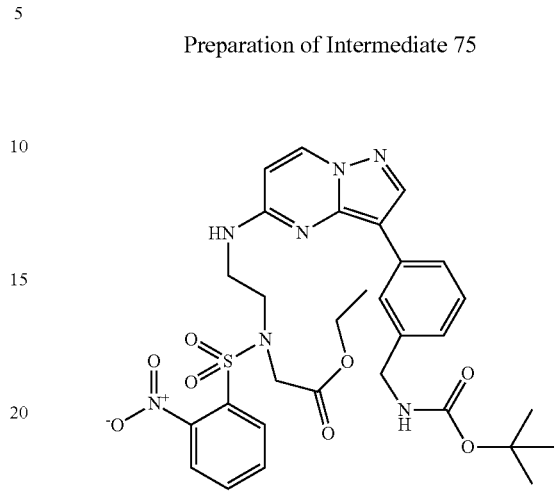

Diisopropyl azodicarboxylate (184 µl, 0.93 mmol) was dissolved in tetrahydrofuran (1.86 ml). Intermediate 74 (350 mg, 0.62 mmol) and ethyl 2-hydroxyacetate (90 µl, 0.93 mmol) were added and the mixture was stirred at room temperature for 15 minutes. Triphenylphosphine (244 mg, 0.93 mmol) was added and the mixture was stirred at room temperature overnight. Ethyl acetate was added and the organic layer was washed with water and brine. The organic layer was dried, filtered and the solvent was removed under reduced pressure. The residue was purified by flash column chromatography over silica gel using heptane and ethyl acetate as eluents (gradient elution from 0% to 100% ethyl acetate). The product fractions were collected and the solvent was removed under reduced pressure.

LCMS method 1: MH$^+$=654, RT=1.063 min

Preparation of Intermediate 76

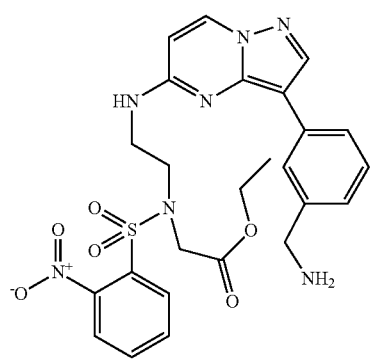

Intermediate 75 (558 mg, 0.85 mmol) was dissolved in a 4N HCl solution in 1,4-dioxane (15 ml). The suspension was stirred at room temperature overnight. The solvent was removed under reduced pressure and the residue was used in the next step without further purification.

Preparation of Intermediate 77

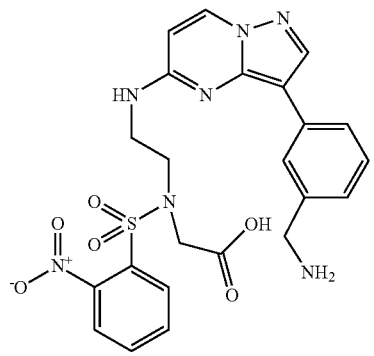

Intermediate 76 (756 mg, 1.37 mmol) and lithium hydroxide monohydrate (60 mg, 1.51 mmol) in a mixture tetrahydrofuran/methanol/water (2:2:1, 4.11 ml) were stirred at room temperature overnight. The solvent was removed under reduced pressure. The residue was purified by reversed phase HPLC (HPLC method A). The product fractions were collected and the solvent was removed under reduced pressure.

Yield: 85 mg of intermediate 77 (12%)

Preparation of Intermediate 78

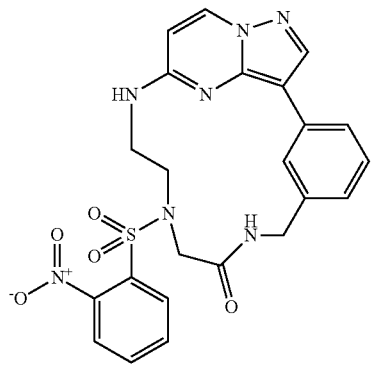

A suspension of intermediate 77 (85 mg, 0.16 mmol) in N,N-dimethylformamide (100 ml) was added drop wise to a solution of O-(benzotriazol-1-yl)-N,N,N',N'-tetramethyluronium hexafluorophosphate (HBTU) (180 mg, 0.48 mmol) and N,N-diisopropylethylamine (163 µl, 0.96 mmol) in N,N-dimethylformamide (200 ml). The mixture was stirred at room temperature for 1 hour. Ethyl acetate was added and the organic layer was washed with a saturated aqueous sodium bicarbonate solution and brine. The organic layer was dried, filtered and the solvent was removed under reduced pressure. The residue was purified by flash column chromatography over silica gel using dichloromethane and a mixture of dichloromethane/methanol (9:1) as eluents (gradient elution from 20% to 100% dichloromethane/methanol (9:1)). The product fractions were collected and the solvent was removed under reduced pressure.

Yield: 20 mg of intermediate 78 (25%)
LCMS method 1: MH$^+$=508, RT=0.766 min

Preparation of Example 19

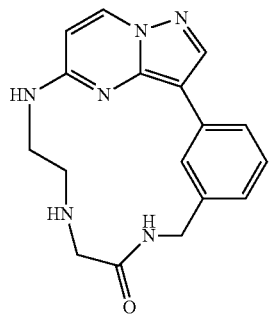 [SMILES: O=C1CNCCNc2ccn3ncc(c3n2)-c2cccc(c2)CN1]

Cesium carbonate (26 mg, 0.08 mmol) and thiophenol (10 µl, 0.05 mmol) were suspended in N,N-dimethylformamide (60 µl) and the mixture was stirred at room temperature for 15 minutes. A solution of intermediate 81 (20 mg, 0.04 mmol) in N,N-dimethylformamide (60 µl) was added. The reaction mixture was stirred at room temperature for 3 hours. Ethyl acetate was added and the organic layer was washed with a 1N aqueous sodium hydroxide solution. The organic layer was dried, filtered and the solvent was removed under reduce pressure. The residue was triturated with diethyl ether, filtered and the product was dried under reduced pressure.

Yield: 5 mg of example 19 (39%)
LCMS method 2: MH$^+$=323, RT=1.515 min

Preparation of Example 20

Example 20 is prepared following general scheme 1.

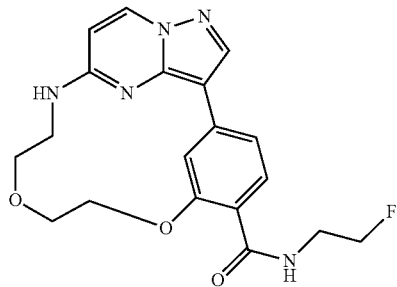 [SMILES: O=C(NCCF)c1ccc2cc1OCCOCCNc1ccn3ncc-2c3n1]

O-(Benzotriazol-1-yl)-N,N,N',N'-tetramethyluronium hexafluorophosphate (HBTU) (656 mg, 1.73 mmol) was added to a suspension of example 1 (600 mg, 1.73 mmol), 2-fluoroethanamine hydrochloride (170 mg, 1.73 mmol) and N,N-diisopropylethylamine (754 µl, 4.33 mmol) in N,N-dimethylformamide (10 ml). The mixture was stirred at room temperature for 5 hours. The reaction mixture was concentrated under reduced pressure and ethyl acetate was added. The organic layer was washed with water and the water layer was extracted with dichloromethane. The combined organic layers were dried, filtered and the solvent was removed under reduced pressure. The residue was purified by reversed phase HPLC (HPLC method A). The product fractions were collected and neutralized by addition of solid sodium carbonate. The product was extracted with dichloromethane. The combined organic layers were dried, filtered and the solvent was removed under reduced pressure.

Yield: 28 mg of example 20 (4%)

LCMS method 2: MH$^+$=386, RT=2.527 min

Preparation of Example 21

Example 21 is prepared following general scheme 1.

Preparation of Intermediate 79

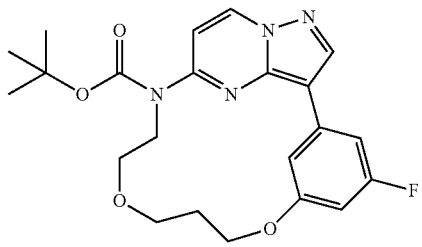 [SMILES: CC(C)(C)OC(=O)N1CCOCCCOc2cc(F)cc(c2)-c2cnn3ccc1nc23]

Intermediate 79 was prepared according to the experimental procedures followed to obtain intermediate 9, except that 3-(2-aminoethoxy)propan-1-ol is being used for the coupling to the scaffold and (3-fluoro-5-hydroxy-phenyl)boronic acid for the Suzuki coupling. The ring closure was performed following the method described to obtain intermediate 9.

Yield: 430 mg of intermediate 79 (54%)

LCMS method 1: MH$^+$=429, RT=1.291 min

Preparation of Example 21

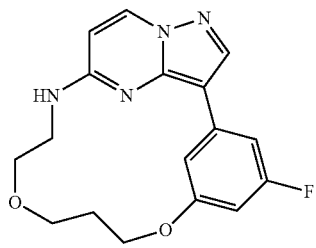

Intermediate 79 (430 mg, 1.00 mmol) was dissolved in 4N hydrochloric acid in methanol (20 ml). The mixture was stirred at room temperature for 2 hours. The solvent was removed under reduced pressure. The resulting solid was triturated in methanol, filtered and dried under reduced pressure.

Yield: 270 mg of example 21 (83%)

LCMS method 2: MH$^+$=329, RT=3.347 min

The compounds in Table 1 were prepared by analogy to one of the procedures described above.

TABLE 1

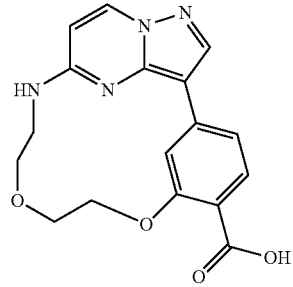

Compound 1, Example 1

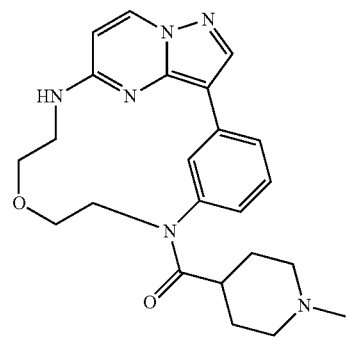

Compound 2, Example 2

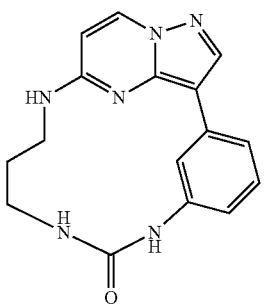

Compound 3, Example 3

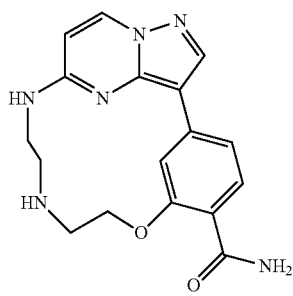

Compound 4, Example 4

TABLE 1-continued
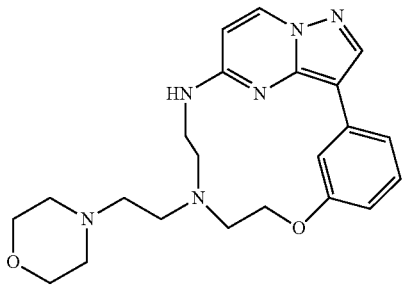
Compound 5, Example 5
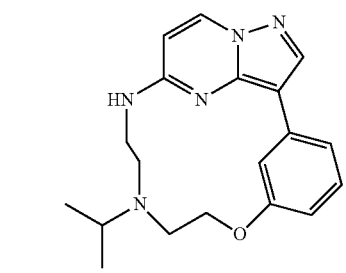
Compound 6, Example 6
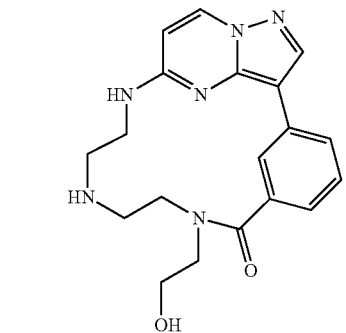
Compound 7, Example 7
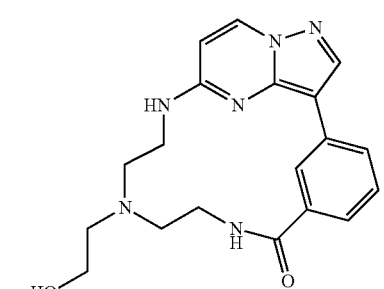
Compound 8, Example 8
TABLE 1-continued
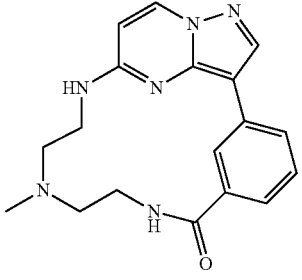
Compound 9, Example 9
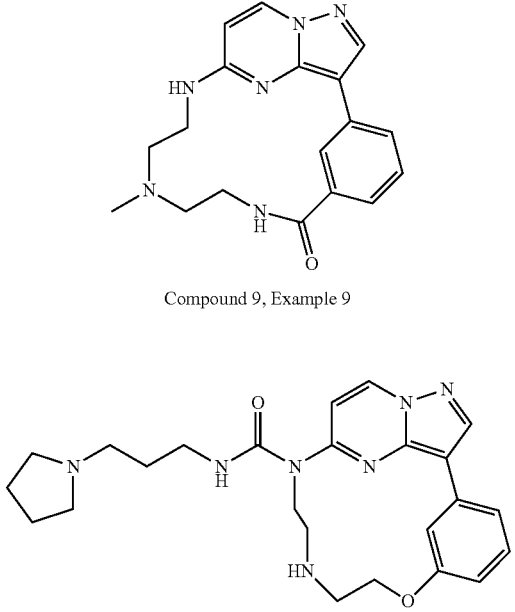
Compound 10, Example 10
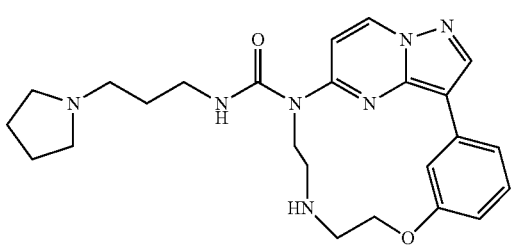
Compound 11, Example 11
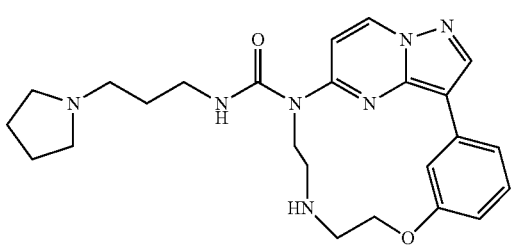
Compound 12, Example 12
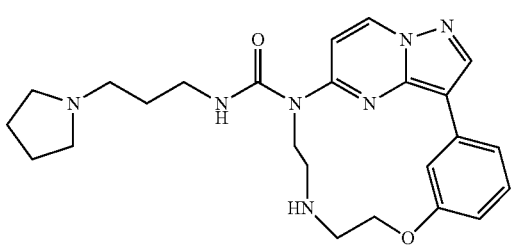
Compound 13, Example 13

TABLE 1-continued
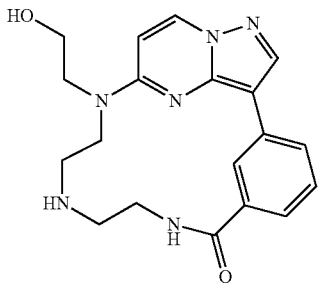
Compound 14, Example 14
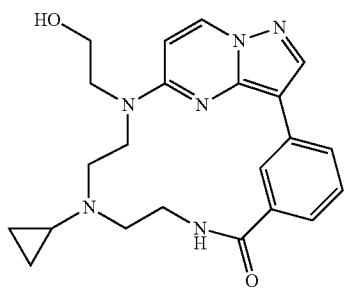
Compound 15, Example 15
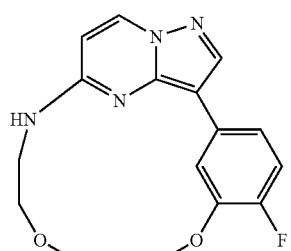
Compound 16
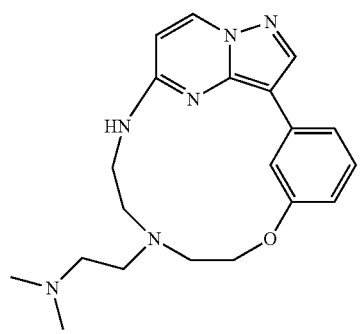
Compound 17
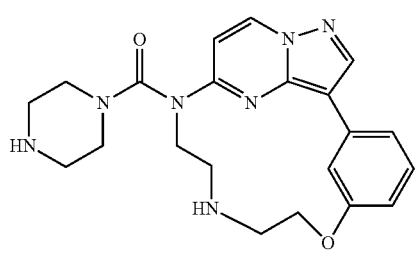
Compound 18
TABLE 1-continued
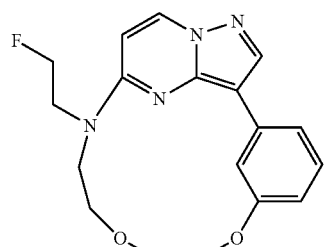
Compound 19
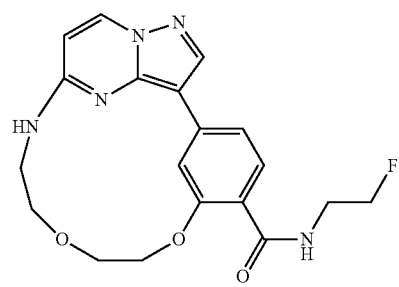
Compound 20, Example 20
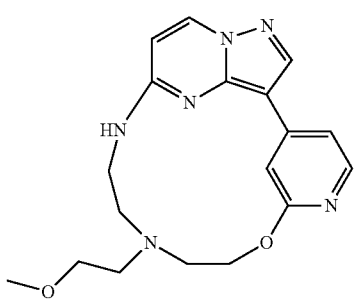
Compound 21
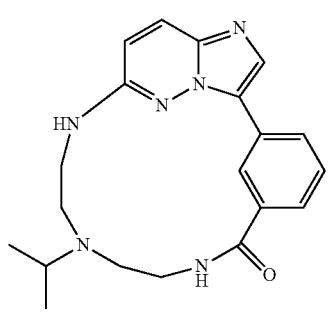
Compound 22
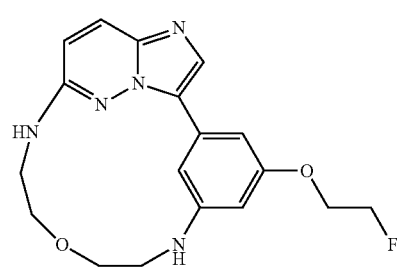
Compound 23

TABLE 1-continued
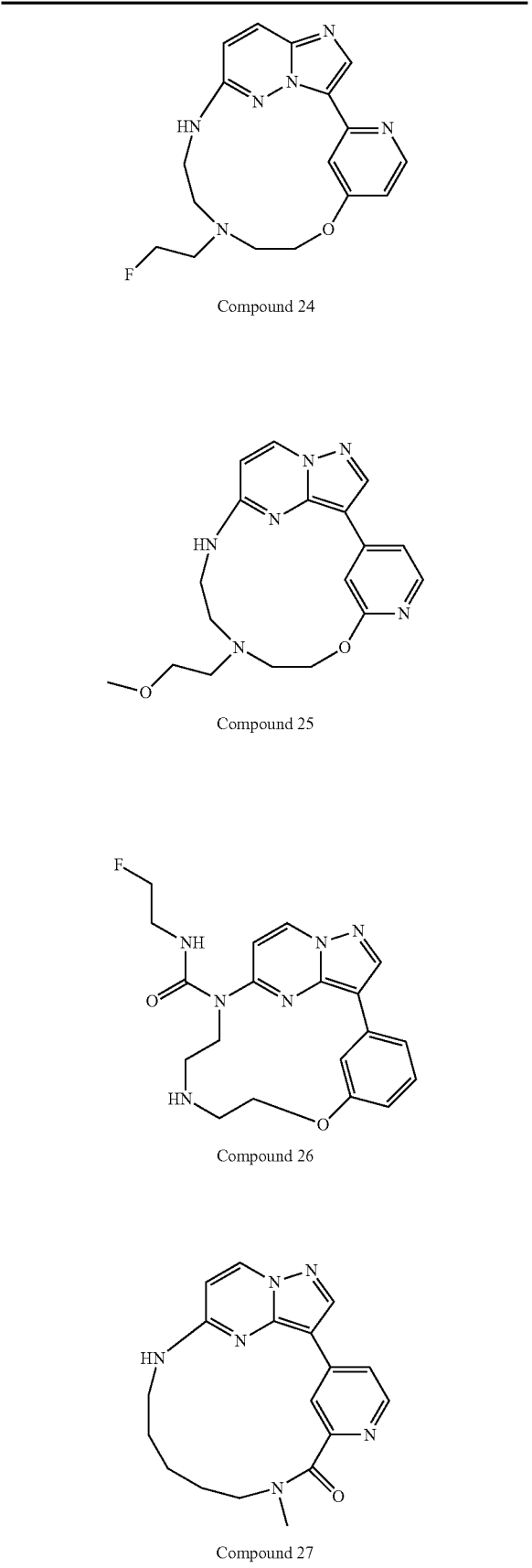
Compound 24
Compound 25
Compound 26
Compound 27
TABLE 1-continued
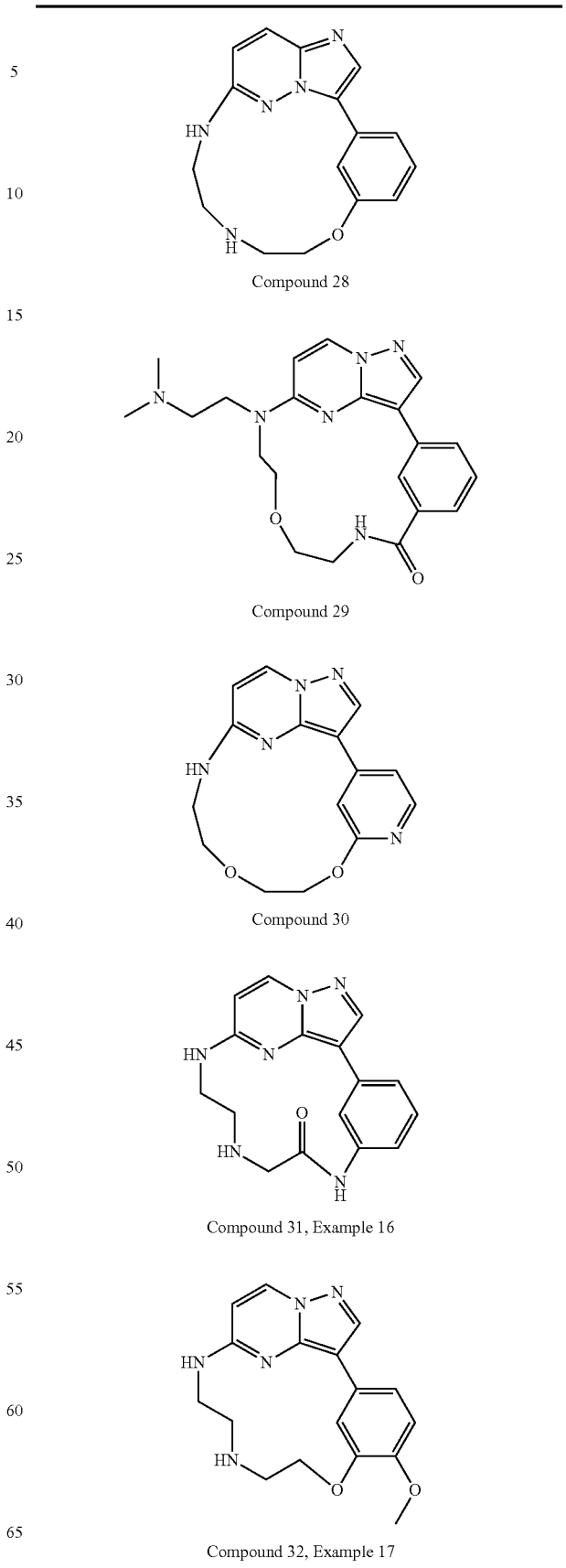
Compound 28
Compound 29
Compound 30
Compound 31, Example 16
Compound 32, Example 17

TABLE 1-continued

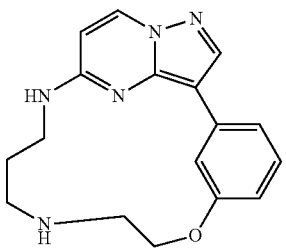

Compound 33, Example 18

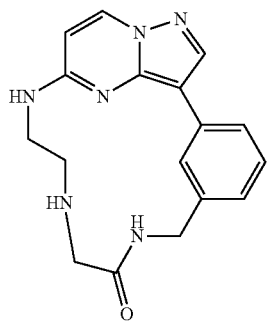

Compound 34, Example 19

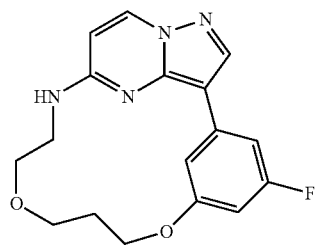 [SMILES: Fc1cc2cc(c1)-c1cnn3ccc(nc13)NCCOCCCO2]

Compound 35, Example 21

Compound Identification

Melting Points

For the melting point determination of the compounds of the present invention, the following method was used.

Melting Point Method

For a number of compounds, melting points (m.p.) were determined in open capillary tubes on a Mettler FP62 apparatus. Melting points were measured with a temperature ranging from 50° C. to 300° C., using a gradient of 10° C./minute. The melting point value was read from a digital display and was not corrected.

TABLE 2

Melting points

| COMPOUND NUMBER | MELTING POINT (° C.) |
|---|---|
| 1 | >300 |
| 2 | >300 |
| 3 | >300 |
| 4 | >300 |
| 5 | >300 |
| 6 | >300 |
| 7 | 271.6 |
| 8 | 283.9 |
| 9 | 287.6 |
| 10 | >300 |

TABLE 2-continued

Melting points

| COMPOUND NUMBER | MELTING POINT (° C.) |
|---|---|
| 11 | >300 |
| 12 | >300 |
| 13 | >300 |
| 14 | ND* |
| 15 | ND* |
| 20 | >300 |
| 31 | ND* |
| 32 | ND* |
| 33 | ND* |
| 34 | ND* |
| 35 | 234.9 |

*Not determined

LCMS

For LCMS-characterization of the compounds of the present invention, the following method was used.

General Procedure LCMS

All analyses were performed using an Agilent 6110 series LC/MSD quadrupole coupled to an Agilent 1290 series liquid chromatography (LC) system consisting of a binary pump with degasser, autosampler, thermostated column compartment and diode array detector. The mass spectrometer (MS) was operated with an atmospheric pressure electro-spray ionisation (API-ES) source in positive ion mode. The capillary voltage was set to 3000 V, the fragmentor voltage to 70 V and the quadrupole temperature was maintained at 100° C. The drying gas flow and temperature values were 12.0 L/min and 350° C. respectively. Nitrogen was used as the nebulizer gas, at a pressure of 35 psig. Data acquisition was performed with Agilent Chemstation software.

LCMS Method 1

In addition to the general procedure LCMS1: Analyses were carried out on a Phenomenex Kinetex C18 column (50 mm long×2.1 mm i.d.; 1.7 μm particles) at 60° C., with a flow rate of 1.5 mL/min. A gradient elution was performed from 90% (water+0.1% formic acid)/10% Acetonitrile to 10% (water+0.1% formic acid)/90% acetonitrile in 1.50 minutes, then the final mobile phase composition was held for an additional 0.40 min. The standard injection volume was 2 μL. Acquisition ranges were set to 254 nm for the UV-PDA detector and 80-800 m/z for the MS detector.

LCMS Method 2

In addition to the general procedure LCMS1: Analyses were carried out on a YMC pack ODS-AQ C18 column (50 mm long×4.6 mm i.d.; 3 μm particles) at 35° C., with a flow rate of 2.6 mL/min. A gradient elution was performed from 95% (water+0.1% formic acid)/5% Acetonitrile to 5% (water+0.1% formic acid)/95% Acetonitrile in 4.80 minutes, then the final mobile phase composition was held for an additional 1.00 min. The standard injection volume was 2 μL. Acquisition ranges were set to 190-400 nm for the UV-PDA detector and 100-1400 m/z for the MS detector.

TABLE 3

LCMS data

| COMPOUND NUMBER | MASS (MH)+ PEAK | RETENTION TIME (min) | LCMS METHOD |
|---|---|---|---|
| 1 | 341 | 2.252 | 2 |
| 2 | 421 | 1.650 | 2 |
| 3 | 309 | 2.181 | 2 |
| 4 | 339 | 1.245 | 2 |

TABLE 3-continued

LCMS data

| COMPOUND NUMBER | MASS (MH)+ PEAK | RETENTION TIME (min) | LCMS METHOD |
|---|---|---|---|
| 5 | 409 | 1.834 | 2 |
| 6 | 338 | 1.751 | 2 |
| 7 | 367 | 1.240 | 2 |
| 8 | 367 | 1.263 | 2 |
| 9 | 337 | 1.288 | 2 |
| 10 | 451 | 1.180 | 2 |
| 11 | 410 | 1.131 | 2 |
| 12 | 327 | 2.223 | 2 |
| 13 | 408 | 1.926 | 2 |
| 14 | 367 | 1.201 | 2 |
| 15 | 407 | 1.105 | 2 |
| 20 | 386 | 2.527 | 2 |
| 31 | 309 | 1.764 | 2 |
| 32 | 326 | 1.636 | 2 |
| 33 | 310 | 1.753 | 2 |
| 34 | 323 | 1.515 | 2 |
| 35 | 329 | 3.347 | 2 |

B. Kinase Activity Assay

The inhibition of FLT3 kinase was assessed using FLT3 recombinant protein in an in vitro peptide-based kinase assay.
Protocol 1

In a final reaction volume of 25 µL, Flt3 (h) (5-10 mU) is incubated with 8 mM MOPS pH 7.0, 0.2 mM EDTA, 50 µM EAIYAAPFAKKK, 10 mM MgAcetate and [g-33P-ATP] (specific activity approx. 500 cpm/pmol, concentration as required). The reaction is initiated by the addition of the MgATP mix. After incubation for 40 minutes at room temperature, the reaction is stopped by the addition of 5 µL of a 3% phosphoric acid solution. 10 µL of the reaction is then spotted onto a P30 filtermat and washed three times for 5 minutes in 75 mM phosphoric acid and once in methanol prior to drying and scintillation counting.

The inhibition of FLT3 D835Y mutant kinase was assessed using FLT3 D835Y mutant recombinant protein in an in vitro peptide-based kinase assay.

In a final reaction volume of 25 µL, Flt3 (D835Y) (h) (5-10 mU) is incubated with 8 mM MOPS pH 7.0, 0.2 mM EDTA, 50 µM EAIYAAPFAKKK, 10 mM MgAcetate and [g-33P-ATP] (specific activity approx. 500 cpm/pmol, concentration as required). The reaction is initiated by the addition of the MgATP mix. After incubation for 40 minutes at room temperature, the reaction is stopped by the addition of 5 µL of a 3% phosphoric acid solution. 10 µL of the reaction is then spotted onto a P30 filtermat and washed three times for 5 minutes in 75 mM phosphoric acid and once in methanol prior to drying and scintillation counting.
Protocol 2

A radiometric protein kinase assay (33 PanQinase® Activity Assay) was used for measuring the kinase activity. All kinase assays were performed in 96-well FlashPlates™ from PerkinElmer (Boston, Mass., USA) in a 50 µl reaction volume. The reaction cocktail was pipetted in four steps in the following order:

20 µl of assay buffer (standard buffer)
  5 µl of ATP solution (in H2O)
  5 µl of test compound (in 10% DMSO)
  10 µl of substrate/10 µl of enzyme solution (premixed)

The assay for FLT3 wt contains 70 mM HEPES-NaOH pH 7.5, 3 mM $MgCl_2$, 3 mM $MnCl_2$, 3 µM Na-orthovanadate, 1.2 mM DTT, ATP (3 µM), [γ-$^{33}$P]-ATP (approx. 5×1005 cpm per well), protein kinase FLT3 wt (6.1 nM) and substrate (poly(Ala,Glu,Lys,Tyr)6:2:5:1), 0.125 µg/50 µl).

The assay for FLT3 D835Y contains 70 mM HEPES-NaOH pH 7.5, 3 mM $MgCl_2$, 3 mM $MnCl_2$, 3 µM Na-orthovanadate, 1.2 mM DTT, ATP (0.3 µM), [γ-$^{33}$P]-ATP (approx. 5×1005 cpm per well), protein kinase FLT3 D835Y (4.1 nM) and substrate (poly(Ala,Glu,Lys,Tyr)6:2:5:1), 0.5 µg/50 µl).

The kinases are obtained from Invitrogen Corporation.

The reaction cocktails were incubated at 30° C. for 60 minutes. The reaction was stopped with 50 µl of 2% (v/v) H3PO4, plates were aspirated and washed two times with 200 µl 0.9% (w/v) NaCl. Incorporation of 33Pi was determined with a microplate scintillation counter.

Table 4 provides the $IC_{50}$ values of the compounds according to the invention, obtained using the above mentioned kinase assay.

| COMPOUND | $IC_{50}$ for FLT3 | $IC_{50}$ for FLT3 D835Y | Protocol |
|---|---|---|---|
| 1 | +++ | +++ | 1 |
| 2 | + | + | 1 |
| 3 | +++ | +++ | 1 |
| 4 | +++ | +++ | 1 |
| 5 | +++ | +++ | 1 |
| 6 | +++ | +++ | 1 |
| 7 | ++ | ++ | 1 |
| 8 | +++ | +++ | 1 |
| 9 | ++ | +++ | 1 |
| 10 | +++ | +++ | 1 |
| 11 | ++ | +++ | 1 |
| 12 | +++ | +++ | 1 |
| 13 | + | +++ | 1 |
| 14 | + | ++ | 1 |
| 15 | ++ | +++ | 1 |
| 20 | ND* | ND* | 1 |
| 31 | + | + | 2 |
| 32 | ++ | +++ | 2 |
| 33 | ++ | +++ | 2 |
| 34 | + | ++ | 2 |
| 35 | ND* | ND* | 2 |

+ indicates an IC50 > 1 µM,
++ indicates an IC50 of between 100 nM and 1 µM, and
+++ indicates an IC50 < 100 nM
*Not determined

The invention claimed is:

1. A compound of Formula I or a stereoisomer, tautomer, racemic, pharmaceutically acceptable salt, or N-oxide form thereof,

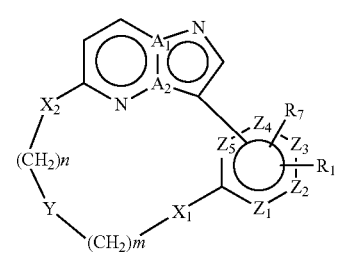

I

Wherein
  $A_1$ and $A_2$ are selected from C and N; wherein when $A_1$ is C, then $A_2$ is N; and wherein when $A_2$ is C, then $A_1$ is N;
  $R_1$ and $R_7$ are each independently selected from —H, -halo, —OH, —$C_{1-6}$alkyl, —O—$C_{1-6}$alkyl, —S—$C_{1-6}$alkyl, —$NR_9R_{10}$, —(C=O)—$R_4$, —$SO_2$—$R_4$, —CN, —$NR_9$—$SO_2$—$R_4$, —$C_{3-6}$cycloalkyl, and -$Het_6$;
  wherein each of said $C_{1-6}$alkyl is optionally and independently substituted with from 1 to 3 substituents selected from -halo, —OH, —NR$_{11}$R$_{12}$, —O—C$_{1-6}$alkyl, and —S—C$_{1-6}$alkyl;

R$_2$ is selected from —H, -halo, —OH, —C$_{1-6}$alkyl, —O—C$_{1-6}$alkyl, —S—C$_{1-6}$alkyl, —(C═O)—C$_{1-6}$alkyl, —(C═O)—O—C$_{1-6}$alkyl, —(C═O)—NR$_{27}$R$_{28}$, -Het$_3$, —(C═O)-Het$_3$, —SO$_2$—C$_{1-6}$alkyl, and —C$_{3-6}$cycloalkyl; wherein each of said C$_{1-6}$alkyl is optionally and independently substituted with from 1 to 3 substituents selected from -halo, —OH, —O—C$_{1-6}$alkyl, —S—C$_{1-6}$alkyl, -Het$_3$, —Ar$_2$, and —NR$_{13}$R$_{14}$;

R$_3$ is selected from —H, -halo, —OH, —C$_{1-6}$alkyl, —O—C$_{1-6}$alkyl, —S—C$_{1-6}$alkyl, —(C═O)—C$_{1-6}$alkyl, —(C═O)—O—C$_{1-6}$alkyl, -Het$_2$, —C$_{3-6}$cycloalkyl —(C═O)-Het$_2$, —(C═O)—NR$_{29}$R$_{30}$, and —SO$_2$—C$_{1-6}$alkyl; wherein each of said C$_{1-6}$alkyl is optionally and independently substituted with from 1 to 3 substituents selected from -halo, —OH, —O—C$_{1-6}$alkyl, —S—C$_{1-6}$alkyl, —NR$_{15}$R$_{16}$, -Het$_2$, and —Ar$_3$;

R$_4$ is independently selected from -halo, —OH, —C$_{1-6}$alkyl, —O—C$_{1-6}$alkyl, —S—C$_{1-6}$alkyl, —NR$_{17}$R$_{18}$, and -Het$_4$;

R$_5$ is selected from —H —C$_{1-6}$alkyl, and —C$_{3-6}$cycloalkyl; wherein each of said C$_{1-6}$alkyl is optionally and independently substituted with from 1 to 3 substituents selected from -halo, —OH, —OC$_{1-6}$alkyl, —SC$_{1-6}$alkyl, -Het$_5$, and —NR$_{31}$R$_{32}$;

R$_6$ is selected from —H, —OH, -halo, —C$_{1-6}$alkyl, —O—C$_{1-6}$alkyl, —S—C$_{1-6}$alkyl, —NR$_{33}$R$_{34}$, and -Het$_8$;

R$_9$, R$_{10}$, R$_{11}$, R$_{12}$, R$_{13}$, R$_{14}$, R$_{15}$, R$_{16}$, R$_{17}$, R$_{18}$, R$_{19}$, R$_{20}$, R$_{21}$, R$_{22}$, R$_{23}$, R$_{24}$, R$_{25}$, R$_{26}$, R$_{27}$, R$_{28}$, R$_{29}$, R$_{30}$, R$_{31}$, R$_{32}$, R$_{33}$, and R$_{34}$ are each independently selected from —H, —O, —C$_{1-6}$alkyl, and Het$_1$; wherein each of said C$_{1-6}$alkyl is optionally and independently substituted with from 1 to 3 substituents selected from -halo, —OH, —O—C$_{1-6}$alkyl, —S—C$_{1-6}$alkyl, —NR$_{35}$R$_{36}$, -Het$_7$, and —Ar$_4$;

R$_{35}$ and R$_{36}$ are each independently selected from —H, —O, and C$_{1-6}$alkyl; wherein each of said C$_{1-6}$alkyl is optionally and independently substituted with from 1 to 3 substituents selected from -halo, —OH, —O—C$_{1-6}$alkyl, and —S—C$_{1-6}$alkyl;

X$_1$ is selected from —C$_{1-6}$alkyl-, —O—C$_{1-6}$alkyl-, —S—C$_{1-6}$alkyl-, —(C═O)—, —NR$_3$—(C═O)—, —C$_{1-6}$alkyl-NR$_3$—(C═O)—, —NR$_3$—(C═O)—NR$_{35}$—, —NR$_3$—C$_{1-6}$alkyl-, —NR$_3$—, and —NR$_3$—SO$_2$—; wherein each of said C$_{1-6}$alkyl is optionally and independently substituted with from 1 to 3 substituents selected from -halo, —OH, —C$_{1-6}$alkyl, —O—C$_{1-6}$alkyl, —S—C$_{1-6}$alkyl, and —NR$_{23}$R$_{24}$;

X$_2$ is selected from —C$_{1-6}$alkyl-, —O—C$_{1-6}$alkyl-, —S—C$_{1-6}$alkyl-, —(C═O)—, —NR$_2$—(C═O)—, —NR$_2$—C$_{1-6}$alkyl-, —NR$_2$—, and —SO$_2$—NR$_2$—; wherein each of said C$_{1-6}$alkyl is optionally and independently substituted with from 1 to 3 substituents selected from -halo, —OH, —C$_{1-6}$alkyl, —O—C$_{1-6}$alkyl, —S—C$_{1-6}$alkyl, and —NR$_{25}$R$_{26}$;

Y is selected from a direct bond, —CHR$_6$—, —O—, —S—, and —NR$_5$—;

Ar$_2$, Ar$_3$, and Ar$_4$ are each independently a 5- or 6-membered aryl optionally comprising 1 or 2 heteroatoms selected from O, N and S; wherein each of said Ar$_2$, Ar$_3$, and Ar$_4$ is optionally and independently substituted with from 1 to 3 substituents selected from —NR$_{19}$R$_{20}$, —C$_{1-6}$alkyl, —O—C$_{1-6}$alkyl, and —S—C$_{1-6}$alkyl;

Het$_1$, Het$_2$, Het$_3$, Het$_4$, Het$_5$, Het$_6$, Het$_7$ and Het$_8$ are each independently a 5- or 6-membered monocyclic heterocycle having from 1 to 3 heteroatoms selected from O, N and S, wherein each heterocycle is optionally substituted with from 1 to 3 substituents selected from —C$_{1-6}$alkyl, —OC$_{1-6}$alkyl, —SC$_{1-6}$alkyl, and —NR$_{21}$R$_{22}$; wherein each of said C$_{1-6}$alkyl is optionally and independently substituted with from 1 to 3 -halo;

Z$_1$, Z$_2$, Z$_3$, Z$_4$ and Z$_5$ are each independently selected from C and N; and m and n are each independently 1, 2, 3, or 4.

2. A compound as defined in claim 1, wherein:

A$_1$ and A$_2$ are selected from C and N; wherein when A$_1$ is C, then A$_2$ is N; and wherein when A$_2$ is C, then A$_1$ is N;

R$_1$ is selected from —H, -halo, —OH, —C$_{1-6}$alkyl, —O—C$_{1-6}$alkyl, —NR$_9$R$_{10}$, —(C═O)—R$_4$, —CN, —NR$_9$—SO$_2$—R$_4$, and -Het$_6$; wherein each of said C$_{1-6}$alkyl is optionally and independently substituted with from 1 to 3 substituents selected from -halo, —OH, and —NR$_{11}$R$_{12}$;

R$_7$ is selected from —H, and -halo;

R$_2$ is selected from —H, —C$_{1-6}$alkyl, —(C═O)—NR$_{27}$R$_{28}$, —(C═O)-Het$_3$, and —SO$_2$—C$_{1-6}$alkyl; wherein each of said C$_{1-6}$alkyl is optionally and independently substituted with from 1 to 3 substituents selected from -halo, —OH, —O—C$_{1-6}$alkyl, -Het$_3$, and —NR$_{13}$R$_{14}$;

R$_3$ is selected from —H, —C$_{1-6}$alkyl, —(C═O)—C$_{1-6}$alkyl, —(C═O)-Het$_2$, —(C═O)—NR$_{29}$R$_{30}$, and —SO$_2$—C$_{1-6}$ alkyl; wherein each of said C$_{1-6}$alkyl is optionally and independently substituted with from 1 to 3 substituents selected from -halo, —OH, and —O—C$_{1-6}$alkyl;

R$_4$ is independently selected from —OH, —O—C$_{1-6}$alkyl, —NR$_{17}$R$_{18}$, and -Het$_4$;

R$_5$ is selected from —H, —C$_{1-6}$alkyl, and —C$_{3-6}$cycloalkyl; wherein each of said C$_{1-6}$alkyl is optionally and independently substituted with from 1 to 3 substituents selected from -halo, —OH, —OC$_{1-6}$alkyl, -Het$_5$, and —NR$_{31}$R$_{32}$;

R$_6$ is selected from —OH, and —NR$_{33}$R$_{34}$;

R$_9$, R$_{10}$, R$_{11}$, R$_{12}$, R$_{13}$, R$_{14}$, R$_{17}$, R$_{18}$, R$_{27}$, R$_{28}$, R$_{29}$, R$_{30}$, R$_{31}$, R$_{32}$, R$_{33}$, and R$_{34}$ are each independently selected from —H, —C$_{1-6}$alkyl, —NR$_{35}$R$_{36}$ or Het$_1$; wherein each of said C$_{1-6}$alkyl is optionally and independently substituted with from 1 to 3 substituents selected from -halo, —OH, and -Het$_7$;

R$_{35}$ and R$_{36}$ are each independently selected from —H, —O, and C$_{1-6}$alkyl; wherein each of said C$_{1-6}$alkyl is optionally and independently substituted with from 1 to 3 substituents selected from -halo, —OH, —O—C$_{1-6}$alkyl, and —S—C$_{1-6}$alkyl;

X$_1$ is selected from —C$_{1-6}$alkyl-, —O—C$_{1-6}$alkyl-, —S—C$_{1-6}$alkyl-, —(C═O)—, —NR$_3$—(C═O)—, —C$_{1-6}$alkyl-NR$_3$—(C═O)—, —NR$_3$—(C═O)—NR$_{35}$—, —NR$_3$—C$_{1-6}$alkyl-, and —NR$_3$—SO$_2$—;

X$_2$ is selected from —C$_{1-6}$alkyl-, —O—C$_{1-6}$alkyl-, —(C═O)—NR$_2$—, and —NR$_2$—C$_{1-6}$alkyl-;

Y is selected from a direct bond, —CHR$_6$—, —O—, —S—, and —NR$_5$—;

Het$_1$, Het$_2$, Het$_3$, Het$_4$, Het$_5$, Het$_6$, and Het$_7$ are each independently a 5- or 6-membered monocyclic heterocycle having from 1 to 3 heteroatoms selected from O, N and S, wherein each heterocycle is being optionally substituted with from 1 to 3 —C$_{1-6}$alkyl; each of said C$_{1-6}$alkyl being optionally and independently substituted with from 1 to 3 -halo $Z_1$, $Z_2$, $Z_3$, $Z_4$ and $Z_5$ are each independently selected from C and N; and m and n are each independently 1, 2, 3, or 4.

3. A compound as defined in claim 1, wherein:

$A_1$ and $A_2$ are selected from C and N; wherein when $A_1$ is C, then $A_2$ is N; and wherein when $A_2$ is C, then $A_1$ is N;

$R_1$ is selected from —H, -halo, —OH, —$C_{1-2}$alkyl, —O—$C_{1-2}$alkyl, —$NR_9R_{10}$, —(C=O)—$R_4$, —CN, —$NR_9$—$SO_2$—$R_4$, and -$Het_6$; wherein each of said $C_{1-2}$alkyl is optionally and independently substituted with from 1 to 3 substituents selected from -halo, —OH, and —$NR_{11}R_{12}$;

$R_7$ is selected from —H, and -halo;

$R_2$ is selected from —H, —$C_{1-3}$alkyl, —(C=O)—$NR_{27}R_{28}$, —(C=O)-$Het_3$, and —$SO_2$—$C_{1-3}$alkyl; wherein each of said $C_{1-3}$alkyl is optionally and independently substituted with from 1 to 3 substituents selected from -halo, —OH, —O—$CH_3$, -$Het_3$, and —$NR_{13}R_{14}$;

$R_3$ is selected from —H, —$C_{1-2}$alkyl, —(C=O)—$C_{1-2}$alkyl, —(C=O)-$Het_2$, —(C=O)—$NR_{29}R_{30}$, and —$SO_2$—$C_{1-2}$alkyl; wherein each of said $C_{1-2}$alkyl is optionally and independently substituted with from 1 to 3 substituents selected from -halo, —OH, and —O—$CH_3$;

$R_4$ is selected from —OH, —O—$CH_3$, —$NR_{17}R_{18}$, and -$Het_4$;

$R_5$ is selected from —H —$C_{1-3}$alkyl, and —$C_{3-6}$cycloalkyl; wherein each of said $C_{1-3}$alkyl is optionally and independently substituted with from 1 to 3 substituents selected from -halo, —OH, —$OCH_3$, -$Het_5$, and —$NR_{31}R_{32}$;

$R_6$ is selected from —OH, and —$NR_{33}R_{34}$;

$R_9$, $R_{10}$, $R_{11}$, $R_{12}$, $R_{13}$, $R_{14}$, $R_{31}$, $R_{32}$, $R_{33}$, and $R_{34}$ are each independently selected from —H and —$CH_3$;

$R_{17}$, $R_{18}$, $R_{27}$, and $R_{28}$ are each independently selected from —H and —$C_{1-2}$alkyl, each of said —$C_{1-2}$alkyl being optionally and independently substituted with from 1 to 3 substituents selected from —OH, -halo —$NR_{35}R_{36}$ and -$Het_7$;

$R_{29}$ and $R_{30}$, are each independently selected from —H, —OH and —$OCH_3$;

$R_{35}$ and $R_{36}$ are each independently selected from —H, —O, and $C_{1-6}$alkyl; wherein each of said $C_{1-6}$alkyl is optionally and independently substituted with from 1 to 3 substituents selected from -halo, —OH, —O—$C_{1-6}$alkyl, and —S—$C_{1-6}$alkyl;

$X_1$ is selected from —$C_{1-6}$alkyl-, —O—$C_{1-6}$alkyl, —(C=O)—, —S—$C_{1-6}$alkyl, —$NR_3$—(C=O)—, —$C_{1-6}$alkyl-$NR_3$—(C=O)—, —$NR_3$—(C=O)—$NR_{35}$—, —$NR_3$—$C_{1-6}$alkyl-, and —$NR_3$—$SO_2$—$C_{1-6}$alkyl-;

$X_2$ is selected from —$C_{1-6}$alkyl-, —O—$C_{1-6}$alkyl-, —(C=O)—$NR_2$—, and —$NR_2$—$C_{1-6}$alkyl-;

Y is selected from a direct bond, —$CHR_6$—, —O—, —S—, and —$NR_5$—;

$Het_1$ is selected from -piperidinyl and -piperazinyl; each of said $Het_1$ being substituted with $C_{1-2}$alkyl; each of said $C_{1-2}$alkyl being optionally and independently substituted with from 1 to 3-halo;

$Het_2$ is piperidinyl —$CH_3$;

$Het_3$ is selected from -piperazinyl, and -morpholinyl;

$Het_4$, is selected from -piperazinyl, and -morpholinyl; each of said $Het_4$ being optionally and independently substituted with $C_{1-2}$alkyl; each of said $C_{1-2}$alkyl being optionally and independently substituted with from 1 to 3 -halo;

$Het_5$ is -morpholinyl;

$Het_6$, is -piperazinyl;

$Het_7$ is -pyrrolidinyl;

$Z_1$, $Z_2$, $Z_3$, $Z_4$ and $Z_5$ are each independently selected from C and N; and m and n are each independently 1, 2, 3, or 4.

4. A compound as defined in claim 1, wherein:

$A_1$ and $A_2$ are selected from C and N; wherein when $A_1$ is C, then $A_2$ is N; and wherein when $A_2$ is C, then $A_1$ is N;

$R_1$ is selected from —H, -halo, —$C_{1-6}$alkyl, —$OC_{1-6}$alkyl, and —(C=O)—$R_4$; wherein each of said $C_{1-6}$alkyl is optionally and independently substituted with from 1 to 3 -halo;

$R_7$ is —H;

$R_2$ is selected from —H, —$C_{1-6}$alkyl, —(C=O)—O—$C_{1-6}$alkyl, and —(C=O)-$Het_3$; wherein each of said $C_{1-6}$alkyl is optionally and independently substituted with from 1 to 3 substituents selected from —OH, —$OC_{1-6}$alkyl, -$Het_3$, and —$NR_{13}R_{14}$;

$R_3$ is selected from —H, —$C_{1-6}$alkyl, and —(C=O)-$Het_2$; wherein each of said $C_{1-6}$alkyl is optionally and independently substituted with from 1 to 3 substituents —OH;

$R_4$ is selected from —OH, —O—$C_{1-6}$alkyl, —$NR_{17}R_{18}$, and -$Het_4$;

$R_5$ is selected from —H, —$C_{1-6}$alkyl, and —$C_{3-6}$cycloalkyl; wherein each of said $C_{1-6}$alkyl is optionally and independently substituted with from 1 to 3 substituents selected from —OH, and -$Het_5$;

$R_{13}$, $R_{14}$, $R_{17}$, $R_{18}$, $R_{19}$ and $R_{20}$ are each independently selected from —H, —O, —$C_{1-6}$alkyl, and $Het_1$;

$X_1$ is selected from —$C_{1-6}$alkyl-, —O—$C_{1-6}$alkyl-, —$NR_3$—(C=O)—, —$C_{1-6}$alkyl-$NR_3$—(C=O)—, and —$NR_3$—$C_{1-6}$alkyl-;

$X_2$ is selected from —O—$C_{1-6}$alkyl-, —(C=O)—$NR_2$—, and —$NR_2$—$C_{1-6}$alkyl-;

Y is selected from a direct bond, —O—, —S—, and —$NR_5$—;

$Het_1$, $Het_2$, $Het_3$, $Het_4$ and $Het_5$ are each independently a 5- or 6-membered monocyclic heterocycle having from 1 to 3 heteroatoms selected from O, N and S, wherein each heterocycle is being optionally substituted with from 1 to 3 —$C_{1-6}$alkyl;

$Z_1$, $Z_2$, $Z_3$, $Z_4$ and $Z_5$ are each independently selected from C and N; and m and n are each independently 1, 2, 3, or 4.

5. A compound as defined in claim 1, wherein:

$A_1$ and $A_2$ are selected from C and N; wherein when $A_1$ is C, then $A_2$ is N; and wherein when $A_2$ is C, then $A_1$ is N $R_1$ is selected from —H, -halo, —$CF_3$, —$OC_{1-6}$alkyl, and —(C=O)—$R_4$;

$R_7$ is —H;

$R_2$ is selected from —H, —$C_{1-6}$alkyl, —(C=O)—O—$C_{1-6}$alkyl, and —(C=O)-$Het_3$; wherein each of said $C_{1-6}$alkyl is optionally and independently substituted with from 1 to 3 substituents selected from —OH, —$OC_{1-6}$alkyl, -$Het_3$, and —$NR_{13}R_{14}$;

$R_3$ is selected from —H, —$C_{1-6}$alkyl, and —(C=O)-$Het_2$; wherein each of said $C_{1-6}$alkyl is optionally and independently substituted with from 1 to 3 —OH;

$R_4$ is selected from —OH, —$OC_{1-6}$alkyl, —$NR_{17}R_{18}$, and -$Het_4$;

$R_5$ is selected from —H, —$C_{1-6}$alkyl, —$C_{3-6}$cycloalkyl; wherein each of said $C_{1-6}$alkyl is optionally and independently substituted with from 1 to 3 substituents selected from —OH, and -$Het_5$;

$R_{13}$ and $R_{14}$ are each independently selected from —H, and —$C_{1-6}$alkyl;

$R_{17}$ and $R_{18}$ are each independently selected from —H, —$C_{1-6}$alkyl, and -Het$_1$;

$R_{19}$ and $R_{20}$ are each independently selected from —O, and —$C_{1-6}$alkyl;

$X_1$ is selected from —$C_{1-6}$alkyl-, —O—$C_{1-6}$alkyl-, —NR$_3$—(C=O)—, —$C_{1-6}$alkyl-NR$_3$—(C=O)—, and —NR$_3$—$C_{1-6}$alkyl-;

$X_2$ is selected from —O—$C_{1-6}$alkyl-, —(C=O)—NR$_2$—, and —NR$_2$—$C_{1-6}$alkyl-;

Y is selected from a direct bond, —O—, —S—, and —NR$_5$—;

Het$_1$, Het$_2$, Het$_3$, Het$_4$ and Het$_5$ are each independently selected from -morpholinyl, -piperidinyl, -piperazinyl, and pyrrolidinyl, wherein each heterocycle is optionally substituted with from 1 to 3 $C_{1-6}$alkyl;

$Z_1$, $Z_2$, $Z_3$, $Z_4$ and $Z_5$ are each independently selected from C and N; and m and n are each independently 1, 2, 3, or 4.

6. A compound as defined in claim 1, wherein:

$A_1$ and $A_2$ are selected from C and N; wherein when $A_1$ is C, then $A_2$ is N; and wherein when $A_2$ is C, then $A_1$ is N $R_1$ is selected from —H, -halo, —CF$_3$, —OCH$_3$, and —(C=O)—R$_4$;

$R_7$ is —H;

$R_2$ is selected from —H, —$C_{2-4}$alkyl, —(C=O)—O—$C_{2-4}$alkyl, and —(C=O)-Het$_3$; wherein each of said $C_{2-4}$alkyl is optionally and independently substituted with from 1 to 3 substituents selected from —OH, —OCH$_3$, -Het$_3$, and —NR$_{13}$R$_{14}$;

$R_3$ is selected from —H, —$C_{1-2}$alkyl, and —(C=O)-Het$_2$; wherein each of said $C_{1-2}$alkyl is optionally and independently substituted with from 1 to 3 —OH;

$R_4$ is selected from —OH, —OCH$_3$, —NR$_{17}$R$_{18}$, and -Het$_4$;

$R_5$ is selected from —H, —$C_{1-3}$alkyl, and —$C_{3-6}$cycloalkyl; wherein each $C_{1-3}$alkyl is optionally substituted with from 1 to 3 substituents selected from —OH, and -Het$_5$;

$R_{13}$ and $R_{14}$ are —CH$_3$;

$R_{17}$ and $R_{18}$ are each independently selected from —H, —CH$_3$, and -Het$_1$;

$R_{19}$ and $R_{20}$ are each —O;

$X_1$ is selected from —$C_{1-6}$alkyl-, —O—$C_{2-6}$alkyl-, —NR$_3$—(C=O)—, —$C_{1-6}$alkyl-NR$_3$—(C=O)—, and —NR$_3$—$C_{2-3}$alkyl-;

$X_2$ is selected from —O—$C_2$alkyl-, —(C=O)—NR$_2$—, and —NR$_2$—$C_{1-3}$alkyl-;

Y is selected from a direct bond, —O—, —S—, and —NR$_5$—;

Het$_1$, Het$_2$, Het$_3$, Het$_4$ and Het$_5$ are each independently selected from -morpholinyl, -piperidinyl, -piperazinyl, and pyrrolidinyl, wherein each heterocycle is optionally substituted with from 1 to 3 —CH$_3$;

$Z_1$, $Z_2$, $Z_3$, $Z_4$ and $Z_5$ are each independently selected from C and N; and m and n are each independently 1, 2, 3, or 4.

7. A compound as defined in claim 1, wherein:

$A_1$ and $A_2$ are selected from C and N; wherein when $A_1$ is C, then $A_2$ is N; and wherein when $A_2$ is C, then $A_1$ is N;

$R_1$ is selected from —H, -halo, —CF$_3$, —OCH$_3$, —(C=O)—OH, —(C=O)—OCH$_3$, —(C=O)-Het$_4$, —(C=O)—NH-Het$_4$, —(C=O)—NH$_2$, and —(C=O)—NH—CH$_3$;

$R_7$ is —H;

$R_2$ is selected from —H, —$C_{2-4}$alkyl, —(C=O)—O—$C_2$alkyl, and —(C=O)-Het$_3$; wherein each $C_{2-4}$alkyl is optionally and independently substituted with 1 substituent selected from —OH, —OCH$_3$, -Het$_3$, and —NR$_{13}$R$_{14}$;

$R_3$ is selected from —H, —$C_{1-2}$alkyl, and —(C=O)-Het$_2$; wherein said $C_{1-2}$alkyl is optionally and independently substituted with 1 —OH;

$R_5$ is selected from —H, —$C_{1-3}$alkyl, and —$C_{3-6}$cycloalkyl; wherein each $C_{1-3}$alkyl is optionally and independently substituted with 1 to 3 substituents selected from —OH, and -Het$_5$;

$R_{13}$ and $R_{14}$ are —CH$_3$;

$X_1$ is selected from —$C_{1-6}$alkyl-, —O—$C_{2-6}$alkyl-, —NR$_3$—(C=O)—, —$C_{1-6}$alkyl-NR$_3$—(C=O)—, and —NR$_3$—$C_2$alkyl-;

$X_2$ is selected from —O—$C_2$alkyl-, —(C=O)—NR$_2$—, and —NR$_2$—$C_{1-3}$alkyl-;

Y is selected from a direct bond, —O—, —S—, and —NR$_5$—;

Ar$_3$ is phenyl substituted with —NO$_2$;

Het$_2$ is -piperidinyl substituted with —CH$_3$;

Het$_3$ is selected from -morpholinyl, and -piperazinyl;

Het$_4$ is selected from -morpholinyl, -piperidinyl, and -piperazinyl; wherein said -piperidinyl and -piperazinyl are substituted with CH$_3$;

Het$_5$ is selected from -morpholinyl, and -pyrrolidinyl;

$Z_1$, $Z_2$, $Z_3$, $Z_4$ and $Z_5$ are each independently selected from C and N; and m and n are each independently 1, 2, 3, or 4.

8. A compound as defined in claim 1, wherein:

$A_1$ and $A_2$ are selected from C and N; wherein when $A_1$ is C, then $A_2$ is N; and wherein when $A_2$ is C, then $A_1$ is N;

$R_1$ and $R_7$ are each independently selected from —H, -halo, —$C_{1-6}$alkyl, —O—$C_{1-6}$alkyl, and —(C=O)—R$_4$; wherein each of said $C_{1-6}$alkyl is optionally and independently substituted with from 1 to 3 substituents selected from halo, and —OH;

$R_2$ is selected from —H, —$C_{1-6}$alkyl, —(C=O)—NR$_{27}$R$_{28}$, and —(C=O)-Het$_3$; wherein each of said $C_{1-6}$alkyl is optionally and independently substituted with from 1 to 3 substituents selected from -halo, —OH, and —NR$_{13}$R$_{14}$;

$R_3$ is selected from —H, —$C_{1-6}$alkyl, and —(C=O)-Het$_2$; wherein each of said $C_{1-6}$alkyl is optionally and independently substituted with —OH;

$R_4$ is independently selected from —OH, and —NR$_{17}$R$_{18}$;

$R_5$ is selected from —H —$C_{1-6}$alkyl, and —$C_{3-6}$cycloalkyl; wherein each of said $C_{1-6}$alkyl is optionally and independently substituted with from 1 to 3 substituents selected from -halo, —OH, —O$C_{1-6}$alkyl, -Het$_5$, and —NR$_{31}$R$_{32}$;

$R_{13}$, $R_{14}$, $R_{17}$, $R_{18}$, $R_{27}$, $R_{28}$, $R_{31}$, and $R_{32}$ are each independently selected from —H, and —$C_{1-6}$alkyl; wherein each of said $C_{1-6}$alkyl is optionally and independently substituted with from 1 to 3 substituents selected from -halo, —NR$_{35}$R$_{36}$, and -Het$_7$;

$R_{35}$ and $R_{36}$ are each —$C_{1-6}$alkyl;

$X_1$ is selected from —O—$C_{1-6}$alkyl-, —(C=O)—, —NR$_3$—(C=O)—, —$C_{1-6}$alkyl-NR$_3$—(C=O)—, and —NR$_3$—;

$X_2$ is selected from —O—$C_{1-6}$alkyl-, and —NR$_2$—;

Y is selected from a direct bond, —O—, and —NR$_5$—;

Het$_3$ is -piperazinyl

Het$_2$ is -piperidinyl substituted with —CH$_3$;

Het$_5$ is selected from -morpholinyl and -pyrrolidinyl;

Het$_7$ is -pyrrolidinyl;

$Z_1$, $Z_2$, $Z_3$, $Z_4$ and $Z_5$ are each independently selected from C and N; and m and n are each independently 1, 2, 3, or 4.

9. A compound as defined in claim 1, wherein:
$A_1$ is N; and $A_2$ is C;
$R_1$ and $R_7$ are each independently selected from —H, —$C_{1-6}$alkyl, —O—$C_{1-6}$alkyl, and —(C=O)—$R_4$; wherein each of said $C_{1-6}$alkyl is optionally and independently substituted with from 1 to 3 substituents selected from -halo, and —OH;
$R_2$ is selected from —H, —$C_{1-6}$alkyl, and —(C=O)—$NR_{27}R_{28}$; wherein each of said $C_{1-6}$alkyl is optionally and independently substituted with from 1 to 3 substituents selected from —OH;
$R_3$ is selected from —H, —$C_{1-6}$alkyl, and —(C=O)-$Het_2$; wherein each of said $C_{1-6}$alkyl is optionally and independently substituted with —OH;
$R_4$ is independently selected from —OH, and —$NR_{17}R_{18}$;
$R_5$ is selected from —H —$C_{1-6}$alkyl, and —$C_{3-6}$cycloalkyl; wherein each of said $C_{1-6}$alkyl is optionally and independently substituted with from 1 to 3 substituents selected from -halo, —OH, —$OC_{1-6}$alkyl, and -$Het_5$;
$R_{17}$, $R_{18}$, $R_{27}$, and $R_{28}$ are each independently selected from —H, and —$C_{1-6}$alkyl; wherein each of said $C_{1-6}$alkyl is optionally and independently substituted with from 1 to 3 substituents selected from —$NR_{35}R_{36}$, and -$Het_7$;
$R_{35}$ and $R_{36}$ are each —$C_{1-6}$alkyl;
$X_1$ is selected from —O—$C_{1-6}$alkyl-, —$NR_3$—(C=O)—, and —$NR_3$—;
$X_2$ is selected from —O—$C_{1-6}$alkyl-, and —$NR_2$—;
Y is selected from a direct bond, —O—, and —$NR_5$—;
$Het_2$ is -piperidinyl substituted with —$CH_3$;
$Het_5$ is selected from -morpholinyl and -pyrrolidinyl;
$Het_7$ is -pyrrolidinyl;
$Z_1$, $Z_2$, $Z_3$, $Z_4$ and $Z_5$ are each C; and
m and n are each independently 1, 2, 3, or 4.

10. A compound as defined in claim 1, wherein:
$A_1$ is N; and $A_2$ is C;
$R_1$ and $R_7$ are each —H;
$R_2$ is selected from —H, —(C=O)—$NR_{27}R_{28}$ and —$C_{1-6}$alkyl; wherein each of said $C_{1-6}$alkyl is optionally and independently substituted with from 1 to 3 —OH;
$R_5$ is selected from —H and —$C_{1-6}$alkyl; wherein each of said $C_{1-6}$alkyl is optionally and independently substituted with from 1 to 3 -$Het_5$;
$R_{27}$, and $R_{28}$ are each independently selected from —H, and —$C_{1-6}$alkyl; wherein each of said $C_{1-6}$alkyl is optionally and independently substituted with from 1 to 3 substituents selected from —$NR_{35}R_{36}$, and -$Het_7$;
$R_{35}$ and $R_{36}$ are each —$C_{1-6}$alkyl;
$X_1$ is —O—$CH_2$—;
$X_2$ is selected from —O—$CH_2$—, and —$NR_2$—;
Y is —$NR_5$—;
$Het_5$ is selected from -morpholinyl and -pyrrolidinyl;
$Het_7$ is -pyrrolidinyl;
$Z_1$, $Z_2$, $Z_3$, $Z_4$ and $Z_5$ are each C;
m is 1; and
n is selected from 1, 2 and 3.

11. A compound as defined in claim 1, wherein said compound is selected from the group consisting of:

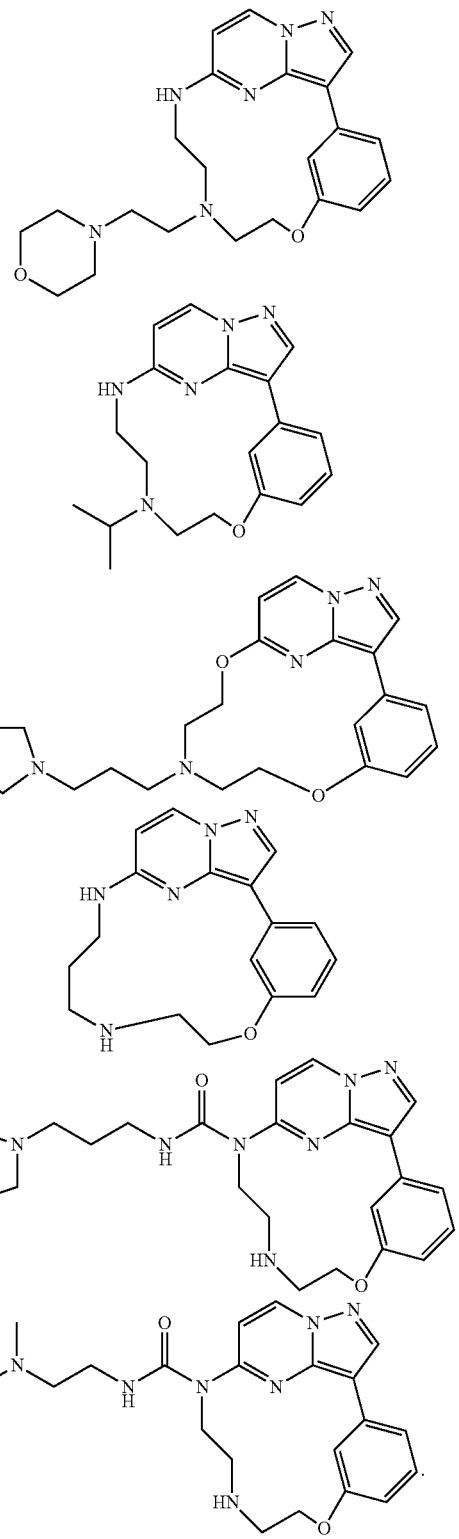

12. A compound as defined in claim 1, wherein the bicyclic ring containing $A_1$ and $A_2$ is linked to the ring containing $Z_1$-$Z_5$ at position $Z_4$ and wherein $R_7$ is linked to the ring containing $Z_1$-$Z_5$ at position $Z_5$ in accordance with Formula I.

13. A pharmaceutical composition comprising a compound as defined in claim 1, for use as a human or veterinary medicine.

14. A pharmaceutical composition comprising a compound as defined in claim 1 and one or more pharmaceutically acceptable carriers, diluents, excipients, or adjuvants.

* * * * *